(12) United States Patent
Jiang et al.

(10) Patent No.: US 11,618,786 B2
(45) Date of Patent: Apr. 4, 2023

(54) ANTI-PD-L1 ANTIBODIES AND VARIANTS

(71) Applicant: Shanghai Henlius Biotech Inc., Shanghai (CN)

(72) Inventors: Weidong Jiang, Fremont, CA (US); Pei-Hua Lin, Fremont, CA (US); Chi-Ling Tseng, Taipei (TW)

(73) Assignee: Shanghai Henlius Biotech Inc., Shanghai (CN)

( * ) Notice: Subject to any disclaimer, the term of this patent is extended or adjusted under 35 U.S.C. 154(b) by 0 days.

(21) Appl. No.: 17/583,521

(22) Filed: Jan. 25, 2022

(65) Prior Publication Data
US 2022/0144955 A1 May 12, 2022

Related U.S. Application Data

(63) Continuation of application No. 16/380,493, filed on Apr. 10, 2019, now Pat. No. 11,274,155, which is a continuation of application No. PCT/US2017/056689, filed on Oct. 14, 2017.

(60) Provisional application No. 62/414,785, filed on Oct. 30, 2016.

(51) Int. Cl.
| | |
|---|---|
| *C07K 16/28* | (2006.01) |
| *G01N 33/574* | (2006.01) |
| *A61P 35/00* | (2006.01) |
| *C07K 16/22* | (2006.01) |
| *A61K 39/395* | (2006.01) |
| *A61K 39/00* | (2006.01) |

(52) U.S. Cl.
CPC .... *C07K 16/2827* (2013.01); *A61K 39/39558* (2013.01); *A61P 35/00* (2018.01); *C07K 16/22* (2013.01); *G01N 33/57492* (2013.01); *A61K 2039/505* (2013.01); *A61K 2039/507* (2013.01); *A61K 2039/876* (2018.08); *C07K 2317/21* (2013.01); *C07K 2317/33* (2013.01); *C07K 2317/41* (2013.01); *C07K 2317/51* (2013.01); *C07K 2317/515* (2013.01); *C07K 2317/565* (2013.01); *C07K 2317/74* (2013.01); *C07K 2317/76* (2013.01); *C07K 2317/92* (2013.01); *G01N 2333/70532* (2013.01); *G01N 2333/70596* (2013.01)

(58) Field of Classification Search
CPC ............... C07K 16/2827; C07K 16/22; C07K 2317/21; A61K 39/39558
See application file for complete search history.

(56) References Cited

U.S. PATENT DOCUMENTS

2013/0130268 A1    5/2013   Moroncini et al.

FOREIGN PATENT DOCUMENTS

| WO | 2007005874 | 1/2007 |
|---|---|---|
| WO | 2008130704 | 10/2008 |
| WO | 2010077634 | 7/2010 |
| WO | 2011066389 | 6/2011 |
| WO | 2013079174 | 6/2013 |
| WO | 2015061668 | 4/2015 |
| WO | 2016073879 | 5/2016 |

OTHER PUBLICATIONS

International Search Report & Written Opinion dated Feb. 23, 2018 for PCT Application No. PCT/US2017/056689.
European Search Report dated Jun. 5, 2020 for European Patent Application No. 17864351.6.
Chen, Lieping and Xue Han, "AntiPD-1/PD-L1 therapy of human cancer: past, present and future." The Journal of clinical investigation 125.9 (2015): 3384-3391.

*Primary Examiner* — Peter J Reddig
*Assistant Examiner* — Cheng Lu
(74) *Attorney, Agent, or Firm* — Lei Fang, Esq.; Smith Tempel Blaha LLC

(57) ABSTRACT

Provided are anti-PD-L1 antibodies, variants, mutants, and antigen binding fragments thereof. Also provided are isolated nucleic acid molecules that encode the anti-PD-L1 antibodies, variants, mutants, or antigen binding fragments thereof, and related expression vectors, and host cells. Provided are methods of making anti-PD-L1 antibodies, variants, mutants, and antigen binding fragments thereof. Also provided are related pharmaceutical compositions and methods of their use to treat subjects. This abstract is intended as a scanning tool for purposes of searching in the particular art and is not intended to be limiting of the present disclosure.

23 Claims, 27 Drawing Sheets
Specification includes a Sequence Listing.

Figure 1A

```
               1                                                              50
PL1_LC   .QAVLTQPSS  VSGAPGQRVT  ISCTGSSSNV  GAGYDVHWYQ  QLPGTAPKLL
PL2_LC   .QSVVTQPPS  MSAAPGQNVT  ISCSGSSS.Y  IESSYVSWYQ  QLPGTAPRLL
PL3_LC   .QSVVTQPPP  VSGAPGQRVT  ISCTGSSSNI  GAGYDVHWYQ  QLPGTAPKLL
PL6_LC   .QSVVTQPPS  VSGAPGQRVT  ISCTGSSSNI  GAGYDVHWYQ  QLPGTAPKLL
PL8_LC   LSSELTQDPA  VSVALGQTVR  ITCQGDSL..  .RSYYVSWYQ  QKPGQAPVLV
PL12_LC  .QSVLTQPPS  VSGAPGQRVT  ISCTRSSSNI  GAGHDVHWYQ  QLPGTAPKLL
PL15_LC  .QSVLTQPPS  VSGAPGQRVT  ISCTGYSSNI  GAGYDVHWYQ  HLPGTAPKLL 51                                                             100
PL1_LC   IYGNSNRPSG  VPDRFSGSKS  GTSASLAITG  LQAEDEADYY  CQSYDSSLSG
PL2_LC   IYDDDMRPSG  IPDRFSGSKS  GTSATLAITG  LQTGDEADYY  CEIWDSGLGG
PL3_LC   IYGNSNRPSG  VPDRFSGSKS  GTSASLAITG  LQAEDEADYY  CQSYDSSLSA
PL6_LC   IYGNSNRPSG  VPDRFSGSKS  GTSASLAITG  LQAEDEADYY  CQSYDSSLSG
PL8_LC   LYGKNNRPSG  IPDRFSGSSS  GSTASLTITG  AQAEDEADYY  CNSRDSTGNL
PL12_LC  IYGNSNRPSG  VPDRFSGSKS  GTSASLAITG  LQAEDGADYY  CQSYDSSLTG
PL15_LC  IYGNSNRPSG  VPDRFSGSKS  GTSASLAITG  LQAEDEADYY  CQSYDNSLSV 101                                                             150
PL1_LC   .WVFGGGTKL  TVLGQPKAAP  SVTLFPPSSE  ELQANKATLV  CLISDFYPGA
PL2_LC   ..VFGGGTKL  TVLSQPKAAP  SVTLFPPSSE  ELQANKATLV  CLISDFYPGA
PL3_LC   PVVFGGGTKL  TVLGQPKAAP  SVTLFPPSSE  ELQANKATLV  CLISDFYPGA
PL6_LC   .GVFGGGTKL  TVLGQPKAAP  SVTLFPPSSE  ELQANKATLV  CLISDFYPGA
PL8_LC   LRVFGGGTKL  TVLGQPKAAP  SITLFPPSSE  ELQANKATLV  CLISDFYPGA
PL12_LC  .VVFGGGTKL  TVLGQPKAAP  SVTLFPPSSE  ELQANKATLV  CLISDFYPGA
PL15_LC  .SVFGGGTKL  TVLGQPKAAP  SVTLFPPSSE  ELQANKATLV  CLISDFYPGA 151                                                             200
PL1_LC   VTVAWKADSS  PVKAGVETTT  PSKQSNNKYA  ASSYLSLTPE  QWKSHRSYSC
PL2_LC   VTVAWKADSS  PVKAGVETTT  PSKQSNNKYA  ASSYLSLTPE  QWKSHKSYSC
PL3_LC   VTVAWKADSS  PVKAGVETTT  PSKQSNNKYA  ASSYLSLTPE  QWKSHKSYSC
PL6_LC   VTVAWKADSS  PVKAGVETTT  PSKQSNNKYA  ASSYLSLTPE  QWKSHRSYSC
PL8_LC   VTVAWKADSS  PVKAGVETTT  PSKQSNNKYA  ASSYLSLTPE  QWKSHRSYSC
PL12_LC  VTVAWKADSS  PVKAGVETTT  PSKQSNNKYA  ASSYLSLTPE  QWKSHRSYSC
PL15_LC  VTVAWKADSS  PVKAGVETTT  PSKQSNNKYA  ASSYLSLTPE  QWKSHRSYSC 201        218
PL1_LC   QVTHEGSTVE  KTVALTEC  (SEQ ID NO:1)
PL2_LC   QVTHEGSTVE  RTVALTEC  (SEQ ID NO:2)
PL3_LC   QVTHEGSTVE  KTVALTEC  (SEQ ID NO:3)
PL6_LC   QVTHEGSTVE  KTVALTEC  (SEQ ID NO:4)
PL8_LC   QVTHEGSTVE  KTVALTEC  (SEQ ID NO:5)
PL12_LC  QVTHEGSTVE  KTVALTEC  (SEQ ID NO:6)
PL15_LC  QVTHEGSTVE  KTVALTEC  (SEQ ID NO:7)
```

Figure 1B

```
              1                                                      50
PL1_HC    QIQLVQSGAE VKKPGSSVKV SCKASGGTFS SYAISWVRQA PGQGLEWMGR
PL2_HC    EVQLVQSGGG LVKPGGSLRL SCAASGFTFS SYTMNWVRQA PGKGLEWVSS
PL3_HC    QVQLVQSGAE VKKPGSSVKV SCKASGGTFS SYTISWVRQA PGQGLEWMGR
PL6_HC    EVQLVQSGAE VKKPGSSVKV SCKASGGTFS SYTINWVRQA PGQGLEWVGK
PL8_HC    EVQLVQSGAE VKKPGSSVKV SCKASGGTFS SYAISWVRQA PGQGLEWMGR
PL12_HC   QVQLVQSGAE VKKPGSSVKV SCKASGGTFS SYAISWVRQA PGQGLEWMGR
PL15_HC   QVQLVQSGAE VKKPGSSVKV SCKASGGTFS SYTISWVRQA PGQGLEWMGR 51                                                     100
PL1_HC    IIPILGIANY AQKFQGRVTI TAGESTSTAY MELSSLRSED TAVYYCAREG
PL2_HC    ISSGSDYLYY ADSVKGRFTI SRDNAKNSLY LQMNSLRAED TAVYYCARNE
PL3_HC    IIPILGIANY AQKFQGRVTI TADKSTSTAY MELSSLRSED TAVYYCARSR
PL6_HC    IIPILGIADY AQMFKGRVTI TADKFTSTVY MELNSLRSED TAVYYCARGG
PL8_HC    IIPIFGTANY AQKFQGRVTI TADESTSTAY MELSSLRSED TAVYYCAREG
PL12_HC   IIPILGIANY AQKFQGRVTI TADKSTSTAY MELSSLRSED TAVYYCARGI
PL15_HC   IIPILGIANY AQKFQGRVTI TADKSTSTAY MELSSLRSED TAVYYCARSR 101                                                    150
PL1_HC    S..SGWLGVL DYWGQGTLVT VSSASTKGPS VFPLAPSSKS TSGGTAALGC
PL2_HC    LRWYPQAGAF DIWGQGTMVT VSSASTKGPS VFPLAPSSKS TSGGTAALGC
PL3_HC    D..GYSFGAF DIWGQGTLVT VSSASTKGPS VFPLAPSSKS TSGGTAALGC
PL6_HC    Y..VGYLNAF DIWGQGTMVT VSSASTKGPS VFPLAPSSKS TSGGTAALGC
PL8_HC    .....VLDAF DIWGQGTMVT VSSASTKGPS VFPLAPSSKS TSGGTAALGC
PL12_HC   G..SYSFGAF DIWGQGTMVT VSSASTKGPS VFPLAPSSKS TSGGTAALGC
PL15_HC   D..GYSFGAF DIWGQGTLVT VSSASTKGPS VFPLAPSSKS TSGGTAALGC 151                                                    200
PL1_HC    LVKDYFPEPV TVSWNSGALT SGVHTFPAVL QSSGLYSLSS VVTVPSSSLG
PL2_HC    LVKDYFPEPV TVSWNSGALT SGVHTFPAVL QSSGLYSLSS VVTVPSSSLG
PL3_HC    LVKDYFPEPV TVSWNSGALT SGVHTFPAVL QSSGLYSLSS VVTVPSSSLG
PL6_HC    LVKDYFPEPV TVSWNSGALT SGVHTFPAVL QSSGLYSLSS VVTVPSSSLG
PL8_HC    LVKDYFPEPV TVSWNSGALT SGVHTFPAVL QSSGLYSLSS VVTVPSSSLG
PL12_HC   LVKDYFPEPV TVSWNSGALT SGVHTFPAVL QSSGLYSLSS VVTVPSSSLG
PL15_HC   LVKDYFPEPV TVSWNSGALT SGVHTFPAVL QSSGLYSLSS VVTVPSSSLG 201                                                    250
PL1_HC    TQTYICNVNH KPSNTKVDKK VEPKSCDKTH TCPPCPAPEL LGGPSVFLFP
PL2_HC    TQTYICNVNH KPSNTKVDKK VEPKSCDKTH TCPPCPAPEL LGGPSVFLFP
PL3_HC    TQTYICNVNH KPSNTKVDKK VEPKSCDKTH TCPPCPAPEL LGGPSVFLFP
PL6_HC    TQTYICNVNH KPSNTKVDKK VEPKSCDKTH TCPPCPAPEL LGGPSVFLFP
PL8_HC    TQTYICNVNH KPSNTKVDKK VEPKSCDKTH TCPPCPAPEL LGGPSVFLFP
PL12_HC   TQTYICNVNH KPSNTKVDKK VEPKSCDKTH TCPPCPAPEL LGGPSVFLFP
PL15_HC   TQTYICNVNH KPSNTKVDKK VEPKSCDKTH TCPPCPAPEL LGGPSVFLFP 251                                                    300
PL1_HC    PKPKDTLMIS RTPEVTCVVV DVSHEDPEVK FNWYVDGVEV HNAKTKPREE
PL2_HC    PKPKDTLMIS RTPEVTCVVV DVSHEDPEVK FNWYVDGVEV HNAKTKPREE
PL3_HC    PKPKDTLMIS RTPEVTCVVV DVSHEDPEVK FNWYVDGVEV HNAKTKPREE
PL6_HC    PKPKDTLMIS RTPEVTCVVV DVSHEDPEVK FNWYVDGVEV HNAKTKPREE
PL8_HC    PKPKDTLMIS RTPEVTCVVV DVSHEDPEVK FNWYVDGVEV HNAKTKPREE
PL12_HC   PKPKDTLMIS RTPEVTCVVV DVSHEDPEVK FNWYVDGVEV HNAKTKPREE
PL15_HC   PKPKDTLMIS RTPEVTCVVV DVSHEDPEVK FNWYVDGVEV HNAKTKPREE
```

Figure 1B (Con't)

```
         301                                                  350
PL1_HC   QYASTYRVVS  VLTVLHQDWL  NGKEYKCKVS  NKALPAPIEK  TISKAKGQPR
PL2_HC   QYASTYRVVS  VLTVLHQDWL  NGKEYKCKVS  NKALPAPIEK  TISKAKGQPR
PL3_HC   QYASTYRVVS  VLTVLHQDWL  NGKEYKCKVS  NKALPAPIEK  TISKAKGQPR
PL6_HC   QYASTYRVVS  VLTVLHQDWL  NGKEYKCKVS  NKALPAPIEK  TISKAKGQPR
PL8_HC   QYASTYRVVS  VLTVLHQDWL  NGKEYKCKVS  NKALPAPIEK  TISKAKGQPR
PL12_HC  QYASTYRVVS  VLTVLHQDWL  NGKEYKCKVS  NKALPAPIEK  TISKAKGQPR
PL15_HC  QYASTYRVVS  VLTVLHQDWL  NGKEYKCKVS  NKALPAPIEK  TISKAKGQPR 351                                                  400
PL1_HC   EPQVYTLPPS  REEMTKNQVS  LTCLVKGFYP  SDIAVEWESN  GQPENNYKTT
PL2_HC   EPQVYTLPPS  REEMTKNQVS  LTCLVKGFYP  SDIAVEWESN  GQPENNYKTT
PL3_HC   EPQVYTLPPS  REEMTKNQVS  LTCLVKGFYP  SDIAVEWESN  GQPENNYKTT
PL6_HC   EPQVYTLPPS  REEMTKNQVS  LTCLVKGFYP  SDIAVEWESN  GQPENNYKTT
PL8_HC   EPQVYTLPPS  REEMTKNQVS  LTCLVKGFYP  SDIAVEWESN  GQPENNYKTT
PL12_HC  EPQVYTLPPS  REEMTKNQVS  LTCLVKGFYP  SDIAVEWESN  GQPENNYKTT
PL15_HC  EPQVYTLPPS  REEMTKNQVS  LTCLVKGFYP  SDIAVEWESN  GQPENNYKTT 401                                                  450
PL1_HC   PPVLDSDGSF  FLYSKLTVDK  SRWQQGNVFS  CSVMHEALHN  HYTQKSLSLS
PL2_HC   PPVLDSDGSF  FLYSKLTVDK  SRWQQGNVFS  CSVMHEALHN  HYTQKSLSLS
PL3_HC   PPVLDSDGSF  FLYSKLTVDK  SRWQQGNVFS  CSVMHEALHN  HYTQKSLSLS
PL6_HC   PPVLDSDGSF  FLYSKLTVDK  SRWQQGNVFS  CSVMHEALHN  HYTQKSLSLS
PL8_HC   PPVLDSDGSF  FLYSKLTVDK  SRWQQGNVFS  CSVMHEALHN  HYTQKSLSLS
PL12_HC  PPVLDSDGSF  FLYSKLTVDK  SRWQQGNVFS  CSVMHEALHN  HYTQKSLSLS
PL15_HC  PPVLDSDGSF  FLYSKLTVDK  SRWQQGNVFS  CSVMHEALHN  HYTQKSLSLS

451
PL1_HC   PGK  (SEQ ID NO:8)
PL2_HC   PGK  (SEQ ID NO:9)
PL3_HC   PGK  (SEQ ID NO:10)
PL6_HC   PGK  (SEQ ID NO:11)
PL8_HC   PGK  (SEQ ID NO:12)
PL12_HC  PGK  (SEQ ID NO:13)
PL15_HC  PGK  (SEQ ID NO:14)
```

Figure 11A

```
              1                                                            50
   PL2#3_LC   QSVVTQPPSM SAAPGQRVTI SCSGSSS.YI ESSYVGWYQQ LPGTAPRLLI
   PL3#7_LC   QSVVTQPPPV SGAPGQRVTI SCTGSSSNIG AGYDVHWYQQ LPGTAPKLLI
PL3#7-19_LC   QSVVTQPPPV SGAPGQRVTI SCTGSSSNIG GGYDVHWYQQ LPGTAPKLLI
PL3#7-43_LC   QSVVTQPPPV SGAPGQRVTI SCTGSSSNVG AGYDVHWYQQ LPGTAPKLLI
PL3#7-54_LC   QSVVTQPPPV SGAPGQRVTI SCTGSSSNIG QGYDVHWYQQ LPGTAPKLLI 51                                                           100
   PL2#3_LC   YDDDMRPSGI PDRFSGSKSG TSATLAITGL QTGDEADYYC EIWRSGLGG.
   PL3#7_LC   YGNSNRPSGV PDRFSGSKSG TSASLAITGL QAEDEADYYC QTYDSSLSAR
PL3#7-19_LC   YGNSTRPSGV PDRFSGSKSG TSASLAITGL QAEDEADYYC QTYDSSLSAT
PL3#7-43_LC   YGNSNRSSGV PDRFSGSKSG TSASLAITGL QAEDEADYYC QTYDSSGSAR
PL3#7-54_LC   YANSNRPSGV PDRFSGSKSG TSASLAITGL QAEDEADYYC QTYDSSLSAR 101                                                          150
   PL2#3_LC   .VFGGGTKLT VLSQPKAAPS VTLFPPSSEE LQANKATLVC LISDFYPGAV
   PL3#7_LC   VVFGGGTKLT VLGQPKAAPS VTLFPPSSEE LQANKATLVC LISDFYPGAV
PL3#7-19_LC   VVFGGGTKLT VLGQPKAAPS VTLFPPSSEE LQANKATLVC LISDFYPGAV
PL3#7-43_LC   VVFGGGTKLT VLGQPKAAPS VTLFPPSSEE LQANKATLVC LISDFYPGAV
PL3#7-54_LC   VVFGGGTKLT VLGQPKAAPS VTLFPPSSEE LQANKATLVC LISDFYPGAV 151                                                          200
   PL2#3_LC   TVAWKADSSP VKAGVETTTP SKQSNNKYAA SSYLSLTPEQ WKSHKSYSCQ
   PL3#7_LC   TVAWKADSSP VKAGVETTTP SKQSNNKYAA SSYLSLTPEQ WKSHKSYSCQ
PL3#7-19_LC   TVAWKADSSP VKAGVETTTP SKQSNNKYAA SSYLSLTPEQ WKSHKSYSCQ
PL3#7-43_LC   TVAWKADSSP VKAGVETTTP SKQSNNKYAA SSYLSLTPEQ WKSHKSYSCQ
PL3#7-54_LC   TVAWKADSSP VKAGVETTTP SKQSNNKYAA SSYLSLTPEQ WKSHKSYSCQ 201        217
   PL2#3_LC   VTHEGSTVER TVALTEC
   PL3#7_LC   VTHEGSTVEK TVALTEC
PL3#7-19_LC   VTHEGSTVEK TVALTEC
PL3#7-43_LC   VTHEGSTVEK TVALTEC
PL3#7-54_LC   VTHEGSTVEK TVALTEC
```

Figure 11B

```
                 1                                                        50
    PL2#3_HC    EVQLVQSGGG LVKPGGSLRL SCAASGFTFS SYTMNWVRQA PGKGLEWVSS
    PL3#7_HC    QVQLVQSGAE VKKPGSSVKV SCKASGGTFS SYPISWVRQA PGQGLEWIGR
 PL3#7-19_HC    QVQLVQSGAE VKKPGSSVKV SCKASGGTFS SYPISWVRQA PGQGLEWMGR
 PL3#7-43_HC    QVQLVQSGAE VKKPGSSVKV SCKASGGTFS SYPISWVRQA PGQGLEWMGR
 PL3#7-54_HC    QVQLVQSGAE VKKPGSSVKV SCKASGGTFS SYPISWVRQA PGQGLEWMGR 51                                                       100
    PL2#3_HC    ISSGSDYLYY ADSVKGRFTI SRDNAKNSLY LQMNSLRAED TAVYYCARNE
    PL3#7_HC    IIPILGIANY AQKFQGRVTI TADKSTSTAY MELSSLRSED TAVYYCAR..
 PL3#7-19_HC    IIPILGIANY AQKFQGRVTI TADKSTSTAY MELSSLRSED TAVYYCAR..
 PL3#7-43_HC    IIPILGIANY AQKFQGRVTI TADKSTSTAY MELSSLRSED TAVYYCAR..
 PL3#7-54_HC    IIPILGIADY AQKFQGRVTI TADKSTSTAY MELSSLRSED TAVYYCAR..

101                                                      150
    PL2#3_HC    LRWYPQAGAF DRWGQGTMVT VSSASTKGPS VFPLAPSSKS TSGGTAALGC
    PL3#7_HC    SRDGYAFGAF DIWGQGTLVT VSSASTKGPS VFPLAPSSKS TSGGTAALGC
 PL3#7-19_HC    SRDGYAFGAF DVWGQGTLVT VSSASTKGPS VFPLAPSSKS TSGGTAALGC
 PL3#7-43_HC    SRPGYAFGAF DIWGQGTLVT VSSASTKGPS VFPLAPSSKS TSGGTAALGC
 PL3#7-54_HC    SRPGYAFGAF DIWGQGTLVT VSSASTKGPS VFPLAPSSKS TSGGTAALGC 151                                                      200
    PL2#3_HC    LVKDYFPEPV TVSWNSGALT SGVHTFPAVL QSSGLYSLSS VVTVPSSSLG
    PL3#7_HC    LVKDYFPEPV TVSWNSGALT SGVHTFPAVL QSSGLYSLSS VVTVPSSSLG
 PL3#7-19_HC    LVKDYFPEPV TVSWNSGALT SGVHTFPAVL QSSGLYSLSS VVTVPSSSLG
 PL3#7-43_HC    LVKDYFPEPV TVSWNSGALT SGVHTFPAVL QSSGLYSLSS VVTVPSSSLG
 PL3#7-54_HC    LVKDYFPEPV TVSWNSGALT SGVHTFPAVL QSSGLYSLSS VVTVPSSSLG 201                                                      250
    PL2#3_HC    TQTYICNVNH KPSNTKVDKK VEPKSCDKTH TCPPCPAPEL LGGPSVFLFP
    PL3#7_HC    TQTYICNVNH KPSNTKVDKK VEPKSCDKTH TCPPCPAPEL LGGPSVFLFP
 PL3#7-19_HC    TQTYICNVNH KPSNTKVDKK VEPKSCDKTH TCPPCPAPEL LGGPSVFLFP
 PL3#7-43_HC    TQTYICNVNH KPSNTKVDKK VEPKSCDKTH TCPPCPAPEL LGGPSVFLFP
 PL3#7-54_HC    TQTYICNVNH KPSNTKVDKK VEPKSCDKTH TCPPCPAPEL LGGPSVFLFP 251                                                      300
    PL2#3_HC    PKPKDTLMIS RTPEVTCVVV DVSHEDPEVK FNWYVDGVEV HNAKTKPREE
    PL3#7_HC    PKPKDTLMIS RTPEVTCVVV DVSHEDPEVK FNWYVDGVEV HNAKTKPREE
 PL3#7-19_HC    PKPKDTLMIS RTPEVTCVVV DVSHEDPEVK FNWYVDGVEV HNAKTKPREE
 PL3#7-43_HC    PKPKDTLMIS RTPEVTCVVV DVSHEDPEVK FNWYVDGVEV HNAKTKPREE
 PL3#7-54_HC    PKPKDTLMIS RTPEVTCVVV DVSHEDPEVK FNWYVDGVEV HNAKTKPREE 301                                                      350
    PL2#3_HC    QYASTYRVVS VLTVLHQDWL NGKEYKCKVS NKALPAPIEK TISKAKGQPR
    PL3#7_HC    QYASTYRVVS VLTVLHQDWL NGKEYKCKVS NKALPAPIEK TISKAKGQPR
 PL3#7-19_HC    QYASTYRVVS VLTVLHQDWL NGKEYKCKVS NKALPAPIEK TISKAKGQPR
 PL3#7-43_HC    QYASTYRVVS VLTVLHQDWL NGKEYKCKVS NKALPAPIEK TISKAKGQPR
 PL3#7-54_HC    QYASTYRVVS VLTVLHQDWL NGKEYKCKVS NKALPAPIEK TISKAKGQPR
```

Figure 11B (Con't)

```
                351                                                         400
    PL2#3_HC    EPQVYTLPPS REEMTKNQVS LTCLVKGFYP SDIAVEWESN GQPENNYKTT
    PL3#7_HC    EPQVYTLPPS REEMTKNQVS LTCLVKGFYP SDIAVEWESN GQPENNYKTT
 PL3#7-19_HC    EPQVYTLPPS REEMTKNQVS LTCLVKGFYP SDIAVEWESN GQPENNYKTT
 PL3#7-43_HC    EPQVYTLPPS REEMTKNQVS LTCLVKGFYP SDIAVEWESN GQPENNYKTT
 PL3#7-54_HC    EPQVYTLPPS REEMTKNQVS LTCLVKGFYP SDIAVEWESN GQPENNYKTT 401                                                         450
    PL2#3_HC    PPVLDSDGSF FLYSKLTVDK SRWQQGNVFS CSVMHEALHN HYTQKSLSLS
    PL3#7_HC    PPVLDSDGSF FLYSKLTVDK SRWQQGNVFS CSVMHEALHN HYTQKSLSLS
 PL3#7-19_HC    PPVLDSDGSF FLYSKLTVDK SRWQQGNVFS CSVMHEALHN HYTQKSLSLS
 PL3#7-43_HC    PPVLDSDGSF FLYSKLTVDK SRWQQGNVFS CSVMHEALHN HYTQKSLSLS
 PL3#7-54_HC    PPVLDSDGSF FLYSKLTVDK SRWQQGNVFS CSVMHEALHN HYTQKSLSLS

451
    PL2#3_HC    PGK
    PL3#7_HC    PGK
 PL3#7-19_HC    PGK
 PL3#7-43_HC    PGK
 PL3#7-54_HC    PGK
```

Figure 18

```
                          1                                                    50
PL3#7     LC(parental)    QSVVTQPPPV SGAPGQRVTI SCTGSSSNIG AGYDVHWYQQ LPGTAPKLLI
PL3#7-19_LC(parental)     QSVVTQPPPV SGAPGQRVTI SCTGSSSNIG GGYDVHWYQQ LPGTAPKLLI
PL3#7-19_LC(deglyco1)     QSVVTQPPPV SGAPGQRVTI SCTGSSSNIG GGYDVHWYQQ LPGTAPKLLI
PL3#7-19_LC(deglyco2)     QSVVTQPPPV SGAPGQRVTI SCTGSSSNIG GGYDVHWYQQ LPGTAPKLLI
PL3#7-19_LC(deglyco3)     QSVVTQPPPV SGAPGQRVTI SCTGSSSNIG GGYDVHWYQQ LPGTAPKLLI
PL3#7-43_LC(parental)     QSVVTQPPPV SGAPGQRVTI SCTGSSSNVG AGYDVHWYQQ LPGTAPKLLI
PL3#7-43_LC(deglyco1)     QSVVTQPPPV SGAPGQRVTI SCTGSSSNVG AGYDVHWYQQ LPGTAPKLLI
PL3#7-43_LC(deglyco2)     QSVVTQPPPV SGAPGQRVTI SCTGSSSNVG AGYDVHWYQQ LPGTAPKLLI
                          51                                                   100
PL3#7     LC(parental)    YGNSNRPSGV PDRFSGSKSG TSASLAITGL QAEDEADYYC QTYDSSLSAR
PL3#7-19_LC(parental)     YGNSTRPSGV PDRFSGSKSG TSASLAITGL QAEDEADYYC QTYDSSLSAT
PL3#7-19_LC(deglyco1)     YGNSNRPSGV PDRFSGSKSG TSASLAITGL QAEDEADYYC QTYDSSLSAT
PL3#7-19_LC(deglyco2)     YGQSTRPSGV PDRFSGSKSG TSASLAITGL QAEDEADYYC QTYDSSLSAT
PL3#7-19_LC(deglyco3)     YGNSQRPSGV PDRFSGSKSG TSASLAITGL QAEDEADYYC QTYDSSLSAT
PL3#7-43_LC(parental)     YGNSNRSSGV PDRFSGSKSG TSASLAITGL QAEDEADYYC QTYDSSGSAR
PL3#7-43_LC(deglyco1)     YGNSNRPSGV PDRFSGSKSG TSASLAITGL QAEDEADYYC QTYDSSGSAR
PL3#7-43_LC(deglyco2)     YGNSQRSSGV PDRFSGSKSG TSASLAITGL QAEDEADYYC QTYDSSGSAR
                          101                                                  150
PL3#7     LC(parental)    VVFGGGTKLT VL
PL3#7-19_LC(parental)     VVFGGGTKLT VL
PL3#7-19_LC(deglyco1)     VVFGGGTKLT VL
PL3#7-19_LC(deglyco2)     VVFGGGTKLT VL
PL3#7-19_LC(deglyco3)     VVFGGGTKLT VL
PL3#7-43_LC(parental)     VVFGGGTKLT VL
PL3#7-43_LC(deglyco1)     VVFGGGTKLT VL
PL3#7-43_LC(deglyco2)     VVFGGGTKLT VL
```

Figure 19A
Figure 19B
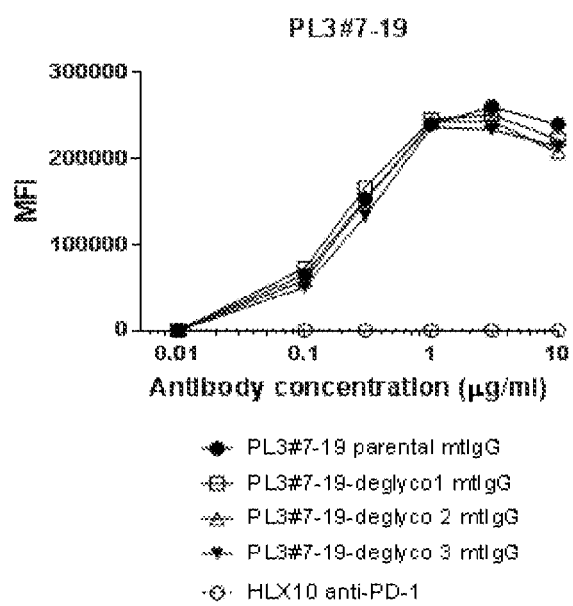
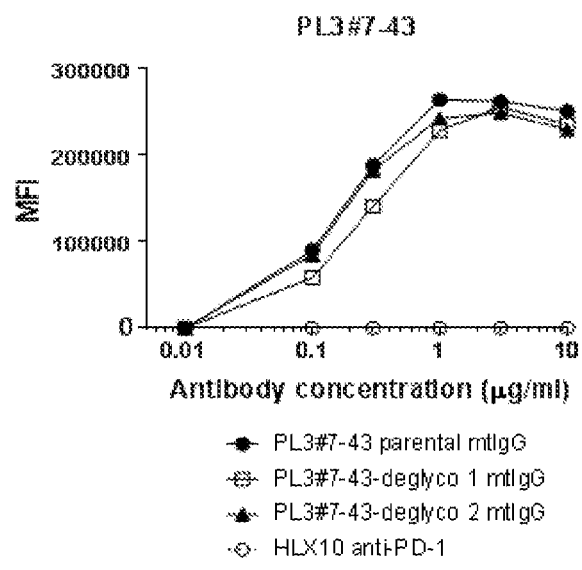

SEQUENCE LISTING

<160> NUMBER OF SEQ ID NOS: 145

<210> SEQ ID NO 1
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Ala Val Leu Thr Gln Pro Ser Ser Val Ser Gly Ala Pro Gly Gln
1               5                   10                  15

Arg Val Thr Ile Ser Cys Thr Gly Ser Ser Ser Asn Val Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
        180                 185                 190

His Arg Ser Tyr Ser Cys Gln Val Thr His Glu Gly Ser Thr Val Glu
    195                 200                 205

Lys Thr Val Ala Leu Thr Glu Cys
210                 215

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Val Thr Gln Pro Pro Ser Met Ser Ala Ala Pro Gly Gln
1               5                   10                  15

Asn Val Thr Ile Ser Cys Ser Gly Ser Ser Ser Tyr Ile Glu Ser Ser
            20                  25                  30

Tyr Val Ser Trp Tyr Gln Gln Leu Pro Gly Thr Ala Pro Arg Leu Leu
        35                  40                  45

Ile Tyr Asp Asp Asp Met Arg Pro Ser Gly Ile Pro Asp Arg Phe Ser
50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Glu Ile Trp Asp Ser Gly Leu
                85                  90                  95

Gly Gly Val Phe Gly Gly Gly Thr Lys Leu Thr Val Leu Ser Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Lys
            180                 185                 190

Ser Tyr Ser Cys Gln Val Thr His Glu Gly Ser Thr Val Glu Arg Thr
        195                 200                 205

Val Ala Leu Thr Glu Cys
    210

<210> SEQ ID NO 3
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Gln Ser Val Val Thr Gln Pro Pro Val Ser Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Pro Val Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
    195                 200                 205

Glu Lys Thr Val Ala Leu Thr Glu Cys
210                 215

<210> SEQ ID NO 4
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140
```

```
Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Leu Thr Glu Cys
    210                 215

<210> SEQ ID NO 5
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Leu Ser Ser Glu Leu Thr Gln Asp Pro Ala Val Ser Val Ala Leu Gly
1               5                   10                  15

Gln Thr Val Arg Ile Thr Cys Gln Gly Asp Ser Leu Arg Ser Tyr Tyr
            20                  25                  30

Val Ser Trp Tyr Gln Gln Lys Pro Gly Gln Ala Pro Val Leu Val Leu
        35                  40                  45

Tyr Gly Lys Asn Asn Arg Pro Ser Gly Ile Pro Asp Arg Phe Ser Gly
    50                  55                  60

Ser Ser Ser Gly Ser Thr Ala Ser Leu Thr Ile Thr Gly Ala Gln Ala
65                  70                  75                  80

Glu Asp Glu Ala Asp Tyr Tyr Cys Asn Ser Arg Asp Ser Thr Gly Asn
                85                  90                  95

Leu Leu Arg Val Phe Gly Gly Gly Thr Lys Leu Thr Val Leu Gly Gln
            100                 105                 110

Pro Lys Ala Ala Pro Ser Ile Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Leu Thr Glu Cys
    210                 215

<210> SEQ ID NO 6
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

```
Gln Ser Val Leu Thr Gln Pro Pro Ser Val Ser Gly Ala Pro Gly Gln
1               5                   10                  15

Arg Val Thr Ile Ser Cys Thr Arg Ser Ser Asn Ile Gly Ala Gly
            20                  25                  30

His Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                      55                  60

Ser Gly Ser Lys Ser Gly Thr Ser Ala Ser Leu Ala Ile Thr Gly Leu
65                  70                  75                  80

Gln Ala Glu Asp Gly Ala Asp Tyr Tyr Cys Gln Ser Tyr Asp Ser Ser
                85                  90                  95

Leu Thr Gly Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Leu Thr Glu Cys
    210                 215

<210> SEQ ID NO 7
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Ser Val Leu Thr Gln Pro Pro Ser Val Ser Gly Ala Pro Gly Gln
1               5                   10                  15

Arg Val Thr Ile Ser Cys Thr Gly Tyr Ser Ser Asn Ile Gly Ala Gly
            20                  25                  30

Tyr Asp Val His Trp Tyr Gln Gln His Leu Pro Gly Thr Ala Pro Lys Leu
            35                  40                  45

Leu Ile Tyr Gly Asn Ser Asn Arg Pro Ser Gly Val Pro Asp Arg Phe
50                      55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Val Ser Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
```

```
            130                 135                 140
Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Leu Thr Glu Cys
            210                 215

<210> SEQ ID NO 8
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Ile Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Gly Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ser Ser Gly Trp Leu Gly Val Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Ala Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 9
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Gln Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Thr Met Asn Trp Val Arg Gln Ala Pro Gly Lys Gly Leu Glu Trp Val
        35                  40                  45
Ser Ser Ile Ser Ser Gly Ser Asp Tyr Leu Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asn Glu Leu Arg Trp Tyr Pro Gln Ala Gly Ala Phe Asp Ile
            100                 105                 110
Trp Gly Gln Gly Thr Met Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Ala Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 10
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
```

```
            65                  70                  75                  80
        Met Glu Leu Ser Ser Leu Arg Ser Glu Asp Thr Ala Val Tyr Tyr Cys
                        85                  90                  95

Ala Arg Ser Arg Asp Gly Tyr Ser Phe Gly Ala Phe Asp Ile Trp Gly
                        100                 105                 110

Gln Gly Thr Leu Val Thr Val Ser Ser Ala Ser Thr Lys Gly Pro Ser
                        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
        145                 150                 155                 160

Ser Trp Asn Ser Gly Ala Leu Thr Ser Gly Val His Thr Phe Pro Ala
                        165                 170                 175

Val Leu Gln Ser Ser Gly Leu Tyr Ser Leu Ser Ser Val Val Thr Val
                        180                 185                 190

Pro Ser Ser Ser Leu Gly Thr Gln Thr Tyr Ile Cys Asn Val Asn His
                        195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
        225                 230                 235                 240

Gly Pro Ser Val Phe Leu Phe Pro Pro Lys Pro Lys Asp Thr Leu Met
                        245                 250                 255

Ile Ser Arg Thr Pro Glu Val Thr Cys Val Val Val Asp Val Ser His
                        260                 265                 270

Glu Asp Pro Glu Val Lys Phe Asn Trp Tyr Val Asp Gly Val Glu Val
                        275                 280                 285

His Asn Ala Lys Thr Lys Pro Arg Glu Glu Gln Tyr Ala Ser Thr Tyr
                        290                 295                 300

Arg Val Val Ser Val Leu Thr Val Leu His Gln Asp Trp Leu Asn Gly
        305                 310                 315                 320

Lys Glu Tyr Lys Cys Lys Val Ser Asn Lys Ala Leu Pro Ala Pro Ile
                        325                 330                 335

Glu Lys Thr Ile Ser Lys Ala Lys Gly Gln Pro Arg Glu Pro Gln Val
                        340                 345                 350

Tyr Thr Leu Pro Pro Ser Arg Glu Glu Met Thr Lys Asn Gln Val Ser
                        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
        385                 390                 395                 400

Val Leu Asp Ser Asp Gly Ser Phe Phe Leu Tyr Ser Lys Leu Thr Val
                        405                 410                 415

Asp Lys Ser Arg Trp Gln Gln Gly Asn Val Phe Ser Cys Ser Val Met
                        420                 425                 430

His Glu Ala Leu His Asn His Tyr Thr Gln Lys Ser Leu Ser Leu Ser
                        435                 440                 445

Pro Gly Lys
                450

<210> SEQ ID NO 11
<211> LENGTH: 451
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 11

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Asn Trp Val Arg Gln Ala Pro Gly Gln Gly Leu Glu Trp Val
        35                  40                  45

Gly Lys Ile Ile Pro Ile Leu Gly Ile Ala Asp Tyr Ala Gln Met Phe
    50                  55                  60

Lys Gly Arg Val Thr Ile Thr Ala Asp Lys Phe Thr Ser Thr Val Tyr
65                  70                  75                  80

Met Glu Leu Asn Ser Leu Arg Ser Glu Asp Thr Ala Val Tyr Tyr Cys
                85                  90                  95

Ala Arg Gly Gly Tyr Val Gly Tyr Leu Asn Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro

```
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 12
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Val Leu Asp Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 13
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ile Gly Ser Tyr Ser Phe Gly Ala Phe Asp Ile Trp Gly
            100                 105                 110

Gln Gly Thr Met Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Ala Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450

<210> SEQ ID NO 14
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Thr Ile Ser Trp Val Arg Gln Ala Pro Gly Gln Gly Leu Glu Trp Met
        35                  40                  45
Gly Arg Ile Ile Pro Ile Leu Gly Ile Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Arg Asp Gly Tyr Ser Phe Gly Ala Phe Asp Ile Trp Gly
```

100                 105                 110
Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 15
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
cagtctgtcg tgacgcagcc gccctcaatg tcagcggccc caggacagag agtcaccatc    60
tcctgctctg gaagcagctc ctacattgaa agttcttacg tcgggtggta ccagcaactc   120
ccaggaacag cccccagact cctcatttat gacgatgata tgcgaccctc agggatccct   180
gaccgattct ctggctccaa gtctggcacg tcagccaccc tggccatcac cggactccag   240
actggggacg aggccgatta ttactgcgag atatggcgga gcggcctggg aggcgtcttc   300
ggcggaggga ccaagctgac cgtccta                                       327
```

<210> SEQ ID NO 16
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Gln Ser Val Val Thr Gln Pro Pro Ser Met Ser Ala Ala Pro Gly Gln
1               5                   10                  15

Arg Val Thr Ile Ser Cys Ser Gly Ser Ser Tyr Ile Glu Ser Ser
            20                  25                  30

Tyr Val Gly Trp Tyr Gln Gln Leu Pro Gly Thr Ala Pro Arg Leu Leu
        35                  40                  45

Ile Tyr Asp Asp Asp Met Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Glu Ile Trp Arg Ser Gly Leu
                85                  90                  95

Gly Gly Val Phe Gly Gly Gly Thr Lys Leu Thr Val Leu
            100                 105
```

<210> SEQ ID NO 17
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
gaggttcagc tggtacaatc tgggggaggc ctggtcaagc ctgggggtc cctgagactc    60 tcctgtgcag cctctggatt caccttcagt agttatacta tgaactgggt ccgccaggct   120
ccagggaagg gctggagtg gtctcatcc attagtagtg gtagtgatta cttatactac   180
gcagactctg tgaagggccg attcaccatc tccagggaca cgccaagaa ctcactgtat   240 ctgcaaatga acagcctgag agccgaggac acggccgtgt attactgtgc gagaaacgaa   300
ctacggtggt atccacaagc aggtgctttt gatcgatggg gccaagggac aatggtcacc   360
gtctcaagc                                                           369
```

<210> SEQ ID NO 18
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
            35                  40                  45

Ser Ser Ile Ser Ser Gly Ser Asp Tyr Leu Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asn Glu Leu Arg Trp Tyr Pro Gln Ala Gly Ala Phe Asp Arg
            100                 105                 110

Trp Gly Gln Gly Thr Met Val Thr Val Ser Ser
            115                 120

<210> SEQ ID NO 19
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
cagtctgtcg tgacgcagcc gcccccagtg tctggggccc cagggcagag ggtcaccatc     60
tcctgcactg ggagcagctc aacatcgggg gcaggttatg atgtacactg gtaccagcag    120
cttccaggaa cagcccccaa actcctcatc tatggtaaca gcaatcggcc ctcaggggtc    180
cctgaccgat tctctggctc caagtctggc acctcagcct ccctggccat cactgggctc    240
caggctgagg atgaggctga ttattactgc cagacttatg acagcagcct gagtgcccgg    300
gtggtattcg gcggagggac caagctgacc gtccta                              336

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Ser Val Val Thr Gln Pro Pro Pro Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
            85                  90                  95

Leu Ser Ala Arg Val Val Phe Gly Gly Gly Thr Lys Leu Thr Val Leu
            100                 105                 110

<210> SEQ ID NO 21
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
caggtccagc tggtgcaatc tggggctgag gtgaagaagc ctgggtcctc ggtgaaggtc      60
tcctgcaagg cttctggagg caccttcagc agctatccga tcagctgggt gcgacaggcc     120
cctggacaag ggcttgagtg gataggaagg atcatcccta tccttgggat agcaaactac     180
gcacagaagt tccagggcag agtcacgatt accgcggaca atccacgag cacagcctac      240 atggagctga gcagcctgag atctgaggac acggccgtgt attactgtgc gaggtctaga     300
gatggctacg cttttggtgc ttttgatatc tggggccaag gaaccctggt caccgtctca     360
agc                                                                   363
```

<210> SEQ ID NO 22
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Pro Ile Ser Trp Val Arg Gln Ala Pro Gly Gln Gly Leu Glu Trp Ile
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Asp Gly Tyr Ala Phe Gly Ala Phe Asp Ile Trp Gly
            100                 105                 110

Gln Gly Thr Leu Val Thr Val Ser Ser
        115                 120
```

<210> SEQ ID NO 23
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
cagtctgtcg tgacgcagcc gccccagtg tctggggccc cagggcagag ggtcaccatc      60
tcctgcactg ggagcagctc caacatcggg gggggttatg atgtacactg gtaccagcag    120
cttccaggaa cagccccaa actcctcatc tatggtaaca gcacgcggcc ctcagggtc       180 cctgaccgat tctctggctc caagtctggc acctcagcct ccctggccat cactgggctc    240
```

```
caggctgagg atgaggctga ttattactgc cagacttatg acagcagcct gagtgccacg    300
gtggtattcg gcggagggac caagctgacc gtccta                              336
```

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 24

```
Gln Ser Val Val Thr Gln Pro Pro Val Ser Gly Ala Pro Gly Gln
1               5                   10                  15

Arg Val Thr Ile Ser Cys Thr Gly Ser Ser Ser Asn Ile Gly Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Thr Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
                85                  90                  95

Leu Ser Ala Thr Val Val Phe Gly Gly Gly Thr Lys Leu Thr Val Leu
            100                 105                 110
```

<210> SEQ ID NO 25
<211> LENGTH: 363
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 25

```
caggtccagc tggtgcaatc tggggctgag gtgaagaagc ctgggtcctc ggtgaaggtc    60
tcctgcaagg cttctggagg caccttcagc agctatccga tcagctgggt gcgacaggcc   120
cctggacaag gcttgagtg gatgggaagg atcatcccta tccttggtat agcaaactac   180
gcacagaagt tccagggcag agtcacgatt accgcggaca atccacgag cacagcctac   240 atggagctga gcagcctgag atctgaggac acggccgtgt attactgtgc gaggtctaga   300
gatggctacg cttttggtgc ttttgatgtg tggggccaag aaccctggt caccgtctca   360 agc                                                                 363
```

<210> SEQ ID NO 26
<211> LENGTH: 121
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 26

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30
```

```
Pro Ile Ser Trp Val Arg Gln Ala Pro Gly Gln Gly Leu Glu Trp Met
         35                  40                  45

Gly Arg Ile Ile Pro Ile Leu Gly Ile Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Asp Gly Tyr Ala Phe Gly Ala Phe Asp Val Trp Gly
            100                 105                 110

Gln Gly Thr Leu Val Thr Val Ser Ser
            115                 120
```

<210> SEQ ID NO 27
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
cagtctgtcg tgacgcagcc gcccccagtg tctggggccc cagggcagag ggtcaccatc    60
tcctgcactg ggagcagctc caacgtgggg gcaggttatg atgtacactg gtaccagcag   120
cttccaggaa cagcccccaa actcctcatc tatggtaaca gcaatcggtc ttcagggggtc   180 cctgaccgat tctctggctc caagtctggc acctcagcct ccctggccat cactgggctc   240
caggctgagg atgaggctga ttattactgc cagacttatg acagcagcgg gagtgcccgg   300
gtggtattcg gcggagggac caagctgacc gtccta                             336
```

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Gln Ser Val Val Thr Gln Pro Pro Val Ser Gly Ala Pro Gly Gln
  1               5                  10                  15

Arg Val Thr Ile Ser Cys Thr Gly Ser Ser Ser Asn Val Gly Ala Gly
             20                  25                  30

Tyr Asp Val His Trp Tyr Gln Gln Leu Pro Gly Thr Ala Pro Lys Leu
         35                  40                  45

Leu Ile Tyr Gly Asn Ser Asn Arg Ser Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Thr Tyr Asp Ser Ser
                 85                  90                  95

Gly Ser Ala Arg Val Val Phe Gly Gly Gly Thr Lys Leu Thr Val Leu
            100                 105                 110
```

<210> SEQ ID NO 29
<211> LENGTH: 363
<212> TYPE: DNA
<213> ORGANISM: Artificial Sequence
<220> FEATURE:

-continued

<223> OTHER INFORMATION: Description of Artificial Sequence: Synthetic
      polynucleotide

<400> SEQUENCE: 29
caggtccagc tggtgcaatc tggggctgag gtgaagaagc ctgggtcctc ggtgaaggtc    60
tcctgcaagg cttctggagg caccttcagc agctatccga tcagctgggt gcgacaggcc   120
cctggacaag ggcttgagtg gatgggaagg atcatcccta tccttggtat agcaaactac   180
gcacagaagt tccagggcag agtcacgatt accgcggaca atccacgag cacagcctac   240 atggagctga gcagcctgag atctgaggac acggccgtgt attactgtgc gaggtctaga   300
ccgggctacg cttttggtgc ttttgatatc tggggccaag gaaccctggt caccgtctca   360
agc                                                                 363

<210> SEQ ID NO 30
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Pro Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Pro Gly Tyr Ala Phe Gly Ala Phe Asp Ile Trp Gly
            100                 105                 110

Gln Gly Thr Leu Val Thr Val Ser Ser
        115                 120

<210> SEQ ID NO 31
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
cagtctgtcg tgacgcagcc gccccagtg tctggggccc cagggcagag ggtcaccatc    60
tcctgcactg ggagcagctc caacatcggg cagggttatg atgtacactg gtaccagcag   120
cttccaggaa cagcccccaa actcctcatc tatgctaaca gcaatcggcc ctcaggggtc   180
cctgaccgat tctctggctc caagtctggc acctcagcct ccctggccat cactgggctc   240
caggctgagg atgaggctga ttattactgc cagacttatg acagcagcct gagtgcccgg   300
gtggtattcg gcggagggac caagctgacc gtccta                             336

<210> SEQ ID NO 32

<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Ser Val Val Thr Gln Pro Pro Val Ser Gly Ala Pro Gly Gln
1               5                   10                  15

Arg Val Thr Ile Ser Cys Thr Gly Ser Ser Asn Ile Gly Gln Gly
                20                  25                  30

Tyr Asp Val His Trp Tyr Gln Gln Leu Pro Gly Thr Ala Pro Lys Leu
            35                  40                  45

Leu Ile Tyr Ala Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
                85                  90                  95

Leu Ser Ala Arg Val Val Phe Gly Gly Gly Thr Lys Leu Thr Val Leu
            100                 105                 110

<210> SEQ ID NO 33
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
caggtccagc tggtgcaatc tgggctgag gtgaagaagc ctgggtcctc ggtgaaggtc      60
tcctgcaagg cttctggagg caccttcagc agctatccga tcagctgggt gcgacaggcc    120
cctggacaag ggcttgagtg gatgggaagg atcatcccta tccttggtat agcagattac    180
gcacagaagt tccagggcag agtcacgatt accgcggaca atccacgag cacagcctac    240 atggagctga gcagcctgag atctgaggac acggccgtgt attactgtgc gaggtctaga    300
ccgggctacg cttttggtgc ttttgatatc tggggccaag aaccctggt caccgtctca    360 agc                                                                 363

<210> SEQ ID NO 34
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Pro Ile Ser Trp Val Arg Gln Ala Pro Gly Gln Gly Leu Glu Trp Met
            35                  40                  45

Gly Arg Ile Ile Pro Ile Leu Gly Ile Ala Asp Tyr Ala Gln Lys Phe
50                  55                  60

Gln Gly Arg Val Thr Ile Thr Ala Asp Lys Ser Thr Ser Thr Ala Tyr

```
                65                  70                  75                  80
Met Glu Leu Ser Ser Leu Arg Ser Glu Asp Thr Ala Val Tyr Tyr Cys
                        85                  90                  95
Ala Arg Ser Arg Pro Gly Tyr Ala Phe Gly Ala Phe Asp Ile Trp Gly
                100                 105                 110
Gln Gly Thr Leu Val Thr Val Ser Ser
        115                 120
```

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Thr Gly Ser Ser Ser Asn Val Gly Ala Gly Tyr Asp Val His
1               5                   10
```

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Ser Gly Ser Ser Ser Tyr Ile Glu Ser Ser Tyr Val Ser
1               5                   10
```

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Thr Gly Ser Ser Ser Asn Ile Gly Ala Gly Tyr Asp Val His
1               5                   10
```

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gln Gly Asp Ser Leu Arg Ser Tyr Tyr Val Ser
1               5                   10
```

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Thr Arg Ser Ser Ser Asn Ile Gly Ala Gly His Asp Val His
```

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Gly Tyr Ser Ser Asn Ile Gly Ala Gly Tyr Asp Val His
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Asn Ser Asn Arg Pro Ser
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Asp Asp Met Arg Pro Ser
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Lys Asn Asn Arg Pro Ser
1               5

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ser Tyr Asp Ser Ser Leu Ser Gly Trp Val
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Glu Ile Trp Asp Ser Gly Leu Gly Gly Val
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ser Tyr Asp Ser Ser Leu Ser Ala Pro Val Val
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ser Tyr Asp Ser Ser Leu Ser Gly Gly Val
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asn Ser Arg Asp Ser Thr Gly Asn Leu Leu Arg Val
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ser Tyr Asp Ser Ser Leu Thr Gly Val Val
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ser Tyr Asp Asn Ser Leu Ser Val Ser Val
1               5                   10

<210> SEQ ID NO 51

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Tyr Ala Ile Ser
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Tyr Thr Met Asn
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Tyr Thr Ile Ser
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Tyr Thr Ile Asn
1               5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ile Ile Pro Ile Leu Gly Ile Ala Asn Tyr Ala Gln Lys Phe Gln
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 56

Ser Ile Ser Ser Gly Ser Asp Tyr Leu Tyr Tyr Ala Asp Ser Val Lys
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Ile Ile Pro Ile Leu Gly Ile Ala Asp Tyr Ala Gln Met Phe Lys
1               5                   10                  15

Gly

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ile Ile Pro Ile Phe Gly Thr Ala Asn Tyr Ala Gln Lys Phe Gln
1               5                   10                  15

Gly

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Gly Ser Ser Gly Trp Leu Gly Val Leu Asp Tyr
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asn Glu Leu Arg Trp Tyr Pro Gln Ala Gly Ala Phe Asp Ile
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Arg Asp Gly Tyr Ser Phe Gly Ala Phe Asp Ile
```

```
1               5                  10
```

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Gly Gly Tyr Val Gly Tyr Leu Asn Ala Phe Asp Ile
1               5                  10
```

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Glu Gly Val Leu Asp Ala Phe Asp Ile
1               5
```

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Gly Ile Gly Ser Tyr Ser Phe Gly Ala Phe Asp Ile
1               5                  10
```

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Ser Gly Ser Ser Ser Tyr Ile Glu Ser Ser Tyr Val Gly
1               5                  10
```

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Thr Gly Ser Ser Ser Asn Ile Gly Gly Gly Tyr Asp Val His
1               5                  10
```

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Thr Gly Ser Ser Ser Asn Ile Gly Gln Gly Tyr Asp Val His
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Asn Ser Thr Arg Pro Ser
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Asn Ser Asn Arg Ser Ser
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Asn Ser Asn Arg Pro Ser
1               5

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Ile Trp Arg Ser Gly Leu Gly Gly Val
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Thr Tyr Asp Ser Ser Leu Ser Ala Arg Val Val
1               5                   10

<210> SEQ ID NO 73

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Thr Tyr Asp Ser Ser Leu Ser Ala Thr Val Val
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Thr Tyr Asp Ser Ser Gly Ser Ala Arg Val Val
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Tyr Pro Ile Ser
1               5

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ile Ile Pro Ile Leu Gly Ile Ala Asp Tyr Ala Gln Lys Phe Gln
1               5                   10                  15

Gly

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asn Glu Leu Arg Trp Tyr Pro Gln Ala Gly Ala Phe Asp Arg
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 78

Ser Arg Asp Gly Tyr Ala Phe Gly Ala Phe Asp Ile
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Arg Asp Gly Tyr Ala Phe Gly Ala Phe Asp Val
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Arg Pro Gly Tyr Ala Phe Gly Ala Phe Asp Ile
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Arg Pro Gly Tyr Ala Phe Gly Ala Phe Asp Ile
1               5                   10

<210> SEQ ID NO 82
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
cagtctgtcg tgacgcagcc gccctcaatg tcagcggccc caggacagag ggtcaccatc      60
tcctgctctg gagttagctc ctacattgaa agttcttatg tctcctggta ccagcaactc     120
ccaggaacag ccccccagact cctcatttat gacgatgata tgcgaccctc agggatccct    180
gaccgattct ctggctccaa gtctggcacg tcagccaccc tggccatcac cggactccag     240
actggggacg aggccgatta ttactgcaag atatgggata gcggcctggg aggcgtcttc     300
ggcggaggga ccaagctgac cgtccta                                         327

<210> SEQ ID NO 83
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Ser Val Val Thr Gln Pro Pro Ser Met Ser Ala Ala Pro Gly Gln
1               5                   10                  15

Arg Val Thr Ile Ser Cys Ser Gly Val Ser Ser Tyr Ile Glu Ser Ser
            20                  25                  30

Tyr Val Ser Trp Tyr Gln Gln Leu Pro Gly Thr Ala Pro Arg Leu Leu
        35                  40                  45

Ile Tyr Asp Asp Met Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Lys Ile Trp Asp Ser Gly Leu
                85                  90                  95

Gly Gly Val Phe Gly Gly Gly Thr Lys Leu Thr Val Leu
            100                 105

<210> SEQ ID NO 84
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
gaggttcagc tggtacaatc tgggggaggc ctggtcaagc ctggggggtc cctgagactc      60
tcctgtgcag cctctggatt caccttcagt agttatacta tgaactgggt ccgccaggct     120
ccagggaagg gcctggagtg ggtctcatcc attagtagtg gtagtgatta cttatactac     180
gcagactctg tgaagggccg attcaccatc tccagggaca acgccaagaa ctcactgtat     240
ctgcaaatga acagcctgag agccgaggac acggccgtgt attactgtgc gagaaacgaa     300
ctacggtggt atccacttgc aggtgctttt gatatctggg gccaagggac aatggtcacc     360
gtctcaagc                                                              369

<210> SEQ ID NO 85
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Gly Ser Asp Tyr Leu Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Glu Leu Arg Trp Tyr Pro Leu Ala Gly Ala Phe Asp Ile
            100                 105                 110

Trp Gly Gln Gly Thr Met Val Thr Val Ser Ser
        115                 120

<210> SEQ ID NO 86
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
cagtctgtcg tgacgcagcc gccctcaatg tcagcggccc caggacagag ggtcaccatc      60
tcctgcagtg gaagcagctc ctacattgaa agttcttatg tctcatggta ccagcaactc     120
ccaggaacag cccccagact cctcatttat gacgatgata tgcgaccctc agggatccct     180
gaccgattct ctggctccaa gtctggcacg tcagccaccc tggccatcac cggactccag     240
actggggacg aggccgatta ttactgcgag atatgggata gccggctggg aggcgtcttc     300
ggcggaggga ccaagctgac cgtccta                                         327

<210> SEQ ID NO 87
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Ser Val Val Thr Gln Pro Pro Ser Met Ser Ala Ala Pro Gly Gln
1               5                  10                  15

Arg Val Thr Ile Ser Cys Ser Gly Ser Ser Ser Tyr Ile Glu Ser Ser
            20                  25                  30

Tyr Val Ser Trp Tyr Gln Gln Leu Pro Gly Thr Ala Pro Arg Leu Leu
        35                  40                  45

Ile Tyr Asp Asp Asp Met Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Glu Ile Trp Asp Ser Arg Leu
                85                  90                  95

Gly Gly Val Phe Gly Gly Gly Thr Lys Leu Thr Val Leu
            100                 105

<210> SEQ ID NO 88
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
gaggttcagc tggtacaatc tggggaggc ctggtcaagc ctgggggtc cctgagactc       60 tcctgtgcag cctctggatt caccttcagt agttatacta tgaactgggt ccgccaggct    120
ccagggaagg gctggagtg gtctcatcc attagtagtg gtagtgatta cttatactac     180
gcagactctg tgaagggccg attcaccatc tccagggaca cgccaagaa ctcactgtat    240 ctgcaaatga acagcctgag agccgaggac acggccgtgt attactgtgc gagaaacgaa    300

```
ctacggtggt atccatttgc aggtgctttt gatatttggg gccaagggac aatggtcacc    360
gtctcaagc                                                            369
```

<210> SEQ ID NO 89
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Gly Ser Asp Tyr Leu Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Glu Leu Arg Trp Tyr Pro Phe Ala Gly Ala Phe Asp Ile
            100                 105                 110

Trp Gly Gln Gly Thr Met Val Thr Val Ser Ser
        115                 120
```

<210> SEQ ID NO 90
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
cagtctgtcg tgacgcagcc gccctcaatg tcagcggccc caggacagag ggtcaccatc     60
tcctgctctg gaagcagctc ctacattacg agttcttatg tctcctggta ccagcaactc    120
ccaggaacag cccccagact cctcatttat gacgatgata tgcgaccctc agggatccct    180
gaccgattct ctggctccaa gtctggcacg tcagccaccc tggccatcac cggactccag    240
actggggacg aggccgatta ttactgcaag atatgggata cggcctggg aggcgtcttc    300 ggcggaggga ccaagctgac cgtccta                                        327
```

<210> SEQ ID NO 91
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Gln Ser Val Val Thr Gln Pro Pro Ser Met Ser Ala Ala Pro Gly Gln
1               5                   10                  15

Arg Val Thr Ile Ser Cys Ser Gly Ser Ser Ser Tyr Ile Thr Ser Ser
            20                  25                  30
```

```
Tyr Val Ser Trp Tyr Gln Gln Leu Pro Gly Thr Ala Pro Arg Leu Leu
            35                  40                  45

Ile Tyr Asp Asp Asp Met Arg Pro Ser Gly Ile Pro Asp Arg Phe Ser
 50                  55                  60

Gly Ser Lys Ser Gly Thr Ser Ala Thr Leu Ala Ile Thr Gly Leu Gln
 65                  70                  75                  80

Thr Gly Asp Glu Ala Asp Tyr Tyr Cys Lys Ile Trp Asp Ser Gly Leu
                 85                  90                  95

Gly Gly Val Phe Gly Gly Gly Thr Lys Leu Thr Val Leu
            100                 105

<210> SEQ ID NO 92
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gaggttcagc tggtacaatc tgggggaggc ctggtcaagc ctggggggtc cctgagactc     60
tcctgtgcag cctctggatt caccttcagt agttatacta tgaactgggt ccgccaggct    120
ccagggaagg gcctggagtg ggtctcatcc attagtagtg gtagtgatta cttatactac    180
gcagactctg tgaagggccg attcaccatc tccagggaca acgccaagaa ctcactgtat    240
ctgcaaatga acagcctgag agccgaggac acggccgtgt attactgtgc gagaaacgaa    300
ctacggtggt atccaaaggc aggtgctttt gatatatggg gccaagggac aatggtcacc    360
gtctcaagc                                                            369

<210> SEQ ID NO 93
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Val Gln Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Gly Ser Asp Tyr Leu Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asn Glu Leu Arg Trp Tyr Pro Lys Ala Gly Ala Phe Asp Ile
            100                 105                 110

Trp Gly Gln Gly Thr Met Val Thr Val Ser Ser
        115                 120

<210> SEQ ID NO 94
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Gly Val Ser Ser Tyr Ile Glu Ser Ser Tyr Val Ser
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Lys Ile Trp Asp Ser Gly Leu Gly Gly Val
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asn Glu Leu Arg Trp Tyr Pro Leu Ala Gly Ala Phe Asp Ile
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Gly Ser Ser Ser Tyr Ile Glu Ser Ser Tyr Val Ser
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Ile Trp Asp Ser Arg Leu Gly Gly Val
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asn Glu Leu Arg Trp Tyr Pro Phe Ala Gly Ala Phe Asp Ile
```

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Gly Ser Ser Ser Tyr Ile Thr Ser Ser Tyr Val Ser
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asn Glu Leu Arg Trp Tyr Pro Lys Ala Gly Ala Phe Asp Ile
1               5                   10

<210> SEQ ID NO 102
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
cagtctgtcg tgacgcagcc gcccccagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tatggtaaca gcaggcggcc ctcaggggtc     180
cctgaccgat tctctggctc caagtctggc acctcagcct ccctggccat cactgggctc     240
caggctgagg atgaggctga ttattactgc cagacctatg acagcagcct gagtcgtccc     300
gtggtattcg gcggagggac caagctgacc gtccta                              336

<210> SEQ ID NO 103
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Ser Val Val Thr Gln Pro Pro Pro Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Arg Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
            85                  90                  95

Leu Ser Arg Pro Val Val Phe Gly Gly Gly Thr Lys Leu Thr Val Leu
        100                 105                 110

<210> SEQ ID NO 104
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
caggtccagc tggtgcaatc tggggctgag gtgaagaagc ctgggtcctc ggtgaaggtc      60
tcctgcaagg cttctggagg caccttcagc agctatagga tcagctgggt gcgacaggcc     120
cctggacaag ggcttgagtg gatgggaagg atcatcccta tccttggtat agcaaactac     180
gcacagaagt tccagggcag agtcacgatt accgcggaca atccacgag cacagcctac      240 atggagctga gcagcctgag atctgaggac acggccgtgt attactgtgc gaggtctaga     300
gatggctaca gtgtgggtgc ttttgattcg tggggccaag aaccctggt caccgtctca      360 agc                                                                   363

<210> SEQ ID NO 105
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Arg Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Asp Gly Tyr Ser Val Gly Ala Phe Asp Ser Trp Gly
            100                 105                 110

Gln Gly Thr Leu Val Thr Val Ser Ser
        115                 120

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Asn Ser Arg Arg Pro Ser
1               5

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Thr Tyr Asp Ser Ser Leu Ser Arg Pro Val Val
1               5                   10

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser Tyr Arg Ile Ser
1               5

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Arg Asp Gly Tyr Ser Val Gly Ala Phe Asp Ser
1               5                   10

<210> SEQ ID NO 110
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
cagtctgtcg tgacgcagcc gcccccagtg tctggggccc cagggcagag ggtcaccatc      60
tcctgcactg ggagcagctc caacatcggg gggggttatg atgtacactg gtaccagcag     120
cttccaggaa cagcccccaa actcctcatc tatggtaaca gcaatcggcc ctcagggggtc    180 cctgaccgat tctctggctc caagtctggc acctcagcct ccctggccat cactgggctc     240
caggctgagg atgaggctga ttattactgc cagacttatg acagcagcct gagtgccacg     300
gtggtattcg gcggagggac caagctgacc gtccta                               336

<210> SEQ ID NO 111
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Ser Val Val Thr Gln Pro Pro Pro Val Ser Gly Ala Pro Gly Gln
1               5                   10                  15

Arg Val Thr Ile Ser Cys Thr Gly Ser Ser Asn Ile Gly Gly Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
                85                  90                  95

Leu Ser Ala Thr Val Val Phe Gly Gly Gly Thr Lys Leu Thr Val Leu
            100                 105                 110

<210> SEQ ID NO 112
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
cagtctgtcg tgacgcagcc gcccccagtg tctggggccc cagggcagag ggtcaccatc    60
tcctgcactg ggagcagctc caacatcggg ggggttatg atgtacactg gtaccagcag   120
cttccaggaa cagcccccaa actcctcatc tatggtcaga gcacgcggcc ctcaggggtc   180
cctgaccgat tctctggctc caagtctggc acctcagcct ccctggccat cactgggctc   240
caggctgagg atgaggctga ttattactgc cagacttatg acagcagcct gagtgccacg   300
gtggtattcg gcggagggac caagctgacc gtccta                             336

<210> SEQ ID NO 113
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Ser Val Val Thr Gln Pro Pro Pro Val Ser Gly Ala Pro Gly Gln
1               5                   10                  15

Arg Val Thr Ile Ser Cys Thr Gly Ser Ser Asn Ile Gly Gly Gly
            20                  25                  30

Tyr Asp Val His Trp Tyr Gln Gln Leu Pro Gly Thr Ala Pro Lys Leu
        35                  40                  45

Leu Ile Tyr Gly Gln Ser Thr Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
                85                  90                  95

Leu Ser Ala Thr Val Val Phe Gly Gly Gly Thr Lys Leu Thr Val Leu
            100                 105                 110

<210> SEQ ID NO 114
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
cagtctgtcg tgacgcagcc gcccccagtg tctggggccc cagggcagag ggtcaccatc    60
tcctgcactg ggagcagctc caacatcggg gggggttatg atgtacactg gtaccagcag   120
cttccaggaa cagcccccaa actcctcatc tatggtaaca gccaacggcc ctcaggggtc   180
cctgaccgat tctctggctc caagtctggc acctcagcct ccctggccat cactgggctc   240
caggctgagg atgaggctga ttattactgc cagacttatg acagcagcct gagtgccacg   300
gtggtattcg gcggagggac caagctgacc gtccta                             336
```

<210> SEQ ID NO 115
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Gln Ser Val Val Thr Gln Pro Pro Val Ser Gly Ala Pro Gly Gln
1               5                   10                  15

Arg Val Thr Ile Ser Cys Thr Gly Ser Ser Ser Asn Ile Gly Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Gln Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
                85                  90                  95

Leu Ser Ala Thr Val Val Phe Gly Gly Gly Thr Lys Leu Thr Val Leu
            100                 105                 110
```

<210> SEQ ID NO 116
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

```
cagtctgtcg tgacgcagcc gcccccagtg tctggggccc cagggcagag ggtcaccatc    60
tcctgcactg ggagcagctc caacgtgggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagacttatg acagcagcgg gagtgcccgg   300
gtggtattcg gcggagggac caagctgacc gtccta                             336
```

<210> SEQ ID NO 117
<211> LENGTH: 112
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 117

Gln Ser Val Val Thr Gln Pro Pro Val Ser Gly Ala Pro Gly Gln
1               5                   10                  15

Arg Val Thr Ile Ser Cys Thr Gly Ser Ser Asn Val Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
            85                  90                  95

Gly Ser Ala Arg Val Val Phe Gly Gly Gly Thr Lys Leu Thr Val Leu
            100                 105                 110

<210> SEQ ID NO 118
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 118
cagtctgtcg tgacgcagcc gcccccagtg tctggggccc cagggcagag ggtcaccatc      60
tcctgcactg ggagcagctc caacgtgggg gcaggttatg atgtacactg gtaccagcag     120
cttccaggaa cagcccccaa actcctcatc tatggtaaca gccaacggtc ttcagggtc      180 cctgaccgat tctctggctc caagtctggc acctcagcct ccctggccat cactgggctc     240
caggctgagg atgaggctga ttattactgc cagacttatg acagcagcgg gagtgcccgg     300
gtggtattcg gcggagggac caagctgacc gtccta                               336

<210> SEQ ID NO 119
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 119

Gln Ser Val Val Thr Gln Pro Pro Val Ser Gly Ala Pro Gly Gln
1               5                   10                  15

Arg Val Thr Ile Ser Cys Thr Gly Ser Ser Asn Val Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Gln Arg Ser Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
            85                  90                  95

Gly Ser Ala Arg Val Val Phe Gly Gly Gly Thr Lys Leu Thr Val Leu

```
                100               105               110
```

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ile Gly Ala Gly Tyr Asp
1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Asn Ser Asn Arg Pro
1               5

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Asn Ser Arg Arg Pro
1               5

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Tyr Asp Ser Ser Leu Ser Ala Pro Val Val
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Tyr Asp Ser Ser Leu Ser Arg Pro Val Val
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Thr Tyr Asp Ser Ser Leu Ser Ala Arg Val Val
1               5                   10

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ile Pro Ile Leu Gly Ile Ala Asn
1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ile Gly Gly Gly Tyr Asp
1               5

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Val Gly Ala Gly Tyr Asp
1               5

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ile Gly Gln Gly Tyr Asp
1               5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Asn Ser Thr Arg Pro
1               5

<210> SEQ ID NO 131

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Asn Ser Asn Arg Ser
1               5

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Asn Ser Asn Arg Pro
1               5

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Tyr Asp Ser Ser Leu Ser Ala Thr Val Val
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Tyr Asp Ser Ser Gly Ser Ala Arg Val Val
1               5                   10

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ile Pro Ile Leu Gly Ile Ala Asp
1               5

<210> SEQ ID NO 136
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136
```

Gln Ser Val Val Thr Gln Pro Pro Ser Met Ser Ala Pro Gly Gln
1               5                   10                  15

Arg Val Thr Ile Ser Cys Ser Gly Ser Ser Ser Tyr Ile Glu Ser Ser
            20                  25                  30

Tyr Val Gly Trp Tyr Gln Gln Leu Pro Gly Thr Ala Pro Arg Leu Leu
            35                  40                  45

Ile Tyr Asp Asp Asp Met Arg Pro Ser Gly Ile Pro Asp Arg Phe Ser
        50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Glu Ile Trp Arg Ser Gly Leu
                85                  90                  95

Gly Gly Val Phe Gly Gly Gly Thr Lys Leu Thr Val Leu Ser Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Lys
            180                 185                 190

Ser Tyr Ser Cys Gln Val Thr His Glu Gly Ser Thr Val Glu Arg Thr
            195                 200                 205

Val Ala Leu Thr Glu Cys
    210

<210> SEQ ID NO 137
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Ser Val Val Thr Gln Pro Pro Pro Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
                85                  90                  95

Leu Ser Ala Arg Val Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
130                 135                 140

```
Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
        195                 200                 205

Glu Lys Thr Val Ala Leu Thr Glu Cys
        210                 215
```

<210> SEQ ID NO 138
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Gln Ser Val Val Thr Gln Pro Pro Val Ser Gly Ala Pro Gly Gln
1               5                   10                  15

Arg Val Thr Ile Ser Cys Thr Gly Ser Ser Ser Asn Ile Gly Gly Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Thr Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
                85                  90                  95

Leu Ser Ala Thr Val Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
        195                 200                 205

Glu Lys Thr Val Ala Leu Thr Glu Cys
        210                 215
```

<210> SEQ ID NO 139
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Ser Val Val Thr Gln Pro Pro Val Ser Gly Ala Pro Gly Gln
1               5                   10                  15

Arg Val Thr Ile Ser Cys Thr Gly Ser Ser Asn Val Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Ser Gly Val Pro Asp Arg Phe
50                      55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
                85                  90                  95

Gly Ser Ala Arg Val Val Phe Gly Gly Gly Thr Lys Leu Thr Val Leu
                100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
                195                 200                 205

Glu Lys Thr Val Ala Leu Thr Glu Cys
210                 215

<210> SEQ ID NO 140
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Ser Val Val Thr Gln Pro Pro Val Ser Gly Ala Pro Gly Gln
1               5                   10                  15

Arg Val Thr Ile Ser Cys Thr Gly Ser Ser Asn Ile Gly Gln Gly
                20                  25                  30

Tyr Asp Val His Trp Tyr Gln Gln Leu Pro Gly Thr Ala Pro Lys Leu
            35                  40                  45

Leu Ile Tyr Ala Asn Ser Asn Arg Pro Ser Gly Val Pro Asp Arg Phe
50                      55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Tyr Asp Ser Ser
                85                  90                  95

Leu Ser Ala Arg Val Val Phe Gly Gly Gly Thr Lys Leu Thr Val Leu
                100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp

```
            130                 135                 140
Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
        195                 200                 205

Glu Lys Thr Val Ala Leu Thr Glu Cys
    210                 215

<210> SEQ ID NO 141
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Gly Ser Asp Tyr Leu Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Glu Leu Arg Trp Tyr Pro Gln Ala Gly Ala Phe Asp Arg
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

```
Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Ala Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 142
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Pro Ile Ser Trp Val Arg Gln Ala Pro Gly Gln Gly Leu Glu Trp Ile
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Asp Gly Tyr Ala Phe Gly Ala Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 143
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Pro Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr

```
            65                  70                  75                  80
        Met Glu Leu Ser Ser Leu Arg Ser Glu Asp Thr Ala Val Tyr Tyr Cys
                        85                  90                  95

Ala Arg Ser Arg Asp Gly Tyr Ala Phe Gly Ala Phe Asp Val Trp Gly
                    100                 105                 110

Gln Gly Thr Leu Val Thr Val Ser Ala Ser Thr Lys Gly Pro Ser
                    115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
        145                 150                 155                 160

Ser Trp Asn Ser Gly Ala Leu Thr Ser Gly Val His Thr Phe Pro Ala
                        165                 170                 175

Val Leu Gln Ser Ser Gly Leu Tyr Ser Leu Ser Ser Val Val Thr Val
                    180                 185                 190

Pro Ser Ser Ser Leu Gly Thr Gln Thr Tyr Ile Cys Asn Val Asn His
                    195                 200                 205

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
        225                 230                 235                 240

Gly Pro Ser Val Phe Leu Phe Pro Pro Lys Pro Lys Asp Thr Leu Met
                        245                 250                 255

Ile Ser Arg Thr Pro Glu Val Thr Cys Val Val Val Asp Val Ser His
                    260                 265                 270

Glu Asp Pro Glu Val Lys Phe Asn Trp Tyr Val Asp Gly Val Glu Val
                    275                 280                 285

His Asn Ala Lys Thr Lys Pro Arg Glu Glu Gln Tyr Ala Ser Thr Tyr
            290                 295                 300

Arg Val Val Ser Val Leu Thr Val Leu His Gln Asp Trp Leu Asn Gly
        305                 310                 315                 320

Lys Glu Tyr Lys Cys Lys Val Ser Asn Lys Ala Leu Pro Ala Pro Ile
                        325                 330                 335

Glu Lys Thr Ile Ser Lys Ala Lys Gly Gln Pro Arg Glu Pro Gln Val
                    340                 345                 350

Tyr Thr Leu Pro Pro Ser Arg Glu Glu Met Thr Lys Asn Gln Val Ser
                    355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
        385                 390                 395                 400

Val Leu Asp Ser Asp Gly Ser Phe Phe Leu Tyr Ser Lys Leu Thr Val
                        405                 410                 415

Asp Lys Ser Arg Trp Gln Gln Gly Asn Val Phe Ser Cys Ser Val Met
                    420                 425                 430

His Glu Ala Leu His Asn His Tyr Thr Gln Lys Ser Leu Ser Leu Ser
                    435                 440                 445

Pro Gly Lys
            450

<210> SEQ ID NO 144
<211> LENGTH: 451
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 144

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Pro Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Pro Gly Tyr Ala Phe Gly Ala Phe Asp Ile Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
```

```
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 145
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Pro Ile Ser Trp Val Arg Gln Ala Pro Gly Gln Gly Leu Glu Trp Met
            35                  40                  45

Gly Arg Ile Ile Pro Ile Leu Gly Ile Ala Asp Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Pro Gly Tyr Ala Phe Gly Ala Phe Asp Ile Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285
```

```
His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450
```

ANTI-PD-L1 ANTIBODIES AND VARIANTS

CROSS-REFERENCE TO RELATED APPLICATIONS

This application is a continuation application of U.S. application Ser. No. 16/380,493, filed on Apr. 10, 2019, which is a continuation application of a PCT International Application No. PCT/US2017/056689, filed on Oct. 14, 2017, which claims the benefit and priority to U.S. Provisional Patent Application No. 62/414,785, which was filed on Oct. 30, 2016. The contents of each of these applications are hereby incorporated by reference, and to each of which priority is claimed.

REFERENCE TO A SEQUENCE LISTING SUBMITTED AS A TEXT FILE VIA EFS-WEB

The Sequence Listing submitted Apr. 10, 2019 as a text file named "000020_0006 PCT-LF_SL.txt," created on Nov. 13, 2017, and having a size of 131,318 bytes is hereby incorporated by reference pursuant to 37 C.F.R. § 1.52(e)(5).

FIELD OF THE INVENTION

The invention relates generally to anti-PD-L1 antibodies, their variants or mutants, or antigen binding fragment thereof, and methods of use thereof, in the treatment of human cancers.

BACKGROUND OF THE INVENTION

Programmed Death Ligand-1 (PD-L1) and Programmed Death Ligand-2 (PD-L2) are expressed on antigen-presenting cells as well as many human cancers and have been shown to downregulate T cell activation and cytokine secretion upon binding to PD-1 (Freeman et al., 2000; Latchman et al., 2001). Unlike CTLA-4, PD-1 primarily functions in peripheral tissues where activated T-cells may encounter the immunosuppressive PD-L1 (B7-H1) and PD-L2 (B7-DC) ligands expressed by tumor and/or stromal cells (Flies et al., 2011; Topalian et al., 2012a). Inhibition of the PD-1/PD-L1 interaction mediates potent antitumor activity in preclinical models (U.S. Pat. Nos. 8,008,449 and 7,943,743), and the use of antibody inhibitors of the PD-1/PD-L1 interaction for treating cancer has entered clinical trials (Brahmer et al., 2010; Flies et al., 2011; Topalian et al., 2012b; Brahmer et al., 2012).

It appears that upregulation of PD-L1 may allow cancers to evade the host immune system. Although many PD-L1 inhibitors are in development as immuno-oncology therapies and are showing good results in clinical trials. There exists a need for the development of anticancer therapeutics directed against PD-L1. The present invention meets this and other needs.

SUMMARY OF THE INVENTION

Provided by the invention are anti-PD-L1 antibodies and/or antigen binding fragments thereof. In certain embodiments, the anti-PD-L1 antibody of the invention, i.e., the PL1 antibody, comprises a light chain (LC) variable domain sequence comprising (1) a CDR-L1 comprising the amino acid sequence set forth in SEQ ID NO:35; (2) a CDR-L2 comprising the amino acid sequence set forth in SEQ ID NO: 41; and (3) a CDR-L3 comprising the amino acid sequence set forth in SEQ ID NO:44, and a heavy chain (HC) variable domain sequence comprising (1) a CDR-H1 comprising the amino acid sequence set forth in SEQ ID NO:51; (2) a CDR-H2 comprising the amino acid sequence set forth in SEQ ID NO:55; and (3) a CDR-H3 comprising the amino acid sequence set forth in SEQ ID NO:59.

In other embodiments, the anti-PD-L1 antibody of the invention, i.e., the PL2 antibody, comprises a light chain (LC) variable domain sequence comprising (1) a CDR-L1 comprising the amino acid sequence set forth in SEQ ID NO:36; (2) a CDR-L2 comprising the amino acid sequence set forth in SEQ ID NO: 42; and (3) a CDR-L3 comprising the amino acid sequence set forth in SEQ ID NO:45, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:60.

In other embodiments, the anti-PD-L1 antibody of the invention, i.e., the PL3 antibody, comprises a light chain (LC) variable domain sequence comprising (1) a CDR-L1 comprising the amino acid sequence set forth in SEQ ID NO:37; (2) a CDR-L2 comprising the amino acid sequence set forth in SEQ ID NO: 41; and (3) a CDR-L3 comprising the amino acid sequence set forth in SEQ ID NO:46, and a heavy chain (HC) variable domain sequence comprising (1) a CDR-H1 comprising the amino acid sequence set forth in SEQ ID NO:53; (2) a CDR-H2 comprising the amino acid sequence set forth in SEQ ID NO:55; and (3) a CDR-H3 comprising the amino acid sequence set forth in SEQ ID NO:61.

In other embodiments, the anti-PD-L1 antibody of the invention, i.e., the PL6 antibody, comprises a light chain (LC) variable domain sequence comprising (1) a CDR-L1 comprising the amino acid sequence set forth in SEQ ID NO:37; (2) a CDR-L2 comprising the amino acid sequence set forth in SEQ ID NO: 41; and (3) a CDR-L3 comprising the amino acid sequence set forth in SEQ ID NO:47, and a heavy chain (HC) variable domain sequence comprising (1) a CDR-H1 comprising the amino acid sequence set forth in SEQ ID NO:54; (2) a CDR-H2 comprising the amino acid sequence set forth in SEQ ID NO:57; and (3) a CDR-H3 comprising the amino acid sequence set forth in SEQ ID NO:62.

In other embodiments, the anti-PD-L1 antibody of the invention, i.e., the PL8 antibody, comprises a light chain (LC) variable domain sequence comprising (1) a CDR-L1 comprising the amino acid sequence set forth in SEQ ID NO:38; (2) a CDR-L2 comprising the amino acid sequence set forth in SEQ ID NO: 43; and (3) a CDR-L3 comprising the amino acid sequence set forth in SEQ ID NO:48, and a heavy chain (HC) variable domain sequence comprising (1) a CDR-H1 comprising the amino acid sequence set forth in SEQ ID NO:51; (2) a CDR-H2 comprising the amino acid sequence set forth in SEQ ID NO:58; and (3) a CDR-H3 comprising the amino acid sequence set forth in SEQ ID NO:63.

In other embodiments, the anti-PD-L1 antibody of the invention, i.e., the PL12 antibody, comprises a light chain (LC) variable domain sequence comprising (1) a CDR-L1 comprising the amino acid sequence set forth in SEQ ID NO:39; (2) a CDR-L2 comprising the amino acid sequence set forth in SEQ ID NO: 41; and (3) a CDR-L3 comprising the amino acid sequence set forth in SEQ ID NO:49, and a heavy chain (HC) variable domain sequence comprising (1) a CDR-H1 comprising the amino acid sequence set forth in SEQ ID NO:51; (2) a CDR-H2 comprising the amino acid sequence set forth in SEQ ID NO:55; and (3) a CDR-H3 comprising the amino acid sequence set forth in SEQ ID NO:64.

In other embodiments, the anti-PD-L1 antibody of the invention, i.e., the PL15 antibody, comprises a light chain (LC) variable domain sequence comprising (1) a CDR-L1 comprising the amino acid sequence set forth in SEQ ID NO:40; (2) a CDR-L2 comprising the amino acid sequence set forth in SEQ ID NO: 41; and (3) a CDR-L3 comprising the amino acid sequence set forth in SEQ ID NO:50, and a heavy chain (HC) variable domain sequence comprising (1) a CDR-H1 comprising the amino acid sequence set forth in SEQ ID NO:53; (2) a CDR-H2 comprising the amino acid sequence set forth in SEQ ID NO:55; and (3) a CDR-H3 comprising the amino acid sequence set forth in SEQ ID NO:61.

The invention further provides anti-PD-L1 antibody variants and/or mutants, or their antigen binding fragments thereof. In certain embodiments, the anti-PD-L1 antibody variant and/or mutants of the invention, i.e., the PL2 #3 antibody, comprises a light chain (LC) variable domain sequence comprising (1) a CDR-L1 comprising the amino acid sequence set forth in SEQ ID NO:65; (2) a CDR-L2 comprising the amino acid sequence set forth in SEQ ID NO: 42; and (3) a CDR-L3 comprising the amino acid sequence set forth in SEQ ID NO:71, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:77.

In other embodiments, the anti-PD-L1 antibody variant and/or mutants of the invention, i.e., the PL3 #7 antibody, comprises a light chain (LC) variable domain sequence comprising (1) a CDR-L1 comprising the amino acid sequence set forth in SEQ ID NO:37; (2) a CDR-L2 comprising the amino acid sequence set forth in SEQ ID NO: 41; and (3) a CDR-L3 comprising the amino acid sequence set forth in SEQ ID NO:72, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:55; and (3) a CDR-H3 comprising the amino acid sequence set forth in SEQ ID NO:78.

In other embodiments, the anti-PD-L1 antibody variant and/or mutants of the invention, i.e., the PL3 #7-19 antibody, comprises a light chain (LC) variable domain sequence comprising (1) a CDR-L1 comprising the amino acid sequence set forth in SEQ ID NO:66; (2) a CDR-L2 comprising the amino acid sequence set forth in SEQ ID NO:68; and (3) a CDR-L3 comprising the amino acid sequence set forth in SEQ ID NO:73, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:55; and (3) a CDR-H3 comprising the amino acid sequence set forth in SEQ ID NO:79. In certain embodiments, the mutants of the anti-PD-L1 antibody comprises CDR-L2 comprising one or more mutations at the N-glycosylation sites.

In other embodiments, the anti-PD-L1 antibody variant and/or mutants of the invention, i.e., the PL3 #7-43 antibody, comprises a light chain (LC) variable domain sequence comprising (1) a CDR-L1 comprising the amino acid sequence set forth in SEQ ID NO:35; (2) a CDR-L2 comprising the amino acid sequence set forth in SEQ ID NO:69; and (3) a CDR-L3 comprising the amino acid sequence set forth in SEQ ID NO:74, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:55; and (3) a CDR-H3 comprising the amino acid sequence set forth in SEQ ID NO:80. In certain embodiments, the mutants of the anti-PD-L1 antibody comprises CDR-L2 comprising one or more mutations at the N-glycosylation sites.

In other embodiments, the anti-PD-L1 antibody variant and/or mutants of the invention, i.e., the PL3 #7-54 antibody, comprises a light chain (LC) variable domain sequence comprising (1) a CDR-L1 comprising the amino acid sequence set forth in SEQ ID NO:67; (2) a CDR-L2 comprising the amino acid sequence set forth in SEQ ID NO:70; and (3) a CDR-L3 comprising the amino acid sequence set forth in SEQ ID NO:72, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:76; and (3) a CDR-H3 comprising the amino acid sequence set forth in SEQ ID NO:81.

In other embodiments, the anti-PD-L1 antibody variant and/or mutants of the invention, i.e., the PL2 #4 antibody, comprises a light chain (LC) variable domain sequence comprising (1) a CDR-L1 comprising the amino acid sequence set forth in SEQ ID NO:94; (2) a CDR-L2 comprising the amino acid sequence set forth in SEQ ID NO:42; and (3) a CDR-L3 comprising the amino acid sequence set forth in SEQ ID NO:95, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:96.

In other embodiments, the anti-PD-L1 antibody variant and/or mutants of the invention, i.e., the PL2 #5 antibody, comprises a light chain (LC) variable domain sequence comprising (1) a CDR-L1 comprising the amino acid sequence set forth in SEQ ID NO:97; (2) a CDR-L2 comprising the amino acid sequence set forth in SEQ ID NO:42; and (3) a CDR-L3 comprising the amino acid sequence set forth in SEQ ID NO:98, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:99.

In other embodiments, the anti-PD-L1 antibody variant and/or mutants of the invention, i.e., the PL2 #39 antibody, comprises a light chain (LC) variable domain sequence comprising (1) a CDR-L1 comprising the amino acid sequence set forth in SEQ ID NO:100; (2) a CDR-L2 comprising the amino acid sequence set forth in SEQ ID NO:42; and (3) a CDR-L3 comprising the amino acid sequence set forth in SEQ ID NO:95, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:101.

In other embodiments, the anti-PD-L1 antibody variant and/or mutants of the invention, i.e., the PL3 #1 antibody, comprises a light chain (LC) variable domain sequence comprising (1) a CDR-L1 comprising the amino acid sequence set forth in SEQ ID NO:37; (2) a CDR-L2 comprising the amino acid sequence set forth in SEQ ID NO:106; and (3) a CDR-L3 comprising the amino acid sequence set forth in SEQ ID NO:107, and a heavy chain (HC) variable domain sequence comprising (1) a CDR-H1 comprising the amino acid sequence set forth in SEQ ID NO:108; (2) a CDR-H2 comprising the amino acid sequence set forth in SEQ ID NO:55; and (3) a CDR-H3 comprising the amino acid sequence set forth in SEQ ID NO:109.

The amino acid sequences of the above noted CDRs (CDR-L1, -L2, & -L3; and CDR-H1, -H2, and -H3) of each anti-PD-L1 antibody and its variant/mutant are provided in Table 1 below.

TABLE 1

| Anti-PD-L1 | CDR-L1 | CDR-L2 | CDR-L3 | CDR-H1 | CDR-H2 | CDR-H3 |
|---|---|---|---|---|---|---|
| PL1 | TGSSSNVGAGYDVH (SEQ ID NO: 35) | GNSNRPS (SEQ ID NO: 41) | QSYDSSLSGWV (SEQ ID NO: 44) | SYAIS (SEQ ID NO: 51) | RIIPILGIANY AQKFQG (SEQ ID NO: 55) | EGSSGWLGVLDY (SEQ ID NO: 59) |
| PL2 | SGSSSYIESSYVS (SEQ ID NO: 36) | DDDMRPS (SEQ ID NO: 42) | EIWDSGLGGV (SEQ ID NO: 45) | SYTMN (SEQ ID NO: 52) | SISSGSDYLY YADSVKG (SEQ ID NO: 56) | NELRWYPQAG AFDI (SEQ ID NO: 60) |
| PL3 | TGSSSNIGAGYDVH (SEQ ID NO: 37) | GNSNRPS (SEQ ID NO: 41) | QSYDSSLSAPVV (SEQ ID NO: 46) | SYTIS (SEQ ID NO: 53) | RIIPILGIANY AQKFQG (SEQ ID NO: 55) | SRDGYSFGAFDI (SEQ ID NO: 61) |
| PL6 | TGSSSNIGAGYDVH (SEQ ID NO: 37) | GNSNRPS (SEQ ID NO: 41) | QSYDSSLSG.GV (SEQ ID NO: 47) | SYTIN (SEQ ID NO: 54) | KIIPILGIADY AQMFKG (SEQ ID NO: 57) | GGYVGYLNAF DI (SEQ ID NO: 62) |
| PL8 | QGDSLRSYYVS (SEQ ID NO: 38) | GKNNRPS (SEQ ID NO: 43) | NSRDSTGNLLRV (SEQ ID NO: 48) | SYAIS (SEQ ID NO: 51) | RIIPIFGTANY AQKFQG (SEQ ID NO: 58) | EGVLDAF DI (SEQ ID NO: 63) |
| PL12 | TRSSSNIGAGHDVH (SEQ ID NO: 39) | GNSNRPS (SEQ ID NO: 41) | QSYDSSLTG.VV (SEQ ID NO: 49) | SYAIS (SEQ ID NO: 51) | RIIPILGIANY AQKFQG (SEQ ID NO: 55) | GIGSYSFGAFDI (SEQ ID NO: 64) |
| PL15 | TGYSSNIGAGYDVH (SEQ ID NO: 40) | GNSNRPS (SEQ ID NO: 41) | QSYDNSLSVSV (SEQ ID NO: 50) | SYTIS (SEQ ID NO: 53) | RIIPILGIANY AQKFQG (SEQ ID NO: 55) | SRDGYSFGAFDI (SEQ ID NO: 61) |

| Variant | CDR-L1 | CDR-L2 | CDR-L3 | CDR-H1 | CDR-H2 | CDR-H3 |
|---|---|---|---|---|---|---|
| PL2#3 | SGSSSYIESSYVG (SEQ ID NO: 65) | DDDMRPS (SEQ ID NO: 42) | EIWRSGLGGV (SEQ ID NO: 71) | SYTMN (SEQ ID NO: 52) | SISSGSDYLY YADSVKG (SEQ ID NO: 56) | NELRWYPQAG AFDR (SEQ ID NO: 77) |
| PL3#7 | TGSSSNIGAGYDVH (SEQ ID NO: 37) | GNSNRPS (SEQ ID NO: 41) | QTYDSSLSARVV (SEQ ID NO: 72) | SYPIS (SEQ ID NO: 75) | RIIPILGIANY AQKFQG (SEQ ID NO: 55) | SRDGYAFGAFDI (SEQ ID NO: 78) |
| PL3#7-19 | TGSSSNIGGGYDVH (SEQ ID NO: 66) | GNSTRPS (SEQ ID NO: 68) | QTYDSSLSATVV (SEQ ID NO: 73) | SYPIS (SEQ ID NO: 75) | RIIPILGIANY AQKFQG (SEQ ID NO: 55) | SRDGYAFGAFDV (SEQ ID NO: 79) |
| PL3#7-43 | TGSSSNVGAGYDVH (SEQ ID NO: 35) | GNSNRSS (SEQ ID NO: 69) | QTYDSSGSARVV (SEQ ID NO: 74) | SYPIS (SEQ ID NO: 75) | RIIPILGIANY AQKFQG (SEQ ID NO: 55) | SRPGYAFGAFDI (SEQ ID NO: 80) |
| PL3#7-54 | TGSSSNIGQGYDVH (SEQ ID NO: 67) | ANSNRPS (SEQ ID NO: 70) | QTYDSSLSARVV (SEQ ID NO: 72) | SYPIS (SEQ ID NO: 75) | RIIPILGIADY AQKFQG (SEQ ID NO: 76) | SRPGYAFGAFDI (SEQ ID NO: 80) |
| PL2#4 | SGVSSYIESSYVS (SEQ ID NO: 94) | DDDMRPS (SEQ ID NO: 42) | KIWDSGLGGV (SEQ ID NO: 95) | SYTMN (SEQ ID NO: 52) | SISSGSDYLY YADSVKG (SEQ ID NO: 56) | NELRWYPLAG AFDI (SEQ ID NO: 96) |
| PL2#5 | SGSSSYIESSYVS (SEQ ID NO: 36) | DDDMRPS (SEQ ID NO: 42) | EIWDSRLGGV (SEQ ID NO: 98) | SYTMN (SEQ ID NO: 52) | SISSGSDYLY YADSVKG (SEQ ID NO: 56) | NELRWYPFAGA FDI (SEQ ID NO: 99) |
| PL2#39 | SGSSSYITSSYVS (SEQ ID NO: 100) | DDDMRPS (SEQ ID NO: 42) | KIWDSGLGGV (SEQ ID NO: 95) | SYTMN (SEQ ID NO: 52) | SISSGSDYLY YADSVKG AQKFQG (SEQ ID NO: 56) | NELRWYPKAG AFDI (SEQ ID NO: 101) |

TABLE 1-continued

| | | | | | | |
|---|---|---|---|---|---|---|
| PL3#1 | TGSSSNIGAGYDVH (SEQ ID NO: 37) | GNSRRPS (SEQ ID NO: 106) | QTYDSSLSRPVV (SEQ ID NO: 107) | SYRIS (SEQ ID NO: 108) | RIIPILGIANY (SEQ ID NO: 55) | SRDGYSVGAFDS (SEQ ID NO: 109) |

In some embodiments, the anti-PD-L1 antibody and a variant thereof, comprises a light chain (LC) variable domain sequence comprising (1) a CDR-L1 comprising an amino acid sequence selected from the group consisting of SEQ ID Nos: 35-40, 65-67, 94, 97, and 100; (2) a CDR-L2 comprising an amino acid sequence selected from the group consisting of SEQ ID Nos: 41-43, 68-70, and 106; (3) a CDR-L3 comprising an amino acid sequence selected from the group consisting of SEQ ID Nos: 44-50, 71-74, 95, 98 and 107, and a heavy chain (HC) variable domain sequence comprising (1) a CDR-H1 comprising an amino acid sequence selected from the group consisting of SEQ ID Nos: 51-54, 75, and 108; (2) a CDR-H2 comprising an amino acid sequence selected from the group consisting of SEQ ID Nos: 55-58 and 76; and (3) a CDR-H3 comprising an amino acid sequence selected from the group consisting of SEQ ID Nos: 59-64, 77-81, 96, 99, 101, and 109.

Also provided by the invention are anti-PD-L1 antibodies, their variants, or antigen binding fragments thereof, comprising a light chain (LC) variable domain sequence comprising the amino acid sequence set forth in SEQ ID NOs: 1-7, 16, 20, 24, 28, 32, 83, 87, 91, or 103; and a heavy chain (HC) variable domain sequence comprising the amino acid sequence set forth in SEQ ID Nos: 8-14, 18, 22, 26, 30, 34, 85, 89, 93, or 105. Nucleic acid sequences encoding these LC and HC domains are also provided.

In some embodiments, according to (or as applied to) any of the embodiments above, the antibody of the invention comprises one or more mutations at the N-glycosylation sites of its one or more CDRs in the variable domains. The resulting de-glycosylated antibody remains the equal function as the parent non-de-glycosylated antibody.

In some embodiments, according to (or as applied to) any of the embodiments above, the antibody comprises an Fc sequence of a human IgG. In some embodiments, according to (or as applied to) any of the embodiments above, the antigen binding fragment is selected from the group consisting of a Fab, Fab', a F(ab)'2, a single-chain Fv (scFv), an Fv fragment, a diabody, and a linear antibody. In some embodiments, according to (or as applied to) any of the embodiments above, the antibody is a multispecific antibody.

In some embodiments, according to (or as applied to) any of the embodiments above, the anti-PD-L1 antibody, the variant or antigen binding fragment thereof, is conjugated to a therapeutic agent. In some embodiments, according to (or as applied to) any of the embodiments above, the anti-PD-L1 antibody, the variant or antigen binding fragment thereof, is conjugated to a label. In some embodiments, according to (or as applied to) any of the embodiments above, the label is selected from the group consisting of a radioisotope, a fluorescent dye, and an enzyme.

The invention provides an isolated nucleic acid molecule that encodes the anti-PD-L1 antibody, the variant, the mutant, or antigen binding fragment thereof, according to (or as applied to) any of the embodiments above. Also provided is an expression vector encoding the nucleic acid molecule according to (or as applied to) any of the embodiments above. Cells comprising the expression vector according to (or as applied to) any of the embodiments above are also provided. The invention also provides a method of producing an antibody, the variant or the antigen binding fragment thereof, comprising culturing a cell according to (or as applied to) any of the embodiments above and recovering the antibody or antigen-binding fragment thereof from the cell culture. In some embodiments, according to (or as applied to) any of the embodiments above, the cell is a mammalian cell. In some embodiments, according to (or as applied to) any of the embodiments above, the mammalian cell is a CHO cell. In some embodiments, according to (or as applied to) any of the embodiments above, the cell is a stable mammalian cell line. In some embodiments, according to (or as applied to) any of the stable mammalian cell line is a CHO cell line.

The invention provides a composition comprising the anti-PD-L1 antibody, the variant, the mutant, or antigen binding fragment thereof, according to (or as applied to) any of the embodiments above and a pharmaceutically acceptable carrier.

The invention provides a method of detecting a PD-L1 protein in sample from a patient by contacting the anti-PD-L1 antibody, the variant, the mutant, or antigen binding fragment thereof, according to (or as applied to) any of the embodiments above to the sample and detecting the anti-PD-L1 antibody bound to the PD-L1 protein. In some embodiments, according to (or as applied to) any of the embodiments above, the anti-PD-L1 antibody, the variant or antigen binding fragment thereof, is used an immunohistochemistry assay (IHC) or in an ELISA assay.

Also provided is a method of treating cancer in a subject, comprising administering an effective amount of the composition according to (or as applied to) any of the embodiments above to the subject. Also provided is a composition comprising an anti-PD-L1 antibody, the variant, the mutant, or antigen binding fragment thereof, according to (or as applied to) any of the embodiments above for use in the treatment of cancer. Provided is the use of an anti-PD-L1 antibody, the variant, the mutant, or antigen binding fragment thereof, according to (or as applied to) any of the embodiments above in the manufacturing a medicament for treating cancer. In some embodiments according to (or as applied to) any of the embodiments above, the cancer is selected from melanoma, head and neck cancer, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer and non-small cell lung cancer (NSCLC), esophageal cancer, nasopharyngeal carcinoma (NPC), biliary tract cancer, colorectal cancer, cervical cancer, thyroid cancer, and salivary cancer. In some embodiments, according to (or as applied to) any of the embodiments above, the subject is further administered a therapeutic agent selected from the group consisting of an anti-neoplastic agent, a chemotherapeutic agent, a growth inhibitory agent and a cytotoxic agent. In some embodiments, according to (or as applied to) any of the embodiments above, the subject is further administered radiation therapy.

BRIEF DESCRIPTION OF THE DRAWINGS

FIGS. 1A-1B Amino acid sequence alignment of light chain (FIG. 1A) and heavy chain (FIG. 1B) of anti-PD-L1 selected leads PL1, PL2, PL3, PL6, PL8, PL12, PL15. Seven selected antibody leads with binding and blocking activity to human PD-L1 in the subsequent ELISA and flow cytometry assays were identified by screening of human Fab naïve phage display library with human PD-L1_ECD-His. These selected Fab sequences were then cloned into N297A mutant of human IgG1 Fc backbone to become full-length antibodies. Sequence alignment of the antibody leads was listed and Complementary Determining Regions (CDRs) were marked in bold and underlined text.

FIG. 4A is a bar graph showing the IFN-γ secretion; FIG. 4B is a bar graph showing the $CD3^+$ T cell proliferation at indicated concentration of antibodies.

FIG. 6A depicts the bar graphs showing the secreted IL-2 induced by PL2 parental and variants; FIG. 6B depicts the bar graph showing the IL-2 secretion in MLR at indicated concentration of PL3 parental antibody and variants.

FIG. 8C is a bar graph showing the $CD4^+$ T cell proliferation at various concentrations of antibodies; FIG. 8D is a bar graph showing the $CD8^+$ T cell proliferation at indicated concentrations of antibodies.

FIG. 9A shows the individual tumor volumes of mice (n=4/group) treated with different IgG forms of PL2 #3 at day 32. The individual tumor volumes of mice (n=4/group) treated with various PL3 #7 IgG subclasses at day 32 are presented in FIG. 9B.

FIGS. 11A-11B Amino acid sequence alignment of light chain (FIG. 11A) (SEQ ID NOS 136-140, respectively, in order of appearance) and heavy chain (FIG. 11B) (SEQ ID NOS 141-145, respectively, in order of appearance) of anti-PD-L1 top variants. PL2 top variant (PL2 #3), PL3 top variant (PL3 #7), and PL3 #7 top variants (PL3 #7-19, -43, -54) with superior higher affinity and superior functional activities were generated from in vitro phage display-based affinity maturation experiments. In general, three rounds of panning were performed using biotinylated hPD-L1-His coupled to streptavidin-coated magnetic Dynabeads® M-280. Fabs of top variants were then screened via ELISA and cloned into N297A mutant of human IgG1 Fc backbone to become full-length antibodies. Sequence alignment of top variants was listed here and CDRs (Complementary Determining Regions) were marked in bold and underlined text.

FIG. 12A is a bar graph showing the IFN-γ secretion; FIG. 12B is a bar graph showing the $CD8^+$ T cell proliferation at indicated concentration of antibodies.

FIG. 18. Amino acid sequence alignment of light chain variable regions of de-glycosylated version of PL3 #7-19 variants and PL3 #7-43 variants (SEQ ID NOS 20, 24, 111, 113, 115, 28, 117, and 119, respectively, in order of appearance). Sequence alignment of light chains of these de-glycosylated variants was listed here and CDRs (Complementary Determining Regions) were marked in bold and underlined text. Heavy chains of them were unchanged and identical as their parental variants (sequence alignment not shown here).

FIGS. 19A-19B. Whole cell binding of de-glycosylated version of PL3 #7-19 variants (FIG. 19A) and PL3 #7-43 variants (FIG. 19B). Whole cell binding activity to PD-L1 transfected CHO-S cells of the resultant three de-glycosylated variants for PL3 #7-19 (i.e., PL3 #7-19 deglyco1, deglyco2, deglyco3) and two de-glycosylated variants for PL3 #7-43 (i.e., PL3 #7-43 deglyco1, deglyco2) were determined with flow cytometry. All the de-glycosylated antibody variants tested here were in N297A mutant of human IgG1 Fc backbone. In-house anti-PD-1 antibody (i.e., HLX10) was used as the negative control.

DETAILED DESCRIPTION OF THE INVENTION

Figure 2A:
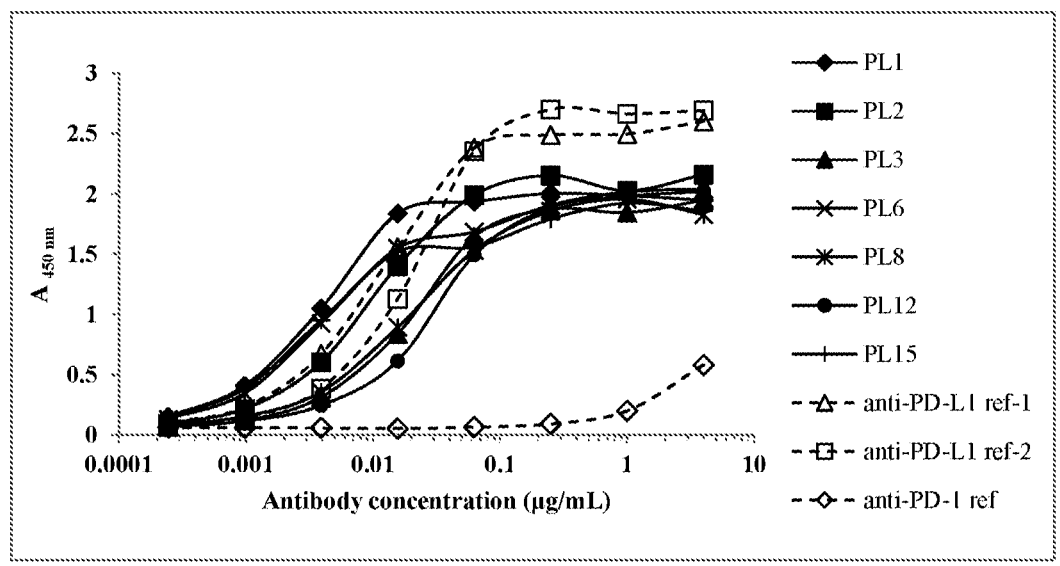
FIGS. 2A-2B. Binding of selected antibodies to recombinant human PD-L1/Fc fusion proteins (FIG. 2A) and activated $CD3^+$ T cells (FIG. 2B). Selected antibodies were tested for the binding to recombinant human PD-L1 proteins by ELISA and activated $CD3^+$ T cells by flow cytometry. Anti-PD-L1 reference antibody and anti-PD-1 reference antibody were used as the positive and negative control, respectively.

The present invention provides novel anti-PD-L1 antibodies, the variants, the mutants, and/or antigen binding fragments thereof. The inventors have surprisingly found that certain anti-PD-L1 antibodies and their affinity variants and/or mutants enhance the secretion of IL-2 and IFNγ by T cells and proliferation of CD4$^+$ and CD8$^+$ T cells. The anti-PD-L1 antibodies described herein also exhibit enhanced efficacy and/or anti-tumor activities as compared to certain anti-PD-L1 reference monoclonal antibodies used to treat cancer.

Also provided are immunoconjugates, nucleic acids encoding the novel anti-PD-L1 antibodies, their affinity variants or antigen binding fragments thereof, as described herein, and compositions (such as pharmaceutical compositions). The invention also provides methods of using novel anti-PD-L1 antibodies, the affinity variants and/or mutants, or antigen binding fragments thereof, to detect PD-L1 in a sample (such as an in vivo or ex vivo sample), compositions comprising such antibodies, the variants and/or mutants, or antigen binding fragments thereof, for use in treating cancer, and uses of such antibodies, the variants or antigen binding fragments thereof, in the manufacture of a medicament for the treatment of cancer.

Definitions

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods provided herein contemplate any one or more of these aspects of treatment.

The terms "recurrence," "relapse" or "relapsed" refers to the return of a cancer or disease after clinical assessment of the disappearance of disease. A diagnosis of distant metastasis or local recurrence can be considered a relapse.

The term "refractory" or "resistant" refers to a cancer or disease that has not responded to treatment.

The term "adjuvant therapy" refers to treatment given after the primary therapy, usually surgery. Adjuvant therapy for cancer or disease may include immune therapy, chemotherapy, radiation therapy, or hormone therapy.

The term "maintenance therapy" refers to scheduled retreatment that is given to help maintain a previous treatment's effects. Maintenance therapy is often given to help keep cancer in remission or prolong a response to a specific therapy regardless of disease progression.

The term "invasive cancer" refers to cancer that has spread beyond the layer of tissue in which it started into the normal surrounding tissues. Invasive cancers may or may not be metastatic.

The term "non-invasive cancer" refers to a very early cancer or a cancer that has not spread beyond the tissue of origin.

The term "progression-free survival" in oncology refers to the length of time during and after treatment that a cancer does not grow. Progression-free survival includes the amount of time patients have experienced a complete response or a partial response, as well as the amount of time patients have experienced stable disease.

The term "progressive disease" in oncology can refer to a tumor growth of more than 20 percent since treatment began—either due to an increase in mass or a spread in the tumor.

A "disorder" is any condition that would benefit from treatment with the antibody. For example, mammals who suffer from or need prophylaxis against abnormal PD-L1 activity. This includes chronic and acute disorders or diseases including those pathological conditions that predispose the mammal to the disorder in question. Non-limiting examples of disorders to be treated herein include cancer (such as head and neck cancer, throat cancer, colorectal cancer, lung cancer, etc.).

"Tumor", as used herein, refers to all neoplastic cell growth and proliferation, whether malignant or benign, and all pre-cancerous and cancerous cells and tissues.

The term "antibody" is used in the broadest sense and specifically covers, for example, single monoclonal antibodies (including agonist, antagonist, and neutralizing antibodies), antibody compositions with polyepitopic specificity, polyclonal antibodies, single chain anti-antibodies, and fragments of antibodies (see below) as long as they specifically bind a native polypeptide and/or exhibit a biological activity or immunological activity of this invention. According to one embodiment, the antibody binds to an oligomeric form of a target protein, e.g., a trimeric form. According to another embodiment, the antibody specifically binds to a protein, where binding can be inhibited by a monoclonal antibody of this invention (e.g., a deposited antibody of this invention, etc.). The phrase "functional fragment or analog" of an antibody is a compound having a qualitative biological activity in common with an antibody to which it is being referred. For example, a functional fragment or analog of an antibody of this invention can be one that can specifically bind to PD-L1. In one embodiment, the antibody can prevent or substantially reduce the ability of PD-L1 to induce cell proliferation.

An "isolated antibody" is one that has been identified and separated and/or recovered from a component of its natural environment. Contaminant components of its natural environment are materials that would interfere with diagnostic or therapeutic uses for the antibody, and can include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to H chain by one covalent disulfide bond, while the two H chains are linked to each other by one or more disulfide bonds depending on the H chain isotype. Each H and L chain also has regularly spaced intrachain disulfide bridges. Each H chain has, at the N-terminus, a variable domain ($V_H$) followed by three constant domains ($C_H$) for each of α and γ chains and four $C_H$ domains for μ and ε isotypes. Each L chain has, at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues that encompass the CDRs as defined by each of the above cited references are set forth below in Table 2 as a comparison.

TABLE 2

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

The term "monoclonal antibody" as used herein refers to an antibody obtained from a population of substantially homogeneous antibodies, i.e., the individual antibodies comprising the population are identical except for possible naturally-occurring mutations that can be present in minor amounts. Monoclonal antibodies are highly specific, being directed against a single antigenic site. Furthermore, in contrast to polyclonal antibody preparations, which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" is not to be construed as requiring production of the antibody by any particular method. For example, the monoclonal antibodies useful in the present invention can be prepared by the hybridoma methodology first described by Kohler et al. Nature. 256:495 (1975), or can be made using recombinant DNA methods in bacterial, eukaryotic animal or plant cells (see, e.g., U.S. Pat. No. 4,816,567). The "monoclonal antibodies" can also be isolated from phage antibody libraries using the techniques described in Clackson et al., Nature, 352:624-628 (1991), Marks et al., J. Mol. Biol., 222:581-597 (1991), and the Examples below, for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g., Old World Monkey, Ape etc), and human constant region sequences.

An "intact" antibody is one that comprises an antigen-binding site as well as a $C_L$ and at least heavy chain constant domains, $C_H1$, $C_H2$ and $C_H3$. The constant domains can be native sequence constant domains (e.g., human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. The expression "linear antibodies" generally refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The Fc fragment comprises the carboxy-terminal portions of both H chains held together by di sulfides. The effector functions of antibodies are determined by sequences in the Fc region, which region is also the part recognized by Fc receptors (FcR) found on certain types of cells.

A "variant Fc region" comprises an amino acid sequence that differs from a native sequence Fc region by virtue of at least one "amino acid modification" as defined herein. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. In one embodiment, the variant Fc region herein will possess at least about 80% homology, at least about 85% homology, at least about 90% homology, at least about 95% homology or at least about 99% homology with a native sequence Fc region. According to another embodiment, the variant Fc region herein will possess at least about 80% homology, at least about 85% homology, at least about 90% homology, at least about 95% homology or at least about 99% homology with an Fc region of a parent polypeptide.

The term "Fc region-comprising polypeptide" refers to a polypeptide, such as an antibody or immunoadhesin (see definitions elsewhere herein), which comprises an Fc region. The C-terminal lysine (residue 447 according to the EU numbering system) of the Fc region may be removed, for example, during purification of the polypeptide or by recombinantly engineering the nucleic acid encoding the polypeptide. Accordingly, a composition comprising polypeptides, including antibodies, having an Fc region according to this invention can comprise polypeptides populations with all K447 residues removed, polypeptide populations with no K447 residues removed, or polypeptide populations having a mixture of polypeptides with and without the K447 residue.

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors; and B cell activation. A "native sequence Fc region" comprises an amino acid sequence identical to the amino acid sequence of an Fc region found in nature. Examples of Fc sequences are described in, for example, but not limited to, Kabat et al., Sequences of Immunological Interest. 5th Ed. Public Health Service, National Institutes of Health, Bethesda, Md. (1991)).

"Fv" is the minimum antibody fragment that contains a complete antigen-recognition and -binding site. This fragment consists of a dimer of one heavy- and one light-chain variable region domain in tight, non-covalent association. From the folding of these two domains, emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as a mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways by someone skilled in the art, for instance, using publicly available computer software such as BLAST, BLAST-2, ALIGN or Megalign (DNASTAR). Those skilled in the art can determine appropriate parameters for measuring alignment, including any algorithms needed to achieve maximal alignment over the full length of the sequences being compared. For purposes herein, however, percentage (%) amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

The terms "Fc receptor" or "FcR" are used to describe a receptor that binds to the Fc region of an antibody. In one embodiment, an FcR of this invention is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daeron, Annu. Rev. Immunol. 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

The term "FcRn" refers to the neonatal Fc receptor (FcRn). FcRn is structurally similar to major histocompatibility complex (MHC) and consists of a α-chain noncovalently bound to β2-microglobulin. The multiple functions of the neonatal Fc receptor FcRn are reviewed in Ghetie and Ward (2000) Annu. Rev. Immunol. 18, 739-766. FcRn plays a role in the passive delivery of immunoglobulin IgGs from the mother to the young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, Molec. Immunol. 22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e., residues 233 to 239 of the Fc region. In previous reports, FcR binding was generally attributed to amino acid residues in the lower hinge region of an IgG Fc region.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec Immunol. 22:161-206 (1985).

The "CH3 domain" (also referred to as "C2" or "H3" domain) comprises the stretch of residues C-terminal to a CH2 domain in an Fc region (i.e., from about amino acid residue 341 to the C-terminal end of an antibody sequence, typically at amino acid residue 446 or 447 of an IgG).

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g. an antibody variable domain) and can be assessed using various assays as disclosed herein, for example.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g., Quidel, San Diego, Calif.

The term "binding domain" refers to the region of a polypeptide that binds to another molecule. In the case of an FcR, the binding domain can comprise a portion of a polypeptide chain thereof (e.g., the alpha chain thereof) which is responsible for binding an Fc region. One useful binding domain is the extracellular domain of an FcR alpha chain.

An antibody with a variant IgG Fc with "altered" FcR binding affinity or ADCC activity is one that has either enhanced or diminished FcR binding activity (e.g., FcγR or FcRn) and/or ADCC activity compared to a parent polypeptide or to a polypeptide comprising a native sequence Fc region. The variant Fc that "exhibits increased binding" to an FcR binds at least one FcR with higher affinity (e.g., lower apparent Kd or IC50 value) than the parent polypeptide or a native sequence IgG Fc. According to some embodiments, the improvement in binding compared to a parent polypeptide is about 3-fold, preferably about 5-, 10-, 25-, 50-, 60-, 100-, 150-, 200-, up to 500-fold, or about 25% to 1000% improvement in binding. The polypeptide variant, which "exhibits decreased binding" to an FcR, binds at least one FcR with lower affinity (e.g., higher apparent Kd or higher IC50 value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or in the Examples below may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The polypeptide comprising a variant Fc region that "exhibits increased ADCC" or mediates antibody-dependent cell-mediated cytotoxicity (ADCC) in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g., in an animal model etc. In one embodiment, the preferred variant is from about 5-fold to about 100-fold, e.g., from about 25- to about 50-fold, more effective at mediating ADCC than the wild type Fc (or the parent polypeptide).

"Complement dependent cytotoxicity" or "CDC" refers to the lysis of a target cell in the presence of complement. Activation of the classical complement pathway is initiated by the binding of the first component of the complement system (C1 q) to antibodies (of the appropriate subclass) which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. J. Immunol. 164: 4178-4184 (2000).

An "effective amount" of an anti-PD-L1 antibody (or fragment thereof) or composition as disclosed herein is an amount sufficient to carry out a specifically stated purpose. An "effective amount" can be determined empirically and by known methods relating to the stated purpose. The term "therapeutically effective amount" refers to an amount of an anti-PD-L1 antibody (or the variant or antigen binding fragment thereof) or composition as disclosed herein, effective to "treat" a disease or disorder in a mammal (aka patient). In the case of cancer, the therapeutically effective amount of the anti-PD-L1 antibody (or the variant or antigen binding fragment thereof) or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the anti-PD-L1 antibody (or the variant or antigen binding fragment thereof) or composition as disclosed herein can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

A "cytotoxic amount" of an anti-PD-L1 antibody (or a variant or antigen binding fragment thereof) or composition of this invention is an amount capable of causing the destruction of a cell, especially tumor, e.g., cancer cell, either in vitro or in vivo. A "cytotoxic amount" of an anti-PD-L1 antibody (or a variant or antigen binding fragment thereof) or composition of this invention for purposes of inhibiting neoplastic cell growth can be determined empirically and by methods known in the art.

A "growth inhibitory amount" of an anti-PD-L1 antibody (or a variant or antigen binding fragment thereof) or composition of this invention is an amount capable of inhibiting the growth of a cell, especially tumor, e.g., cancer cell, either in vitro or in vivo. A "growth inhibitory amount" of an anti-PD-L1 antibody (or a variant or antigen binding fragment thereof) or composition of this invention for purposes of inhibiting neoplastic cell growth can be determined empirically and by known methods or by examples provided herein.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "detecting" is intended to include determining the presence or absence of a substance or quantifying the amount of a substance (such as PD-L1). The term thus refers to the use of the materials, compositions, and methods of the present invention for qualitative and quantitative determinations. In general, the particular technique used for detection is not critical for practice of the invention.

For example, "detecting" according to the invention may include: observing the presence or absence of PD-L1 gene product, mRNA molecules, or a PD-L1 polypeptide; a change in the levels of a PD-L1 polypeptide or amount bound to a target; a change in biological function/activity of a PD-L1 polypeptide. In some embodiments, "detecting" may include detecting wild type PD-L1 levels (e.g., mRNA or polypeptide levels). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

The word "label" when used herein refers to a detectable compound or composition that is conjugated directly or indirectly to the antibody. The label may itself be detectable by itself (e.g., radioisotope labels or fluorescent labels) or, in the case of an enzymatic label, may catalyze chemical alteration of a substrate compound or composition that is detectable.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects and embodiments of the invention described herein include "comprising," "consisting," and "consisting essentially of" aspects and embodiments.

All references cited herein, including patent applications and publications, are hereby incorporated by reference in their entirety.

Anti-PD-L1 Antibodies and Affinity Variants/Mutants

The present invention is based on the identification of novel antibodies that bind PD-L1 receptor (PD-L1). The anti-PD-L1 antibodies, and their affinity variants and/or mutants, or antigen binding fragments thereof, can be used in a variety of therapeutic and diagnostic methods. For example, the anti-PD-L1 antibodies and their affinity variants and/or mutants or antigen binding fragments can be used alone or in combination with other agents in treating disease characterized by abnormal PD-L1 expression or abnormal PD-L1 activity, including, e.g., melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer. The antibodies provided herein can also be used for detecting PD-L1 protein in patients or patient samples by administering the anti-PD-L1 antibodies, and/or their affinity variants/mutants or antigen binding fragments thereof, to patients and detecting the anti-PD-L1 antibody, and/or variants/mutants, or antigen binding fragments thereof, bound to the PD-L1 protein in a sample from the patient (e.g., in vivo or ex vivo) or by contacting the anti-PD-L1 antibodies, and/or variants/mutants or antigen binding fragments thereof, with samples from patients and detecting qualitatively or quantitatively the anti-PD-L1 antibody, and/or affinity variant/mutant or antigen binding fragment thereof, bound to the PD-L1 protein.

Programmed death-ligand 1 (PD-L1) also known as cluster of differentiation 274 (CD274) or B7 homolog 1 (B7-H1) is a protein that in humans is encoded by the CD274 (PD-L1) gene. PD-L1 is a type 1 transmembrane protein and plays a major role in suppressing the immune system during particular events such as pregnancy, tissue allografts, autoimmune disease and other disease states such as hepatitis. The binding of PD-L1 to PD-1 or B7.1 transmits an inhibitory signal that reduces the proliferation of these $CD8^+$ T cells at the lymph nodes and supplementary to that PD-1 is also able to control the accumulation of foreign antigen specific T cells in the lymph nodes through apoptosis, which is further mediated by a lower regulation of the gene Bcl-2.

An anti-PD-L1 antibody is an antibody that binds to PD-L1 with sufficient affinity and specificity. Preferably, an anti-PD-L1 antibody provided herein (or the variant or mutant or antigen-binding fragment thereof) can be used as a therapeutic agent in targeting and interfering with diseases or conditions wherein the PD-L1 activity is involved. An anti-PD-L1 antibody (or the variant/mutant or antigen binding fragment thereof) will usually not bind to other immunoglobulin superfamily. Preferably, the anti-PD-L1 antibody (or the variant/mutant or antigen binding fragment thereof) is a human or recombinant humanized anti-PD-L1 monoclonal antibody.

According to certain embodiments, the anti-PD-L1 antibody comprises the CDRs, the variable heavy chain region, and/or the variable light region of any one of the antibodies disclosed herein.

The invention provides anti-PD-L1 antibodies, their affinity variants/mutants, and/or antigen binding fragments thereof. In certain embodiments, the anti-PD-L1 antibody of the invention, i.e., the PL1 antibody, comprises a light chain (LC) variable domain sequence comprising (1) a CDR-L1 comprising the amino acid sequence set forth in SEQ ID NO:35; (2) a CDR-L2 comprising the amino acid sequence set forth in SEQ ID NO: 41; and (3) a CDR-L3 comprising the amino acid sequence set forth in SEQ ID NO:44, and a heavy chain (HC) variable domain sequence comprising (1) a CDR-H1 comprising the amino acid sequence set forth in SEQ ID NO:51; (2) a CDR-H2 comprising the amino acid sequence set forth in SEQ ID NO:55; and (3) a CDR-H3 comprising the amino acid sequence set forth in SEQ ID NO:59.

In other embodiments, the anti-PD-L1 antibody of the invention, i.e., the PL2 antibody, comprises a light chain (LC) variable domain sequence comprising (1) a CDR-L1 comprising the amino acid sequence set forth in SEQ ID NO:36; (2) a CDR-L2 comprising the amino acid sequence set forth in SEQ ID NO: 42; and (3) a CDR-L3 comprising the amino acid sequence set forth in SEQ ID NO:45, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:60.

In other embodiments, the anti-PD-L1 antibody of the invention, i.e., the PL3 antibody, comprises a light chain (LC) variable domain sequence comprising (1) a CDR-L1 comprising the amino acid sequence set forth in SEQ ID NO:37; (2) a CDR-L2 comprising the amino acid sequence set forth in SEQ ID NO: 41; and (3) a CDR-L3 comprising the amino acid sequence set forth in SEQ ID NO:46, and a heavy chain (HC) variable domain sequence comprising (1) a CDR-H1 comprising the amino acid sequence set forth in SEQ ID NO:53; (2) a CDR-H2 comprising the amino acid sequence set forth in SEQ ID NO:55; and (3) a CDR-H3 comprising the amino acid sequence set forth in SEQ ID NO:61.

In other embodiments, the anti-PD-L1 antibody of the invention, i.e., the PL6 antibody, comprises a light chain (LC) variable domain sequence comprising (1) a CDR-L1 comprising the amino acid sequence set forth in SEQ ID NO:37; (2) a CDR-L2 comprising the amino acid sequence set forth in SEQ ID NO: 41; and (3) a CDR-L3 comprising the amino acid sequence set forth in SEQ ID NO:47, and a heavy chain (HC) variable domain sequence comprising (1) a CDR-H1 comprising the amino acid sequence set forth in SEQ ID NO:54; (2) a CDR-H2 comprising the amino acid sequence set forth in SEQ ID NO:57; and (3) a CDR-H3 comprising the amino acid sequence set forth in SEQ ID NO:62.

In other embodiments, the anti-PD-L1 antibody of the invention, i.e., the PL8 antibody, comprises a light chain (LC) variable domain sequence comprising (1) a CDR-L1 comprising the amino acid sequence set forth in SEQ ID NO:38; (2) a CDR-L2 comprising the amino acid sequence set forth in SEQ ID NO: 43; and (3) a CDR-L3 comprising the amino acid sequence set forth in SEQ ID NO:48, and a heavy chain (HC) variable domain sequence comprising (1) a CDR-H1 comprising the amino acid sequence set forth in SEQ ID NO:51; (2) a CDR-H2 comprising the amino acid sequence set forth in SEQ ID NO:58; and (3) a CDR-H3 comprising the amino acid sequence set forth in SEQ ID NO:63.

In other embodiments, the anti-PD-L1 antibody of the invention, i.e., the PL12 antibody, comprises a light chain (LC) variable domain sequence comprising (1) a CDR-L1 comprising the amino acid sequence set forth in SEQ ID NO:39; (2) a CDR-L2 comprising the amino acid sequence set forth in SEQ ID NO: 41; and (3) a CDR-L3 comprising the amino acid sequence set forth in SEQ ID NO:49, and a heavy chain (HC) variable domain sequence comprising (1) a CDR-H1 comprising the amino acid sequence set forth in SEQ ID NO:51; (2) a CDR-H2 comprising the amino acid sequence set forth in SEQ ID NO:55; and (3) a CDR-H3 comprising the amino acid sequence set forth in SEQ ID NO:64.

In other embodiments, the anti-PD-L1 antibody of the invention, i.e., the PL15 antibody, comprises a light chain (LC) variable domain sequence comprising (1) a CDR-L1 comprising the amino acid sequence set forth in SEQ ID NO:40; (2) a CDR-L2 comprising the amino acid sequence set forth in SEQ ID NO: 41; and (3) a CDR-L3 comprising the amino acid sequence set forth in SEQ ID NO:50, and a heavy chain (HC) variable domain sequence comprising (1) a CDR-H1 comprising the amino acid sequence set forth in SEQ ID NO:53; (2) a CDR-H2 comprising the amino acid sequence set forth in SEQ ID NO:55; and (3) a CDR-H3 comprising the amino acid sequence set forth in SEQ ID NO:61.

The invention provides that the heavy and light chain variable domains and CDRs noted herein are combined in all possible pair-wise combinations to generate a number of anti-PD-L1 antibodies.

In certain embodiments, the amino acid substitution(s) are conservative amino acid substitution(s). In certain embodiments, the amino acid substitutions do not substantially reduce the ability of the antibody to bind antigen. For example, conservative alterations (e.g., conservative substitutions as provided herein) that do not substantially reduce PD-L1 binding affinity may be made. The binding affinity of anti-PD-L1 antibody variants can be assessed using methods described in the Examples below.

Conservative substitutions are shown in Table 3 under the heading of "conservative substitutions." More substantial changes are provided in Table 3 under the heading of "exemplary substitutions," and as further described below in reference to amino acid side chain classes. Amino acid substitutions may be introduced into an antibody of interest and the products screened for a desired activity, e.g., retained/improved PD-L1 binding, decreased immunogenicity, or improved ADCC or CDC.

TABLE 3

CONSERVATIVE SUBSTITITIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Non-conservative substitutions will entail exchanging a member of one of these classes for another class. An exemplary substitutional variant is an affinity matured antibody, which may be conveniently generated, e.g., using phage display based affinity maturation techniques such as those described herein. Briefly, one or more CDR residues are mutated and the variant antibodies displayed on phage and screened for a particular biological activity (e.g. binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling.

The invention further provides anti-PD-L1 antibody variants and/or mutants, or their antigen binding fragments thereof. In certain embodiments, the anti-PD-L1 antibody variant and/or mutants of the invention, i.e., the PL2 #3 antibody, comprises a light chain (LC) variable domain sequence comprising (1) a CDR-L1 comprising the amino acid sequence set forth in SEQ ID NO:65; (2) a CDR-L2 comprising the amino acid sequence set forth in SEQ ID NO: 42; and (3) a CDR-L3 comprising the amino acid sequence set forth in SEQ ID NO:71, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:77.

In other embodiments, the anti-PD-L1 antibody variant and/or mutants of the invention, i.e., the PL3 #7 antibody, comprises a light chain (LC) variable domain sequence comprising (1) a CDR-L1 comprising the amino acid sequence set forth in SEQ ID NO:37; (2) a CDR-L2 comprising the amino acid sequence set forth in SEQ ID NO: 41; and (3) a CDR-L3 comprising the amino acid sequence set forth in SEQ ID NO:72, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:55; and (3) a CDR-H3 comprising the amino acid sequence set forth in SEQ ID NO:78.

In other embodiments, the anti-PD-L1 antibody variant and/or mutants of the invention, i.e., the PL3 #7-19 antibody, comprises a light chain (LC) variable domain sequence comprising (1) a CDR-L1 comprising the amino acid sequence set forth in SEQ ID NO:66; (2) a CDR-L2 comprising the amino acid sequence set forth in SEQ ID NO:68; and (3) a CDR-L3 comprising the amino acid sequence set forth in SEQ ID NO:73, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:55; and (3) a CDR-H3 comprising the amino acid sequence set forth in SEQ ID NO:79. In certain embodiments, a mutant of the anti-PD-L1 antibody PL3 #7-19 comprises CDR-L2 comprising one or more mutations at the N-glycosylation sites. In certain embodiment, the glycosylation sites are within the CDR-L2 region, e.g., at the sequon N—X—S/T. The anti-PD-L1 antibody with one or more mutant on the sequon N—X—S/T eliminates the N-glycosylation site but remains the equal function.

In other embodiments, the anti-PD-L1 antibody variant and/or mutants of the invention, i.e., the PL3 #7-43 antibody, comprises a light chain (LC) variable domain sequence comprising (1) a CDR-L1 comprising the amino acid sequence set forth in SEQ ID NO:35; (2) a CDR-L2 comprising the amino acid sequence set forth in SEQ ID NO:69; and (3) a CDR-L3 comprising the amino acid sequence set forth in SEQ ID NO:74, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:55; and (3) a CDR-H3 comprising the amino acid sequence set forth in SEQ ID NO:80. In certain embodiments, a mutant of the anti-PD-L1 antibody PL3 #7-43 comprises CDR-L2 comprising one or more mutations at the N-glycosylation sites. In certain embodiment, the glycosylation sites are within the CDR-L2 region, e.g., at the sequon N—X—S/T. The anti-PD-L1 antibody with one or more mutant on the sequon N—X—S/T eliminates the N-glycosylation site but remains the equal function.

In other embodiments, the anti-PD-L1 antibody variant and/or mutants of the invention, i.e., the PL3 #7-54 antibody, comprises a light chain (LC) variable domain sequence comprising (1) a CDR-L1 comprising the amino acid sequence set forth in SEQ ID NO:67; (2) a CDR-L2 comprising the amino acid sequence set forth in SEQ ID NO:70; and (3) a CDR-L3 comprising the amino acid sequence set forth in SEQ ID NO:72, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:76; and (3) a CDR-H3 comprising the amino acid sequence set forth in SEQ ID NO:81.

In other embodiments, the anti-PD-L1 antibody variant and/or mutants of the invention, i.e., the PL2 #4 antibody, comprises a light chain (LC) variable domain sequence comprising (1) a CDR-L1 comprising the amino acid sequence set forth in SEQ ID NO:94; (2) a CDR-L2 comprising the amino acid sequence set forth in SEQ ID NO:42; and (3) a CDR-L3 comprising the amino acid sequence set forth in SEQ ID NO:95, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:96.

In other embodiments, the anti-PD-L1 antibody variant and/or mutants of the invention, i.e., the PL2 #5 antibody, comprises a light chain (LC) variable domain sequence comprising (1) a CDR-L1 comprising the amino acid sequence set forth in SEQ ID NO:97; (2) a CDR-L2 comprising the amino acid sequence set forth in SEQ ID NO:42; and (3) a CDR-L3 comprising the amino acid sequence set forth in SEQ ID NO:98, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:99.

In other embodiments, the anti-PD-L1 antibody variant and/or mutants of the invention, i.e., the PL2 #39 antibody, comprises a light chain (LC) variable domain sequence comprising (1) a CDR-L1 comprising the amino acid sequence set forth in SEQ ID NO:100; (2) a CDR-L2 comprising the amino acid sequence set forth in SEQ ID NO:42; and (3) a CDR-L3 comprising the amino acid sequence set forth in SEQ ID NO:95, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:101.

In other embodiments, the anti-PD-L1 antibody variant and/or mutants of the invention, i.e., the PL3 #1 antibody, comprises a light chain (LC) variable domain sequence comprising (1) a CDR-L1 comprising the amino acid sequence set forth in SEQ ID NO:37; (2) a CDR-L2 comprising the amino acid sequence set forth in SEQ ID NO:106; and (3) a CDR-L3 comprising the amino acid sequence set forth in SEQ ID NO:107, and a heavy chain (HC) variable domain sequence comprising (1) a CDR-H1 comprising the amino acid sequence set forth in SEQ ID NO:108; (2) a CDR-H2 comprising the amino acid sequence set forth in SEQ ID NO:55; and (3) a CDR-H3 comprising the amino acid sequence set forth in SEQ ID NO:109.

The invention provides that the heavy and light chain variable domains and CDRs noted herein are combined in all possible pair-wise combinations to generate a number of anti-PD-L1 antibody variants.

In certain embodiments, the invention provides that the anti-PD-L1 antibody, the variant or the antigen binding fragment thereof, comprises a light chain variable domain (VL) sequence comprising (1) a CDR-L1 comprising an amino acid sequence selected from the group consisting of SEQ ID Nos: 35-40, 65-67, 94, 97, and 100; (2) a CDR-L2 comprising an amino acid sequence selected from the group consisting of SEQ ID Nos: 41-43, 68-70 and 106; (3) a CDR-L3 comprising an amino acid sequence selected from the group consisting of SEQ ID Nos: 44-50, 71-74, 95, 98, and 107 and a heavy chain variable domain sequence ($V_H$) comprising (1) a CDR-H1 comprising an amino acid sequence selected from the group consisting of SEQ ID Nos: 51-54, 75, and 108; (2) a CDR-H2 comprising an amino acid sequence selected from the group consisting of SEQ ID Nos: 55-58 and 76; and (3) a CDR-H3 comprising an amino acid sequence selected from the group consisting of SEQ ID Nos: 59-64, 77-81, 96, 99, 101, and 109. The heavy and light chain variable domains are combined in all possible pair-wise combinations to generate a number of anti-PD-L1 antibodies.

Also provided by the invention are anti-PD-L1 antibodies, their variants and/or mutants, or antigen binding fragments thereof, comprising a light chain (LC) variable domain sequence comprising the amino acid sequence set forth in SEQ ID NOs: 1-7, 16, 20, 24, 28, 32, 83, 87, 91, or 103; and a heavy chain (HC) variable domain sequence comprising the amino acid sequence set forth in SEQ ID Nos: 8-14, 18, 22, 26, 30, 34, 85, 89, 93, or 105. Nucleic acid sequences encoding these LC and HC domains are also provided. The heavy and light chain variable domains are combined in all possible pair-wise combinations to generate a number of anti-PD-L1 antibodies and/or the variants thereof.

In certain embodiments, the anti-PD-L1 antibody, the variant or mutant, or antigen binding fragment thereof, may lack an N-glycosylation motif in the heavy chain or light chain variable region that can cause differences within a batch of antibodies resulting in altered function, immunogenicity, or stability. Methods of analyzing antibody glycosylation include, but are not limited to, e.g., chromatography (such as cation exchange chromatography (CEX) or liquid chromatography), mass spectrometry (such as electrospray ionization mass spectrometry), and capillary electrophoresis-sodium dodecyl sulfate. Such methods are described in, e.g., Jung et al. (2011) Curr Op Biotechnol. 22(6):858-67; Cummings R D, Etzler M E. Antibodies and Lectins in Glycan Analysis. In: Varki A, Cummings R D, Esko J D, et al., editors. Essentials of Glycobiology. 2nd edition. Cold Spring Harbor (N.Y.): Cold Spring Harbor Laboratory Press; 2009. Chapter 45; Mulloy B, Hart G W, Stanley P. Structural Analysis of Glycans. In: Varki A, Cummings R D, Esko J D, et al., editors. Essentials of Glycobiology. 2nd edition. Cold Spring Harbor (N.Y.): Cold Spring Harbor Laboratory Press; 2009. Chapter 47; Leymarie, et al. (2012) Anal Chem. 84(7): 3040-3048; Fernandez (2005) European Biopharmaceutical Review. pp 106-110; and Raju, T. (2013) Methods Mol Biol. 988: 169-180.

In certain embodiments, the anti-PD-L1 antibody, the variant and/or mutant, or antigen binding fragment thereof, has a stronger binding affinity for PD-L1 ligand than it has for a homologue of that PD-L1. Normally, the anti-PD-L1 antibody, and/or the variant or antigen binding fragment thereof, "binds specifically" to PD-L1 (i.e., has a binding affinity (Kd) value of no more than about $1\times10^{-7}$ M, preferably no more than about $1\times10^{-8}$ and most preferably no more than about $1\times10^{-9}$ M) but has a binding affinity for a member of the PD-L1 family that is at least about 50-fold, or at least about 500-fold, or at least about 1000-fold weaker than its binding affinity for PD-L1. The anti-PD-L1 antibody that binds specifically to PD-L1 can be of any of the various types of antibodies as defined above but preferably is a humanized or human antibody.

In some embodiments, the extent of binding of the anti-PD-L1 antibody to a non-target protein is less than about 10% of the binding of the antibody to PD-L1 as determined by methods known in the art, such as ELISA, fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., such as an anti-PD-L1 antibody and/or an affinity variant described herein). In some embodiments, the anti-PD-L1 antibody and/or the affinity variant exhibits similar antibody-dependent cell-mediated cytotoxicity (ADCC) effector function as the reference anti-PD-L1 monoclonal antibodies, as demonstrated by, e.g., assays described in the Examples.

For example, in certain embodiments, ADCC effector function activity of an anti-PD-L1 antibody and/or its affinity variant or mutant described herein is at least about 80%, at least about 85%, at least about 90%, at least about 91%, at least about 92%, at least about 93%, at least about 94%, at least about 95%, at least about 96%, at least about 97%, at least about 98%, at least about 99%, at least about 100%, or more than 100% (e.g., about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, or about 130%) of the ADCC effector function activity of the reference anti-PD-L1 antibody including any range between these values.

In certain embodiments, the anti-PD-L1 antibody and/or its affinity variant or mutant exhibits similar binding affinity for PD-L1 as the reference anti-PD-L1 antibody. In certain embodiments, binding to PD-L1 is demonstrated by ELISA, as described in the Examples. For example, the binding affinity of the anti-PD-L1 and/or its affinity variant or mutant for PD-L1 is about 1%, about 5%, about 10%, about 15%, about 20%, about 30%, about 40%, about 50%, about 60%, about 70%, about 80%, about 90%, about 95% about 96%, about 97%, about 98%, about 99%, about 100%, or more than 100% higher (e.g., about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, or more than about 125%) than the binding affinity of the reference anti-PD-L1 antibody for PD-L1.

In certain embodiments, the anti-PD-L1 antibody and/or its affinity variant or mutant binds a human PD-L1 with a Kd between about 0.1 pM to 200 pM (0.2 nM), e.g., about 0.1 pM, about 0.25 pM, about 0.5 pM, about 0.75 pM, about 1 pM, about 5 pM, about 10p M, about 20 pM, about 30 pM, about 40 pM, about 50 pM, about 60 pM, about 70 pM, about 80 pM, about 90 pM, about 100 pM, about 110 pM, about 120 pM, about 130 pM, about 140 pM, about 150 pM, about 160 pM, about 170 pM, about 180 pM, about 190 pM, or more than about 190 pM, including any range between these values. In certain embodiments, the binding affinity of the anti-PD-L1 antibody and/or its affinity variant or mutant to PD-L1 is about 1%, about 5%, about 10%, about 15%, about 20%, about 30%, about 40%, about 50%, about 60%, about 70%, about 80%, about 90%, about 95% about 96%, about 97%, about 98%, about 99%, about 100%, or more than about 100% higher (e.g., about 105%, about 110%, about 120%, or about 130%) higher than the binding affinity of the reference anti-PD-L1 antibody to PD-L1. In certain embodiments, the binding affinity of the anti-PD-L1 and/or its variant or mutant to PD-L1 is about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.25-fold, about 2.5-fold, about 2.75 fold, about 3-fold, about 3.25-fold, about 3.5 fold, about 3.75-fold, about 4-fold, about 4.25-fold, about 4.5-fold, about 4.75-fold, or more than about 4.75-fold higher than the binding affinity of the reference anti-PD-L1 antibody to PD-1, including any range in between these values.

In certain embodiments, the anti-PD-L1 antibodies and their variants or mutants provided herein have prolonged in vivo half-lives as compared to the reference anti-PD-L1 antibody. In certain embodiments, the in vivo half-life of an anti-PD-L1 antibody and/or its variant or mutant described herein is no shorter than the in vivo half-life of the reference anti-PD-L1 antibody.

In certain embodiments, the anti-PD-L1 antibodies and their variants or mutants provided herein exhibit pharmacokinetic properties that are similar to those of the reference anti-PD-L1 antibodies. In certain embodiments, the anti-PD-L1 antibodies and their variants or mutants provided herein exhibit an AUC (area under curve) that is about 50%, about 55%, about 60%, about 65%, about 70%, about 75%, about 80%, about 85%, about 90%, about 95%, or greater than 95% (such as about 96%, about 97%, about 98%, about 99%, or more than about 99%) of the serum concentration-time profiles of the reference anti-PD-L1 antibody, including any range between these values.

In certain embodiments, the antibody comprises an Fc sequence of a human IgG, e.g., human IgG1 or human IgG4. In certain embodiments, the Fc sequence has been altered or otherwise changed so that it lacks antibody dependent cellular cytotoxicity (ADCC) effector function, often related to their binding to Fc receptors (FcRs). There are many examples of changes or mutations to Fc sequences that can alter effector function. For example, WO 00/42072 and Shields et al. J Biol. Chem. 9(2): 6591-6604 (2001) describes antibody variants with improved or diminished binding to FcRs. The contents of those publications are specifically incorporated herein by reference. The antibody can be in the form of a Fab, Fab', a F(ab)'2, single-chain Fv (scFv), an Fv fragment; a diabody and a linear antibody. Also, the antibody and variants or mutants thereof can be a multispecific antibody or variant or mutant that binds to PD-L1, but also binds one or more other targets and inhibits their function. The antibody and/or the variant or mutant thereof can be conjugated to a therapeutic agent (e.g., cytotoxic agent, a radioisotope and a chemotherapeutic agent) or a label for detecting PD-L1 in patient samples or in vivo by imaging (e.g., radioisotope, fluorescent dye and enzyme). Other modifications include the conjugation of toxins to anti-PD-L1 antibodies and/or variants or mutants thereof provided herein.

Nucleic acid molecules encoding the anti-PD-L1 antibodies, variants and/or mutants thereof, expression vectors comprising nucleic acid molecules encoding the CDRs and/or a heavy chain variable domain and/or a light chain variable domain described herein, and cells comprising the nucleic acid molecules are also contemplated. These antibodies and variants or mutants thereof can be used in the therapies described herein and to detect PD-L1 protein in patient samples (e.g., via FACS, immunohistochemistry (IHC), ELISA assays) or in patients.

Monoclonal Antibodies

Monoclonal antibodies can be prepared, e.g., using hybridoma methods, such as those described by Kohler and Milstein, Nature, 256:495 (1975) or can be made by recombinant DNA methods (U.S. Pat. No. 4,816,567) or can be produced by the methods described herein in the Examples below. In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro.

The immunizing agent will typically include a polypeptide or a fusion protein of the protein of interest or a composition comprising the protein. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, MONOCLONAL ANTIBODIES: PRINCIPLES AND PRACTICE, New York: Academic Press, 1986, pp. 59-103) Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001 (1984); Brodeur et al. MONOCLONAL ANTIBODY PRODUCTION TECHNIQUES AND APPLICATIONS, Marcel Dekker, Inc.: New York, 1987, pp. 51-63).

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem. 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies provided herein can be readily isolated and sequenced using conventional procedures (e.g., by using oligonucleotide probes that are capable of binding specifically to genes encoding the heavy and light chains of murine antibodies). The hybridoma cells provided herein serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody provided herein, or can be substituted for the variable domains of one antigen-combining site of an antibody provided herein to create a chimeric bivalent antibody.

In certain embodiments, an anti-PD-L1 antibody and/or variant or mutant thereof provided by the invention is expressed by a stable mammalian cell line. In certain embodiments, an anti-PD-L1 antibody and/or variant or mutant thereof provided by the invention is expressed from a stable mammalian cell line at a titer of about 2.0 grams/liter, about 2.5 grams/liter, about 3.0 grams/liter, about 3.5 grams/liter, about 4.0 grams/liter, about 4.5 grams/liter, about 5.0 grams/liter, about 5.5 grams/liter, about 6 grams/liter, about 6.5 grams/liter, about 7.0 grams/liter, or more than about 7.0 grams/liter, including any range in between these values. In certain embodiments, the stable mammalian cell line from which an anti-PD-L1 antibody and/or variant or mutant thereof provided by the invention is expressed is a CHO cell line.

In certain embodiments, the antibodies are monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using, but not limited to, techniques known in the art.

Human and Humanized Antibodies

The antibodies (and/or variants) can be humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) that typically contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an immunoglobulin constant region (Fc), typically that of a human immunoglobulin. Jones et al. Nature, 321: 522-525 (1986); Riechmann et al., Nature, 332: 323-329 (1988); Presta, Curr. Op. Struct. Biol., 2:593-596 (1992).

Generally, a humanized antibody has one or more amino acid residues introduced into it from a source that is non-human. These non-human amino acid residues are often referred to as "import" residues, which are typically taken from an "import" variable domain. According to one embodiment, humanization can be essentially performed following the method of Winter and co-workers (Jones et al. Nature, 321: 522-525 (1986); Riechmann et al. Nature, 332: 323-327 (1988); Verhoeyen et al. Science, 239: 1534-1536 (1988)), by substituting rodent CDRs or CDR sequences for the corresponding sequences of a human antibody. Accordingly, such "humanized" antibodies are antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al. PNAS USA, 90:2551 (1993); Jakobovits et al., Nature, 362:255-258 (1993); Bruggemann et al. Year in Immunol., 7:33 (1993); U.S. Pat. Nos. 5,545,806, 5,569,825, 5,591,669; 5,545,807; and WO 97/17852.

Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., Bio/Technology, 10: 779-783 (1992); Lonberg et al., Nature, 368: 856-859 (1994); Morrison, Nature, 368: 812-813 (1994); Fishwild et al. Nature Biotechnology, 14: 845-851 (1996); Neuberger, Nature Biotechnology, 14: 826 (1996); Lonberg and Huszar, Intern. Rev. Immunol., 13: 65-93 (1995).

Alternatively, phage display technology (McCafferty et al., Nature 348:552-553, 1990) can be used to produce human antibodies and antibody fragments in vitro, from immunoglobulin variable (V) domain gene repertoires from unimmunized donors. According to one embodiment of this technique, antibody V domain sequences are cloned in frame into either a major or minor coat protein gene of a filamentous bacteriophage, such as M13 or fd, and displayed as functional antibody fragments on the surface of the phage particle. Phage display can be performed in a variety of formats, e.g., as described below in the Examples section or as reviewed in, e.g., Johnson, Kevin S. and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human antibodies can also be produced using various techniques known in the art, including phage display libraries. Hoogenboom and Winter, J. Mol. Biol., 227: 381 (1991); Marks et al., J. Mol. Biol., 222: 581 (1991). The techniques of Cole et al. and Boerner et al. are also available for the preparation of human monoclonal antibodies. Cole et al., Monoclonal Antibodies and Cancer Therapy, Alan R. Liss, p. 77 (1985) and Boerner et al., J. Immunol., 147(1): 86-95 (1991).

Multispecific Antibodies

Multispecific antibodies are monoclonal, preferably human or humanized, antibodies that have binding specificities for two or more different antigens (e.g., bispecific antibodies have binding specificities for at least two antigens). For example, one of the binding specificities can be for the a5~1 protein, the other one can be for any other antigen. According to one preferred embodiment, the other antigen is a cell-surface protein or receptor or receptor subunit. For example, the cell-surface protein can be a natural killer (NK) cell receptor. Thus, according to one embodiment, a bispecific antibody of this invention can bind both PD-L1 and, e.g., a second cell surface receptor.

Suitable methods for making bispecific antibodies are well known in the art. For example, the recombinant production of bispecific antibodies is based on the co-expression of two immunoglobulin heavy-chain/light-chain pairs, where the two heavy chains have different specificities. Milstein and Cuello, Nature, 305: 537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., EMBO, 10: 3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., Methods in Enzymology, 121: 210 (1986).

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., PNAS USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Heteroconjugate Antibodies

Heteroconjugate antibodies are composed of two covalently joined antibodies. Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody provided herein with respect to effector function, so as to enhance, e.g., the effectiveness of the antibody in treating cancer. For example, cysteine residue(s) can be introduced into the Fc region, thereby allowing inter-chain disulfide bond formation in this region. The homodimeric antibody thus generated can have improved internalization capability and/or increased complement-mediated cell killing and antibody-dependent cellular cytotoxicity (ADCC). See, Caron et al., J. Exp. Med., 176: 1191-1195 (1992) and Shapes, J. Immunol., 148: 2918-2922 (1992). Homodimeric antibodies with enhanced anti-tumor activity can also be prepared using heterobifunctional cross-linkers as described in Wolff et al., Cancer Research, 53: 2560-2565 (1993). Alternatively, an antibody can be engineered that has dual Fc regions and can thereby have enhanced complement lysis and ADCC capabilities. See, Stevenson et al., Anti-Cancer Drug Design 3: 219-230 (1989).

Mutations or alterations in the Fc region sequences can be made to improve FcR binding (e.g., FcγR, FcRn). According to one embodiment, an antibody of this invention has at least one altered effector function selected from the group consisting of ADCC, CDC, and improved FcRn binding compared to a native IgG or a parent antibody. Examples of several useful specific mutations are described in, e.g., Shields, R L et al. (2001) JBC 276(6)6591-6604; Presta, L. G., (2002) Biochemical Society Transactions 30(4):487-490; and WO 00/42072.

According to one embodiment, the Fc receptor mutation refers a substitution at least one position selected from the group consisting of: 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438 or 439 of the Fc region, wherein the numbering of the residues in the Fc region is according to the EU numbering system. In some embodiments, the Fc receptor mutation is a D265A substitution. In some embodiments, the Fc receptor mutation is a N297 A substitution. Additional suitable mutations are set forth in U.S. Pat. No. 7,332,581.

Immunoconjugates

The invention also pertains to immunoconjugates comprising an antibody, or variant or mutant thereof, conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Exemplary chemotherapeutic agents useful in the generation of such immunoconjugates include those described elsewhere herein.

In certain embodiments, an anti-PD-L1 antibody and/or variant or mutant thereof provided herein is conjugated to maytansine, a maytansinoid, or calicheamicin. In certain embodiments, an anti-PD-L1 antibody and/or variant or mutant thereof provided herein is conjugated to the maytansinoid DM1.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bisdiazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11026.

In another embodiment, the antibody, or variant or mutant thereof, can be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Covalent Modifications

Covalent modifications of the anti-PD-L1 antibodies, variants, mutants, and fragments thereof are included within the scope of this invention. One type of covalent modification includes reacting targeted amino acid residues of a polypeptide with an organic derivatizing agent that is capable of reacting with selected side chains or the N- or C-terminal residues of the polypeptide. Derivatization with bifunctional agents is useful, for instance, for crosslinking the polypeptide to a water-insoluble support matrix or surface for use in the method for purifying antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)-dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of the polypeptide comprises linking the polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

Chimeric Molecules

An anti-PD-L1 antibody, variant, mutant, and/or fragment thereof, of the present invention can also be modified if advantageous in a way to form a chimeric molecule comprising the polypeptide fused to another, heterologous polypeptide or amino acid sequence (e.g., immunoadhesins or peptibodies).

In one embodiment, such a chimeric molecule comprises a fusion of the polypeptide with a protein transduction domain that targets the polypeptide for delivery to various tissues and more particularly across the brain blood barrier, using, for example, the protein transduction domain of human immunodeficiency virus TAT protein (Schwarze et al., 1999, Science 285: 1569-72).

In another embodiment, such a chimeric molecule comprises a fusion of the polypeptide with a tag polypeptide that provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag. Various tag polypeptides and their respective antibodies are known in the art. Examples include polyhistidine (poly-His) or poly-histidine-glycine (poly-His-gly) tags; the flu HA tag polypeptide and its antibody 12CA5 (Field et al., Mol. Cell. Biol., 8:2159-2165 (1988)]; the c-myc tag and the 8F9, 3C7, 6E10, G4, B7 and 9E10 antibodies thereto (Evan et al., Molecular and Cellular Biology, 5:3610-3616 (1985)]; and the Herpes Simplex virus glycoprotein D (gD) tag and its antibody (Paborsky et al., Protein Engineering, 3(6):547-553 (1990)]. Other tag polypeptides include the Flag-peptide (Hopp et al., BioTechnology, 6:1204-1210 (1988)]; the KT3 epitope peptide (Martin et al., Science, 255:192-194 (1992)]; an α-tubulin epitope peptide (Skinner et al., J. Biol. Chem., 266:15163-15166 (1991)]; and the T7 gene 10 protein peptide tag (Lutz-Freyermuth et al., Proc. Natl. Acad. Sci. USA, 87:6393-6397 (1990)).

In an alternative embodiment, the chimeric molecule can comprise a fusion of the polypeptide with an immunoglobulin or a particular region of an immunoglobulin. For a bivalent form of the chimeric molecule (e.g., an "immunoadhesin"), such a fusion could be to the Fc region of an IgG molecule. Ig fusions of this invention include polypeptides that comprise approximately or only residues 94-243, residues 33-53 or residues 33-52 of human in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also, U.S. Pat. No. 5,428,130 issued Jun. 27, 1995.

Immunoliposomes

The antibodies disclosed herein can also be formulated as immunoliposomes. Liposomes containing the antibody are prepared by methods known in the art, such as described in Epstein et al., PNAS USA, 82: 3688 (1985); Hwang et al., PNAS USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction. An anti-neoplastic agent, a growth inhibitory agent, or a chemotherapeutic agent (such as doxorubicin) is optionally also contained within the liposome. See, Gabizon et al., J. National Cancer Inst., 81(19): 1484 (1989).

Treatment Using Anti-PD-L1 Antibodies and Variants Thereof

The anti-PD-L1 antibodies, variants, mutants, and/or fragments thereof, and/or compositions provided herein can be administered to subjects (e.g., mammals such as humans) to treat diseases and disorders involving abnormal PD-L1 activity, including, for example, cancer (such as head and neck cancer, throat cancer, colorectal cancer, lung cancer, etc.). In certain embodiments, the invention provides anti-PD-L1 antibodies and/or variants described herein (or fragments thereof) for use in the manufacture of a medicament for the treatment of cancer (such as melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) in a subject. In certain embodiments, the invention provides anti-PD-L1 antibodies and/or variants described herein (or fragments thereof) for use in treating cancer (such as melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) in a subject.

In certain embodiments, the invention provides pharmaceutical compositions comprising an anti-PD-L1 antibody and/or its variant or mutant provided herein (or fragments thereof) for use in treating cancer (melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) in a subject. In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is a clinical patient, a clinical trial volunteer, an experimental animal, etc. In certain embodiments, the subject is suspected of having or at risk for having a cancer (such as melanoma, NSCLC, head and neck cancer, urothelial cancer, breast cancer (e.g, triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) or be diagnosed with a cancer or any other disease having abnormal PD-L1 expression or activity.

Many diagnostic methods for cancer (such as melanoma, NSCLC, head and neck cancer, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) or any other disease exhibiting abnormal PD-L1 activity and the clinical delineation of those diseases are known in the art. Such methods include, but are not limited to, e g, immunohistochemistry, PCR, fluorescent in situ hybridization (FISH). Additional details regarding diagnostic methods for abnormal PD-L1 activity or expression are described in, e.g., Gupta et al. (2009) Mod Pathol. 22(1): 128-133; Lopez-Rios et al. (2013) J Clin Pathol. 66(5): 381-385; Ellison et al. (2013) J Clin Pathol 66(2): 79-89; and Guha et al. (2013) PLoS ONE 8(6): e67782.

Administration can be by any suitable route including, e.g., intravenous, intramuscular, or subcutaneous. In some embodiments, the anti-PD-L1 antibodies and/or variants or mutants (or fragments thereof) and/or compositions provided herein are administered in combination with a second, third, or fourth agent (including, e.g., an antineoplastic agent, a growth inhibitory agent, a cytotoxic agent, or a chemotherapeutic agent) to treat the diseases or disorders involving abnormal PD-L1 activity. Such agents include, e.g., docetaxel, gefitinib, FOLFIRI (irinotecan, 5-fluorouracil, and leucovorin), irinotecan, cisplatin, carboplatin, paclitaxel, bevacizumab (anti-VEGF antibody), FOLFOX-4, infusional fluorouracil, leucovorin, and oxaliplatin, afatinib, gemcitabine, capecitabine, pemetrexed, tivantinib, everolimus, CpG-ODN, rapamycin, lenalidomide, vemurafenib, endostatin, lapatinib, PX-866, Imprime PGG, and irlotinibm. In some embodiments, the anti-PD-L1 antibodies and/or variants (or fragments thereof) are conjugated to the additional agent.

In certain embodiments, the anti-PD-L1 antibodies and/or variants or mutants (or fragments thereof) and/or compositions provided herein are administered in combination with one or more additional therapies, such as radiation therapy, surgery, chemotherapy, and/or targeted therapy. In certain embodiments, the anti-PD-L1 antibodies and/or variants (or fragments thereof) and/or compositions provided herein are administered in combination with radiation therapy. In certain embodiments, the combination of an anti-PD-L1 antibody and/or variant (or fragment thereof) and/or composition provided herein and radiation therapy is used for treating a cancer selected from the group consisting of melanoma, NSCLC, head and neck cancer, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, and thyroid cancer.

Depending on the indication to be treated and factors relevant to the dosing that a physician skilled in the field would be familiar with, the anti-PD-L1 antibodies, variants, mutants, or fragments thereof, provided herein will be administered at a dosage that is efficacious for the treatment of that indication while minimizing toxicity and side effects. For the treatment of a cancer (such as melanoma, NSCLC, head and neck cancer, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer), a typical dose can be, for example, in the rage of 0.001 to 1000 µg; however, doses below or above this exemplary range are within the scope of the invention. The daily dose can be about 0.1 µg/kg to about 100 mg/kg of total body weight (e.g., about 5 µg/kg, about 10 µg/kg, about 100 µg/kg, about 500 µg/kg, about 1 mg/kg, about 50 mg/kg, or a range defined by any two of the foregoing values), preferably from about 0.3 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 1 mg/kg of total body weight (e.g., about 3 µg/kg, about 15 µg/kg, about 75 µg/kg, about 300 µg/kg, about 900 µg/kg, or a range defined by any two of the foregoing values), and even more preferably from about 0.5 to 10 mg/kg body weight per day (e.g., about 2 mg/kg, about 4 mg/kg, about 7 mg/kg, about 9 mg/kg, or a range defined by any two of the foregoing values, including any range between the foregoing values). As noted above, therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

A pharmaceutical composition comprising the anti-PD-L1 antibody, variant, mutant, or a fragment thereof can be administered one, two, three, or four times daily. The compositions can also be administered less frequently than daily, for example, six times a week, five times a week, four times a week, three times a week, twice a week, once a week, once every two weeks, once every three weeks, once every month, once every two months, once every three months, or once every six months. The compositions may also be administered in a sustained release formulation, such as in an implant that gradually releases the composition for use over a period of time, and that allows for the composition to be administered less frequently, such as once a month, once every 2-6 months, once every year, or even a single administration. The sustained release devices (such as pellets, nanoparticles, microparticles, nanospheres, microspheres, and the like) may be administered by injection.

The antibody and/or variant or mutant (or a fragment thereof) may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once every month, once every two months, once every three months, or once every six months. The antibody (or a fragment thereof) may also be administered in a sustained release formulation, such as in an implant that gradually releases the composition for use over a period of time, and that allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgically implanted in various locations.

Cancer treatments can be evaluated by, e.g., but not limited to, tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation $100-(T/C \times 100)$, where T is the mean relative tumor volume of the treated tumor, and C is the mean relative tumor volume of a non-treated tumor. In certain embodiments, the % TGI is about 10%, about 20%, about 30%, about 40%, about 50%, about 60%, about 70%, about 80%, about 90%, about 91%, about 92%, about 93%, about 94%, about 95%, or more than 95%. In certain embodiments the % TGI of an anti-PD-L1 and/or its variant or mutant is the same as or greater than the % TGI of the reference anti-PD-L1 antibody, such as about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, including any range in between these values, or more than about 2.7-fold greater than the % TGI of the reference anti-PD-L1 antibody.

Pharmaceutical Formulations

The anti-PD-L1 antibodies and/or variants or mutants (or fragments thereof) can be formulated with suitable carriers or excipients so that they are suitable for administration. Suitable formulations of the antibodies are obtained by mixing an antibody (or fragment thereof) having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Exemplary antibody formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent. Such molecules are suitably present in combination in amounts that are effective for the purpose intended. The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages. The active ingredients may also be entrapped in microcapsules prepared, for example, by coacervation techniques or by interfacial polymerization, for example, hydroxymethyl-cellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Sustained-release preparations may be prepared. Suitable examples of sustained-release preparations include semi-permeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and. ethyl-L-glutamate, non-degradable ethylene-vinyl, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Lipofectins or liposomes can be used to deliver the polypeptides and antibodies (or fragments thereof) or compositions of this invention into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., PNAS USA, 90: 7889-7893 (1993).

The active ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's PHARMACEUTICAL SCIENCES, supra.

Sustained-release preparations can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydro gels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In certain embodiments, the formulation comprises an anti-PD-L1 antibody and/or its variant or mutant described herein at a concentration of greater than about 0.5 mg/ml, greater than about 1 mg/ml, greater than about 2 mg/ml, greater than about 3 mg/ml, greater than about 4 mg/ml, greater than about 5 mg/ml, greater than about 6 mg/ml, greater than about 7 mg/ml, greater than about 8 mg/ml, greater than about 9 mg/ml, greater than about 10 mg/ml, greater than about 11 mg/ml, greater than about 12 mg/ml, greater than about 13 mg/ml, greater than about 14 mg/ml, greater than about 15 mg/ml, greater than about 16 mg/ml, greater than about 17 mg/ml, greater than about 18 mg/ml, greater than about 19 mg/ml, greater than about 20 mg/ml, greater than about 21 mg/ml, greater than about 22 mg/ml, greater than about 23 mg/ml, greater than about 24 mg/ml, greater than about 25 mg/ml, greater than about 26 mg/ml, greater than about 27 mg/ml, greater than about 28 mg/ml, greater than about 29 mg/ml, or greater than about 30 mg/ml, including any range in between these values.

In certain embodiments, the anti-PD-L1 antibody and/or variant or mutant thereof is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) in a buffer comprising a citrate, NaCl, acetate, succinate, glycine, polysorbate 80 (Tween 80), or any combination of the foregoing. In certain embodiments, the anti-PD-L1 antibody and/or variant thereof is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) in a buffer comprising about 100 mM to about 150 mM glycine. In certain embodiments, the anti-PD-L1 antibody and/or variant thereof is formulated in a buffer comprising about 50 mM to about 100 mM NaCl. In certain embodiments, the anti-PD-L1 antibody and/or variant or mutant thereof is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg·ml, including any range in between these values) in a buffer comprising about 10 mM to about 50 mM acetate. In certain embodiments, the anti-PD-L1 antibody and/or variant thereof is formulated in a buffer comprising about 10 mM to about 50 mM succinate. In certain embodiments, the anti-PD-L1 antibody and/or variant or mutant thereof is formulated (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) in a buffer comprising about 0.005% to about 0.02% polysorbate 80. In certain embodiments, the anti-PD-L1 antibody and/or variant or mutant thereof is formulated in a buffer having a pH between about 5.1 and 5.6. In certain embodiments, the anti-PD-L1 antibody and/or variant or mutant thereof is formulated in a buffer comprising 10 mM citrate, 100 mM NaCl, 100 mM glycine, and 0.01% polysorbate 80, wherein the formulation is at pH=5.5.

In certain embodiments, a formulation (such as a formulation comprising buffer comprising 10 mM citrate, 100 mM NaCl, 100 mM glycine, and 0.01% polysorbate 80, wherein the formulation is at pH=5.5) comprising an anti-PD-L1 antibody and/or variant or mutant thereof described herein (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) is stable at room temperature (such as at about 20-25° C.) for about 0.5 weeks, 1.0 weeks, 1.5 weeks, 2.0 weeks, 2.5 weeks, 3.5 weeks, 4.0 weeks, 4.5 weeks, or 5.0 weeks, including any range in between these values. In certain embodiments, a formulation (such as a formulation comprising buffer comprising 10 mM citrate, 100 mM NaCl, 100 mM glycine, and 0.01% polysorbate 80, wherein the formulation is at pH=5.5) comprising an anti-PD-L1 antibody and/or variant or mutant thereof described herein (e.g., at a concentration greater than about 0.5 mg/ml, greater than about 1 mg/ml, greater than about 5 mg/ml, greater than about 10 mg/ml, greater than about 15 mg/ml, greater than about 20 mg/ml, or greater than about 25 mg/ml, including any range in between these values) is stable under accelerated conditions (such as storage at about 37° C.) for about 0.5 weeks, 1.0 weeks, 1.5 weeks, 2.0 weeks, 2.5 weeks, 3.5 weeks, 4.0 weeks, 4.5 weeks, or 5.0 weeks, including any range in between these values.

Size exclusion chromatography (SEC) is a well-known and widely used method used in protein stability studies to detect potential fragmentation and aggregation, corresponding to physical and chemical instabilities. In certain embodiments, a formulation comprising 5 mg/ml, 10 mg/ml, 15 mg/ml, 20 mg/ml, or 25 mg/ml of an anti-PD-L1 antibody and/or variant or mutant thereof described herein shows less than about a 1.6%, 1.4%, 1.2%, 1.0%, 0.8%, 0.6%, 0.4%, 0.2%, or 0.1% increase in high molecular weight species (HMWS) after 1 week at 37° C., relative to the initial % high molecular weight species, as measured using SEC, including any range in between these values. In certain embodiments, a formulation comprising 5 mg/ml, 10 mg/ml, 15 mg/ml, 20 mg/ml, or 25 mg/ml of an anti-PD-L1 antibody described herein shows less than about a 2.0%, 1.8% 1.6%, 1.4%, 1.2%, 1.0%, 0.8%, 0.6%, 0.4%, 0.2%, or 0.1% increase in high molecular weight species after 2 weeks at 37° C., relative to the initial % high molecular weight species, as measured using SEC, including any range in between these values. In certain embodiments, a formulation comprising 5 mg/ml, 10 mg/ml, 15 mg/ml, 20 mg/ml, or 25 mg/ml of an anti-PD-L1 antibody and/or variant or mutant thereof described herein shows less than about a 3.3%, 3.2%, 3.1%, 3.0%, 2.9%, 2.8%, 2.7%, 2.6%, 2.5%, 2.4%, 2.2%, 2.0%, 1.8% 1.6%, 1.4%, 1.2%, 1.0%, 0.8%, 0.6%, 0.4%, 0.2%, or 0.1% increase in high molecular weight species after 4 weeks at 37° C., relative to the initial % high molecular weight species, as measured using SEC, including any range in between these values.

In certain embodiments, a formulation comprising 5 mg/ml, 10 mg/ml, 15 mg/ml, 20 mg/ml, or 25 mg/ml of an anti-PD-L1 antibody and/or variant or mutant thereof described herein shows less than about a 1.6%, 1.4%, 1.2%, 1.0%, 0.8%, 0.6%, 0.4%, 0.2%, or 0.1% increase in low molecular weight species (LMWS) after 1 week at 37° C., relative to the initial % low molecular weight species, as measured using SEC, including any range in between these values. In certain embodiments, a formulation comprising 5 mg/ml, 10 mg/ml, 15 mg/ml, 20 mg/ml, or 25 mg/ml of an anti-PD-L1 antibody and/or variant or mutant thereof described herein shows less than about a 2.0%, 1.8% 1.6%, 1.4%, 1.2%, 1.0%, 0.8%, %, 0.4%, 0.2%, or 0.1% increase in low molecular weight species after 2 weeks at 37° C., relative to the initial % low molecular weight species, as measured using SEC, including any range in between these values. In certain embodiments, a formulation comprising 5 mg/ml, 10 mg/ml, 15 mg/ml, 20 mg/ml, or 25 mg/ml of an anti-PD-L1 antibody and/or variant or mutant thereof described herein shows less than about a 2.4%, 2.2%, 2.0%, 1.8% 1.6%, 1.4%, 1.2%, 1.0%, 0.8%, 0.6%, 0.4%, 0.2%, or 0.1% increase in low molecular weight species after 4 weeks at 37° C., relative to the initial % low molecular weight species, as measured using SEC, including any range in between these values.

In certain embodiments, a formulation comprising 5 mg/ml, 10 mg/ml, 15 mg/ml, 20 mg/ml, or 25 mg/ml of an anti-PD-L1 antibody and/or variant or mutant thereof described herein shows no more about a 0.2%, 0.4%, 0.6%, 0.8%, 0.9%, 1.0%, 1.1%, 1.2%, 1.3%, 1.4%, 1.6%, 1.7%, 1.8%, 1.9%, 2%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 1 week at 37° C., relative to the initial % monomer, as measured using SEC, including any range in between these values. In certain embodiments, a formulation comprising 5 mg/ml, 10 mg/ml, 15 mg/ml, 20 mg/ml, or 25 mg/ml of an anti-PD-L1 antibody and/or variant or mutant thereof described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 2 weeks at 37° C., relative to the initial % monomer, as measured using SEC, including any range in between these values. In certain embodiments, a formulation comprising 5 mg/ml, 10 mg/ml, 15 mg/ml, 20 mg/ml, or 25 mg/ml of an anti-PD-L1 antibody and/or variant or mutant thereof described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 2 weeks at 37° C., relative to the initial % monomer, as measured using SEC, including any range in between these values.

Cation exchange chromatography (CEX) is a well-known and widely used tool to detect protein degradation events such as deamidation or oxidation (Moorhouse et al. (1997) J. Pharm. Biomed. Anal. 16, 593-603). Degradation products are typically referred to as acidic or basic species. Acidic species are the variants that elute earlier than the main peak from CEX, while basic species are the variants that elute later than the main peak from CEX. In certain embodiments, the acidic peak fraction of a formulation comprising 5 mg/ml, 10 mg/ml, 15 mg/ml, 20 mg/ml, or 25 mg/ml of an anti-PD-L1 antibody and/or variant or mutant thereof described herein is no more than about 7%, 8%, 9%, 10%, 11%, 12%, 13%, 14%, or 15% of total protein after 1 week at 37° C., as measured using CEX, including any range in between these values. In certain embodiments, the acidic peak fraction of a formulation comprising 5 mg/ml, 10 mg/ml, 15 mg/ml, 20 mg/ml, or 25 mg/ml of an anti-PD-L1 antibody and/or variant or mutant thereof described herein is no more than about 8%, 9%, 10%, 11%, 12%, 13%, 14%, 15%, 16%, 17%, or 18% of total protein after 2 weeks at 37° C., as measured using CEX, including any range in between these values. In certain embodiments, the acidic peak fraction of a formulation comprising 5 mg/ml, 10 mg/ml, 15 mg/ml, 20 mg/ml, or 25 mg/ml of an anti-PD-L1 antibody and/or variant or mutant (or fragment) thereof described herein is no more than about 8%, 9%, 10%, 11%, 12%, 13%, 14%, 15%, 16%, 17%, 18%, 19%, 20%, 21%, 22%, 23%, 24%, 25%, 26%, or 27% of total protein after 2 weeks at 37° C., as measured using CEX, including any range in between these values.

In certain embodiments, the basic peak fraction of a formulation comprising 5 mg/ml, 10 mg/ml, 15 mg/ml, 20 mg/ml, or 25 mg/ml of an anti-PD-L1 antibody and/or variant or mutant (or fragment) thereof described herein is no more than about 39%, 40%, 41%, 42%, 43%, 44%, 45%, or 46% of total protein after 1 week at 37° C., as measured using CEX, including any range in between these values. In certain embodiments, the basic peak fraction of a formulation comprising 5 mg/ml, 10 mg/ml, 15 mg/ml, 20 mg/ml, or 25 mg/ml of an anti-PD-L1 antibody and/or variant or mutant (or fragment) thereof described herein is no more than about 39%, 40%, 41%, 42%, 43%, 44%, 45%, or 46% of total protein after 2 weeks at 37° C., as measured using CEX, including any range in between these values. In certain embodiments, the basic peak fraction of a formulation comprising 5 mg/ml, 10 mg/ml, 15 mg/ml, 20 mg/ml, or 25 mg/ml of an anti-PD-L1 antibody and/or variant or mutant (or fragment) thereof described herein is no more than about 39%, 40%, 41%, 42%, 43%, 44%, 45%, or 46% of total protein after 4 weeks at 37° C., as measured using CEX, including any range in between these values.

In certain embodiments, the main peak fraction of a formulation comprising 5 mg/ml, 10 mg/ml, 15 mg/ml, 20 mg/ml, or 25 mg/ml of an anti-PD-L1 antibody and/or variant or mutant (or fragment) thereof described herein is no less than about 32%, 33%, 34%, 35%, 36%, 37%, 38%, 39%, 40%, 41%, 42%, 43%, 44%, 45%, or 46% of total protein after 1 week at 37° C., as measured using CEX, including any range in between these values. In certain embodiments, the basic peak fraction of a formulation comprising 5 mg/ml, 10 mg/ml, 15 mg/ml, 20 mg/ml, or 25 mg/ml of an anti-PD-L1 antibody and/or variant or mutant (or fragment) thereof described herein is no less than about 32%, 33%, 34%, 35%, 36%, 37%, 38%, 39%, 40%, 41%, 42%, 43%, 44%, 45%, or 46% of total protein after 2 weeks at 37° C., as measured using CEX, including any range in between these values. In certain embodiments, the basic peak fraction of a formulation comprising 5 mg/ml, 10 mg/ml, 15 mg/ml, 20 mg/ml, or 25 mg/ml of an anti-PD-L1 antibody and/or variant or mutant (or fragment) thereof described herein is no less than about 32%, 33%, 34%, 35%, 36%, 37%, 38%, 39%, 40%, 41%, 42%, 43%, 44%, 45%, or 46% of total protein after 4 weeks at 37° C., as measured using CEX, including any range in between these values.

The formulations to be used for in vivo administration must be sterile. This is readily accomplished by, e.g., filtration through sterile filtration membranes.

Methods of Diagnosis and Imaging Using Anti-PD-L1 Antibodies and Variants/Mutants Thereof Labeled anti-PD-L1 antibodies, variants, mutants, fragments thereof, and derivatives and analogs thereof, which specifically bind to a PD-L1 polypeptide can be used for diagnostic purposes to detect, diagnose, or monitor diseases and/or disorders associated with the expression, aberrant expression and/or activity of PD-L1. For example, the anti-PD-L1 antibodies and/or variants or mutants (or fragments thereof) provided herein can be used in in situ, in vivo, ex vivo, and in vitro diagnostic assays or imaging assays. Methods for detecting expression of a PD-L1 polypeptide, comprising (a) assaying the expression of the polypeptide in cells (e.g., tissue) or body fluid of an individual using one or more antibodies of this invention and (b)

comparing the level of gene expression with a standard gene expression level, whereby an increase or decrease in the assayed gene expression level compared to the standard expression level is indicative of aberrant expression.

Additional embodiments provided herein include methods of diagnosing a disease or disorder associated with expression or aberrant expression of PD-L1 in an animal (e.g., a mammal such as a human) The methods comprise detecting PD-L1 molecules in the mammal. In certain embodiments, diagnosis comprises: (a) administering an effective amount of a labeled anti-PD-L1 antibody and/or variant or mutant (or fragment) thereof to a mammal (b) waiting for a time interval following the administering for permitting the labeled anti-PD-L1 antibody and/or variant or mutant (or fragment) thereof to preferentially concentrate at sites in the subject where the PD-L1 molecule is expressed (and for unbound labeled molecule to be cleared to background level); (c) determining background level; and (d) detecting the labeled molecule in the subject, such that detection of labeled molecule above the background level indicates that the subject has a particular disease or disorder associated with expression or aberrant expression of PD-L1. Background level can be determined by various methods including, comparing the amount of labeled molecule detected to a standard value previously determined for a particular system.

Anti-PD-L1 antibodies and/or variants or mutants (or fragments) thereof provided herein can be used to assay protein levels in a biological sample using classical immunohistological methods known to those skilled in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur $^{35}$S), tritium ($^{3}$H), indium ($^{115m}$In, $^{113m}$In, $^{112}$In, $^{111}$In), and technetium ($^{99}$Tc, $^{99m}$Tc), thallium $^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; Iuminol; and fluorescent labels, such as fluorescein and rhodamine, and biotin.

Techniques known in the art may be applied to labeled antibodies (or fragments thereof) provided herein. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003).

Alternatively, or additionally, one can measure levels of a PD-L1 polypeptide-encoding nucleic acid or mRNA in the cell, e.g., via fluorescent in situ hybridization using a nucleic acid based probe corresponding to a PD-L1-encoding nucleic acid or the complement thereof; (FISH; see WO98/454 79 published October 1998), Southern blotting, Northern blotting, or polymerase chain reaction (PCR) techniques, such as real time quantitative PCR (RT-PCR). One can also study PD-L1 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., J. Immunol. Methods 132:73-80 (1990)). Aside from the above assays, various in vivo and ex vivo assays are available to the skilled practitioner. For example, one can expose cells within the body of the mammal to an antibody which is optionally labeled with a detectable label, e.g., a radioactive isotope, and binding of the antibody to the cells can be evaluated, e.g., by external scanning for radioactivity or by analyzing a sample (e.g., a biopsy or other biological sample) taken from a mammal previously exposed to the antibody.

Articles of Manufacture and Kits

Another embodiment provided herein is an article of manufacture containing materials useful for the treatment of cancer, such as melanoma, NSCLC, head and neck, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer, and salivary cancer. The article of manufacture can comprise a container and a label or package insert on or associated with the container. Suitable containers include, for example, bottles, vials, syringes, etc. The containers may be formed from a variety of materials such as glass or plastic. Generally, the container holds a composition that is effective for treating the condition and may have a sterile access port (for example the container may be an intravenous solution bag or a vial having a stopper pierceable by a hypodermic injection needle). At least one active agent in the composition is an anti-PD-L1 antibody and/or variant or mutant (or fragment) thereof provided herein. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In one embodiment, the package insert indicates that the composition is used for treating cancer (such as head and neck cancer, lung cancer, or colorectal cancer).

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for isolation or detection of PD-L1 in patients, optionally in combination with the articles of manufacture. For isolation and purification of PD-L1, the kit can contain an anti-PD-L1 antibody and/or variant or mutant (or fragment) thereof provided herein coupled to beads (e.g., SEPHAROSE™ beads). Kits can be provided that contain the antibodies (or fragments thereof) for detection and quantitation of PD-L1 in vitro, e.g., in an ELISA or a Western blot. As with the article of manufacture, the kit comprises a container and a label or package insert on or associated with the container. For example, the container holds a composition comprising at least one anti-PD-L1 antibody and/or variant or mutant (or fragment) thereof provided herein. Additional containers may be included that contain, e.g., diluents and buffers, control antibodies. The label or package insert may

LIST OF EMBODIMENTS

Embodiments provided by the invention include, but are not limited to:

Embodiment 1: An anti-PD-L1 antibody (PL1) comprising a light chain (LC) variable domain sequence comprising (1) a CDR-L1 comprising the amino acid sequence set forth in SEQ ID NO:35; (2) a CDR-L2 comprising the amino acid sequence set forth in SEQ ID NO: 41; and (3) a CDR-L3 comprising the amino acid sequence set forth in SEQ ID NO:44, and a heavy chain (HC) variable domain sequence comprising (1) a CDR-H1 comprising the amino acid sequence set forth in SEQ ID NO:51; (2) a CDR-H2 comprising the amino acid sequence set forth in SEQ ID NO:55; and (3) a CDR-H3 comprising the amino acid sequence set forth in SEQ ID NO:59.

Embodiment 2: An anti-PD-L1 (PL2) comprising a light chain (LC) variable domain sequence comprising (1) a CDR-L1 comprising the amino acid sequence set forth in SEQ ID NO:36; (2) a CDR-L2 comprising the amino acid sequence set forth in SEQ ID NO: 42; and (3) a CDR-L3 comprising the amino acid sequence set forth in SEQ ID NO:45, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:60.

Embodiment 3: An anti-PD-L1 antibody (PL3) comprising a light chain (LC) variable domain sequence comprising (1) a CDR-L1 comprising the amino acid sequence set forth in SEQ ID NO:37; (2) a CDR-L2 comprising the amino acid sequence set forth in SEQ ID NO: 41; and (3) a CDR-L3 comprising the amino acid sequence set forth in SEQ ID NO:46, and a heavy chain (HC) variable domain sequence comprising (1) a CDR-H1 comprising the amino acid sequence set forth in SEQ ID NO:53; (2) a CDR-H2 comprising the amino acid sequence set forth in SEQ ID NO:55; and (3) a CDR-H3 comprising the amino acid sequence set forth in SEQ ID NO:61.

Embodiment 4: An anti-PD-L1 antibody (PL6) comprising a light chain (LC) variable domain sequence comprising (1) a CDR-L1 comprising the amino acid sequence set forth in SEQ ID NO:37; (2) a CDR-L2 comprising the amino acid sequence set forth in SEQ ID NO: 41; and (3) a CDR-L3 comprising the amino acid sequence set forth in SEQ ID NO:47, and a heavy chain (HC) variable domain sequence comprising (1) a CDR-H1 comprising the amino acid sequence set forth in SEQ ID NO:54; (2) a CDR-H2 comprising the amino acid sequence set forth in SEQ ID NO:57; and (3) a CDR-H3 comprising the amino acid sequence set forth in SEQ ID NO:62.

Embodiment 5: An anti-PD-L1 antibody (PL8) comprising a light chain (LC) variable domain sequence comprising (1) a CDR-L1 comprising the amino acid sequence set forth in SEQ ID NO:38; (2) a CDR-L2 comprising the amino acid sequence set forth in SEQ ID NO: 43; and (3) a CDR-L3 comprising the amino acid sequence set forth in SEQ ID NO:48, and a heavy chain (HC) variable domain sequence comprising (1) a CDR-H1 comprising the amino acid sequence set forth in SEQ ID NO:51; (2) a CDR-H2 comprising the amino acid sequence set forth in SEQ ID NO:58; and (3) a CDR-H3 comprising the amino acid sequence set forth in SEQ ID NO:63.

Embodiment 6: An anti-PD-L1 antibody (PL12) comprising a light chain (LC) variable domain sequence comprising (1) a CDR-L1 comprising the amino acid sequence set forth in SEQ ID NO:39; (2) a CDR-L2 comprising the amino acid sequence set forth in SEQ ID NO: 41; and (3) a CDR-L3 comprising the amino acid sequence set forth in SEQ ID NO:49, and a heavy chain (HC) variable domain sequence comprising (1) a CDR-H1 comprising the amino acid sequence set forth in SEQ ID NO:51; (2) a CDR-H2 comprising the amino acid sequence set forth in SEQ ID NO:55; and (3) a CDR-H3 comprising the amino acid sequence set forth in SEQ ID NO:64.

Embodiment 7: An anti-PD-L1 antibody (PL15) comprising a light chain (LC) variable domain sequence comprising (1) a CDR-L1 comprising the amino acid sequence set forth in SEQ ID NO:40; (2) a CDR-L2 comprising the amino acid sequence set forth in SEQ ID NO: 41; and (3) a CDR-L3 comprising the amino acid sequence set forth in SEQ ID NO:50, and a heavy chain (HC) variable domain sequence comprising (1) a CDR-H1 comprising the amino acid sequence set forth in SEQ ID NO:53; (2) a CDR-H2 comprising the amino acid sequence set forth in SEQ ID NO:55; and (3) a CDR-H3 comprising the amino acid sequence set forth in SEQ ID NO:61.

Embodiment 8: An anti-PD-L1 antibody variant (PL2 #3) comprising a light chain (LC) variable domain sequence comprising (1) a CDR-L1 comprising the amino acid sequence set forth in SEQ ID NO:65; (2) a CDR-L2 comprising the amino acid sequence set forth in SEQ ID NO: 42; and (3) a CDR-L3 comprising the amino acid sequence set forth in SEQ ID NO:71, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:77.

Embodiment 9: An anti-PD-L1 antibody variant (PL3 #7) comprising a light chain (LC) variable domain sequence comprising (1) a CDR-L1 comprising the amino acid sequence set forth in SEQ ID NO:37; (2) a CDR-L2 comprising the amino acid sequence set forth in SEQ ID NO: 41; and (3) a CDR-L3 comprising the amino acid sequence set forth in SEQ ID NO:72, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:55; and (3) a CDR-H3 comprising the amino acid sequence set forth in SEQ ID NO:78.

Embodiment 10: An anti-PD-L1 antibody variant (PL3 #7-19) comprising a light chain (LC) variable domain sequence comprising (1) a CDR-L1 comprising the amino acid sequence set forth in SEQ ID NO:66; (2) a CDR-L2 comprising the amino acid sequence set forth in SEQ ID NO:68; and (3) a CDR-L3 comprising the amino acid sequence set forth in SEQ ID NO:73, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:55; and (3) a CDR-H3 comprising the amino acid sequence set forth in SEQ ID NO:79.

Embodiment 11: An anti-PD-L1 antibody variant (PL3 #7-43) comprising a light chain (LC) variable domain sequence comprising (1) a CDR-L1 comprising the amino acid sequence set forth in SEQ ID NO:35; (2) a CDR-L2 comprising the amino acid sequence set forth in SEQ ID NO:69; and (3) a CDR-L3 comprising the amino acid sequence set forth in SEQ ID NO:74, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:55; and (3) a CDR-H3 comprising the amino acid sequence set forth in SEQ ID NO:80.

Embodiment 12: An anti-PD-L1 antibody variant (PL3 #7-54) comprising a light chain (LC) variable domain sequence comprising (1) a CDR-L1 comprising the amino acid sequence set forth in SEQ ID NO:67; (2) a CDR-L2 comprising the amino acid sequence set forth in SEQ ID NO:70; and (3) a CDR-L3 comprising the amino acid sequence set forth in SEQ ID NO:72, and a heavy chain (HC) variable domain sequence comprising (1) a CDR-H1 comprising the amino acid sequence set forth in SEQ ID NO:75; (2) a CDR-H2 comprising the amino acid sequence set forth in SEQ ID NO:76; and (3) a CDR-H3 comprising the amino acid sequence set forth in SEQ ID NO:81.

Embodiment 13: An anti-PD-L1 antibody variant (PL2 #4) comprising a light chain (LC) variable domain sequence comprising (1) a CDR-L1 comprising the amino acid sequence set forth in SEQ ID NO:94; (2) a CDR-L2 comprising the amino acid sequence set forth in SEQ ID NO:42; and (3) a CDR-L3 comprising the amino acid sequence set forth in SEQ ID NO:95, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:96.

Embodiment 14: An anti-PD-L1 antibody variant (PL2 #5) comprising a light chain (LC) variable domain sequence comprising (1) a CDR-L1 comprising the amino acid sequence set forth in SEQ ID NO:97; (2) a CDR-L2 comprising the amino acid sequence set forth in SEQ ID NO:42; and (3) a CDR-L3 comprising the amino acid sequence set forth in SEQ ID NO:98, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:99.

Embodiment 15: An anti-PD-L1 antibody variant (PL2 #39) comprising a light chain (LC) variable domain sequence comprising (1) a CDR-L1 comprising the amino acid sequence set forth in SEQ ID NO:100; (2) a CDR-L2 comprising the amino acid sequence set forth in SEQ ID NO:42; and (3) a CDR-L3 comprising the amino acid sequence set forth in SEQ ID NO:95, and a heavy chain (HC) variable domain sequence comprising (1) a CDR-H1 comprising the amino acid sequence set forth in SEQ ID NO:52; (2) a CDR-H2 comprising the amino acid sequence set forth in SEQ ID NO:56; and (3) a CDR-H3 comprising the amino acid sequence set forth in SEQ ID NO:101.

Embodiment 16: An anti-PD-L1 antibody variant (PL3 #1) comprising a light chain (LC) variable domain sequence comprising (1) a CDR-L1 comprising the amino acid sequence set forth in SEQ ID NO:37; (2) a CDR-L2 comprising the amino acid sequence set forth in SEQ ID NO:106; and (3) a CDR-L3 comprising the amino acid sequence set forth in SEQ ID NO:107, and a heavy chain (HC) variable domain sequence comprising (1) a CDR-H1 comprising the amino acid sequence set forth in SEQ ID NO:108; (2) a CDR-H2 comprising the amino acid sequence set forth in SEQ ID NO:55; and (3) a CDR-H3 comprising the amino acid sequence set forth in SEQ ID NO:109.

Embodiment 17: The anti-PD-L1 antibody variant of embodiment 10, where said anti-PD-L1 antibody variant comprises a CDR-L2 comprising one or more mutations at the N-glycosylation site.

Embodiment 18: The anti-PD-L1 antibody variant of embodiment 11, where said anti-PD-L1 antibody variant comprises a CDR-L2 comprising one or more mutations at the N-glycosylation site.

Embodiment 19: The antigen binding fragment of the anti-PD-L1 antibody or variant thereof according to any one of embodiments 1-18, wherein the antigen binding fragment is selected from the group consisting of a Fab, Fab', a F(ab')2, a single-chain Fv (scFv), an Fv fragment, a diabody, and a linear antibody.

Embodiment 20: The anti-PD-L1 antibody or variant or an antigen binding fragment thereof according to any one of embodiments 1-19, wherein the antibody is a multispecific antibody.

Embodiment 21: The anti-PD-L1 antibody, variant, or antigen binding fragment thereof according to any one of embodiments 1-20 conjugated to a therapeutic agent.

Embodiment 22: The anti-PD-L1 antibody, variant, or antigen binding fragment thereof according to any one of embodiments 1-20 conjugated to a label.

Embodiment 23: The anti-PD-L1 antibody, variant, or an antigen binding fragment thereof according to embodiment 22, wherein the label is selected from the group consisting of a radioisotope, a fluorescent dye, and an enzyme.

Embodiment 24: An isolated nucleic acid molecule that encodes the anti-PD-L1 antibody, variant, or antigen binding fragment thereof according to any one of embodiments 1-19.

Embodiment 25: An expression vector encoding the nucleic acid molecule of embodiment 24.

Embodiment 26: A cell comprising the expression vector of embodiment 25.

Embodiment 27: A method of producing an anti-PD-L1 antibody, variant, or an antigen binding fragment thereof comprising culturing the cell of embodiment 26 and recovering the antibody from the cell culture.

Embodiment 28: A composition comprising the anti-PD-L1 antibody, variant, or an antigen binding fragment thereof according to any one of embodiments 1-23 and a pharmaceutically acceptable carrier.

Embodiment 29: A method of detecting a PD-L1 protein in sample from a patient by contacting the anti-PD-L1 antibody, variant, or antigen binding fragment thereof according to any one of embodiments 1-20 to the sample, and detecting the anti-PD-L1 antibody bound to the PD-L1 protein.

Embodiment 30: The method according to embodiment 29, wherein the anti-PD-L1 antibody, variant, or antigen binding fragment thereof is used an immunohistochemistry assay (IHC) or in an ELISA assay.

Embodiment 31: A method of treating cancer in a subject, comprising administering an effective amount of the composition of embodiment 28 to the subject.

Embodiment 32: The method of embodiment 31, wherein the cancer is selected from the group consisting of melanoma, NSCLC, head and neck, urothelial cancer, triple-negative breast cancer (TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer, esophageal cancer, nasopharyngeal carcinoma (NPC), biliary tract cancer, colorectal cancer, breast cancer, cervical cancer, thyroid cancer, and salivary cancer.

Embodiment 33: The method of embodiment 32, wherein the subject is further administered a therapeutic agent selected from the group consisting of an anti-neoplastic agent, a chemotherapeutic agent, a growth inhibitory agent and a cytotoxic agent.

Embodiment 34: The method of embodiment 32, wherein the subject is further administered radiation therapy.

EXAMPLES

Example 1

Development of Human Anti-PD-L1 Antibodies and Variants

For the development of anti-PD-L1 antibodies, the entire strategy is summarized as follows: Seven positive leads (i.e., PL1, PL2, PL3, PL6, PL8, PL12, and PL15) were identified by screening of a human phage display library with human PD-L1_ECD-His. In general, after three rounds of panning with biotinylated human PD-L1_ECD-His coupled to streptavidin-coated magnetic Dynabeads® M-280 (Thermo Fisher Scientific #11205D), Fabs of leads were screened and measured their binding to hPD-L1_ECD-Fc and hPD-L1_ECD-His via ELISA, and the Fab sequences of seven selected leads were then cloned into N297A mutant of human IgG1 Fc backbone to become full-length antibodies that were used to conduct more experiments on determination of kinetic characteristics, whole cell PD-L1 binding activity, PD-1 blocking activities, in vitro and in vivo functions. Based on all the data, PL2 and PL3 were found to have superior anti-tumor activities over other selected leads, so their affinity was further optimized by generating phage display libraries of PL2 and PL3 and at least three rounds of panning were performed for in vitro affinity maturation. Variants derived from PL2 and PL3 with enhanced affinity (i.e., PL2 #3 and PL3 #7) were then identified and activities and functions were verified following a very similar process as the one used for the selection of the antibody leads. Also of note is that, at this stage, variants of different IgG isotypes (i.e., IgG1, mtIgG1 (N297A), IgG2, IgG4) were generated and the affinity and in vitro and in vivo efficacy for a panel of PL2 #3 and PL3 #7 that were conjugated with various Fc backbones were compared at the same time. In addition to tumor/antigen-specific T cell xenograft models, a hPD-1 knock-in model was exploited to verify the efficacy of PL2 #3 and PL3 #7, and the data demonstrated that they were both comparable to the anti-PD-L1 reference antibody. To further improve affinity of PL3 #7, another phage display library based on PL3 #7 was generated for affinity maturation as before. By doing this, three new variants (i.e., PL3 #7-19, -43, -54) were identified and used to compare their efficacy with PL2 top variant, PL2 #3. Details of the comparison data are described herewith in the following Examples.

Here, the binding affinity and kinetics (ka, kd, and $K_D$) of seven selected leads were measured using surface plasmon resonance (SPR) and shown in Table 4. Anti-human IgG Fc was first immobilized onto a sensor chip and then capture anti-PD-L1 reference antibody and the anti-PD-L1 antibody leads: PL1, PL2, PL3, PL6, PL8, PL12, and PL15 with Rmax~250 RU. Experiments were carried out at 25° C., and measurements were made with serial dilutions of hPD-L1_ECD-His from 55.4 nM to 11.1 nM passing over the captured antibodies in HBS-P+ buffer supplemented with 0.1% (w/v) BSA with a flow rate of 25 μL/min. All data were analyzed with the evaluation software and curves were fit with a 1:1 Langmuir binding model. Data are representative of two independent experiments performed in duplicate.

TABLE 4

|  | Ref-1 | PL1 | PL2 | PL3 | PL6 | PL8 | PL12 | PL15 |
|---|---|---|---|---|---|---|---|---|
| Ka (1/Ms) | 1.45E+05 | 2.91E+05 | 4.38E+05 | 3.48E+05 | 1.05E+06 | 3.82E+05 | 4.16E+05 | 6.45E+05 |
| Kd (1/s) | 1.29E−03 | 4.53E−03 | 3.90E−03 | 4.10E−03 | 1.22E−02 | 3.48E−03 | 2.67E−03 | 9.33E−03 |
| $K_D$ (M) | 9.79E−09 | 1.58E−08 | 8.72E−09 | 1.19E−08 | 1.12E−08 | 8.85E−09 | 6.68E−09 | 1.50E−08 |

Amino acid sequence alignments of light chain (LC) and heavy chain (HC) of the selected anti-PD-L1 antibody leads: PL1, PL2, PL3, PL6, PL8, PL12, PL15 are shown in FIGS. 1A-1B. The complementary determining regions (CDRs) in these LCs and HCs of these leads were marked in bold and underlined text.

Example 2

Binding Affinity and Kinetics of Anti-PD-L1 Variants of Antibody PL2

Antibody lead PL2 was used in in vitro phage display-based affinity maturation experiments to generate additional clones with improved binding performance First, CDR-L1/CDR-L3/CDR-H3 (focusing on 3 CDRs) nucleic acid libraries were generated via PCR, cloned into a phage display vector, and transformed into E. coli TG1 or SS320 cells to produce a library of phages. After three rounds of panning with biotinylated hPD-L1-His coupled to streptavidin-coated magnetic Dynabeads® M-280 (Thermo Fisher Scientific #11205D), forty (40) Fab clones were screened via ELISA, and four Fabs (i.e., #3, #4, #5, and #39) were found to have better binding performance than parental PL2. Further kinetic characteristics were measured by surface plasmon resonance (SPR) using full-length IgGs of PL2 #3, PL2 #4, PL2 #5, and PL2 #39 and found to have binding performance that was equivalent to or better than the anti-PD-L1 reference antibodies.

Table 5 below shows the amino acid sequences of PL2 variants with mutations on L1 (SEQ ID NOS 36, 65, 94, 36, and 100, respectively, in order of appearance), L3 (SEQ ID NOS 45, 71, 95, 98, and 95, respectively, in order of appearance), and H3 regions (SEQ ID NOS 60, 77, 96, 99, and 101, respectively, in order of appearance).

TABLE 5

| CDR | L1 | | | | | | | | | | | | | L3 | | | | | | | | | |
|---|---|---|---|---|---|---|---|---|---|---|---|---|---|---|---|---|---|---|---|---|---|---|---|
| PL2 | S | G | S | S | S | Y | I | E | S | S | Y | V | S | E | I | W | D | S | G | L | G | G | V |
| PL2#3 | | | | | | | | | | | | | G | | | | R | | | | | | |
| PL2#4 | | | | | V | | | | | | | | | K | | | | | | | | | |
| PL2#5 | | | | | | | | | | | | | | | | | | | | R | | | |
| PL2#39 | | | | | | | | | T | | | | | K | | | | | | | | | |

| CDR | H3 | | | | | | | | | | | | | |
|---|---|---|---|---|---|---|---|---|---|---|---|---|---|---|
| PL2 | N | E | L | R | W | Y | P | Q | A | G | A | F | D | I |
| PL2#3 | | | | | | | | | | | | | | R |
| PL2#4 | | | | | | | L | | | | | | | |
| PL2#5 | | | | | | | F | | | | | | | |
| PL2#39 | | | | | | | K | | | | | | | |

The binding affinity and kinetics were measured using surface plasmon resonance (SPR). Anti-human IgG Fc was first immobilized on a sensor chip and then capture the anti-PD-L1 reference antibodies and PL2 variants with Rmax~250 RU. Experiments were carried out at 25° C., and measurements were made with serial dilutions of hPD-L1-His from 19.1 nM to 0.71 nM passing over the captured antibodies in HBS-P+ buffer supplemented with 0.1% (w/v) BSA with a flow rate of 25 μL/min. All data were analyzed with the evaluation software and curves were fit with a 1:1 Langmuir binding model. All the data are representative of two independent studies performed in duplicate.

Table 6 shows association and dissociation kinetics, along with calculated affinity ($K_D$) of PL2 variants compared to the anti-PD-L1 reference antibodies measured by surface plasmon resonance (SPR). All the variants, parental PL2, and reference antibodies were cloned into human IgG2 backbone in this study. Improvement of affinity for PL2 variants in contrast to the reference anti-PD-L1 antibody was shown in Table 6, as well. The data presented in Table 6 indicate that, among PL2 variants, PL2 #3 had the best binding affinity to human PD-L1-His. Table 7 shows the result that focusing on the comparison of kinetics among difference human IgG isotypes of PL2 #3 in a subsequent study. Here, different isotypes of PL2 #3 showed similar binding affinity to human PD-L1-His.

TABLE 6

| Average (N = 2) | ka [1/(M · s)] | kd [1/s] | $K_D$ [M] | Improvement over ref-1 |
|---|---|---|---|---|
| anti-PD-L1 ref-1 (IgG2) | 2.47E+05 | 2.48E−03 | 8.41E−09 | 1.00 |
| anti-PD-L1 ref-2 (IgG2) | 1.24E+06 | 9.88E−04 | 9.07E−10 | |
| PL2 IgG2 | 7.47E+05 | 2.17E−03 | 6.96E−09 | 1.21 |
| PL2 #3 IgG2 | 1.32E+06 | 5.57E−04 | 5.16E−10 | 16.30 |
| PL2 #4 IgG2 | 8.82E+05 | 9.90E−04 | 1.27E−09 | 6.62 |
| PL2 #5 IgG2 | 8.12E+05 | 2.21E−03 | 3.07E−09 | 2.74 |
| PL2 #39 IgG2 | 2.04E+06 | 1.43E−03 | 7.79E−10 | 10.80 |

TABLE 7

| Average (N = 2) | ka [1/(M · s)] | kd [1/s] | $K_D$ [M] | Improvement over ref-1 |
|---|---|---|---|---|
| anti-PD-L1 ref-1 (mtIgG1) | 7.90E+05 | 5.05E−04 | 6.32E−10 | 1.00 |
| anti-PD-L1 ref-2 (IgG2) | 1.18E+06 | 2.68E−04 | 2.37E−10 | |
| PL2 IgG1 | 1.25E+06 | 1.93E−03 | 1.56E−09 | 0.41 |
| PL2 #3 IgG1 | 1.14E+06 | 2.76E−04 | 2.50E−10 | 2.53 |
| PL2 #3 mtIgG1 (N297A) | 1.33E+06 | 2.86E−04 | 2.21E−10 | 2.86 |
| PL2 #3 IgG2 | 1.34E+06 | 1.62E−04 | 1.18E−10 | 5.36 |
| PL2 #3 IgG4 | 1.26E+06 | 2.93E−04 | 2.39E−10 | 2.64 |

Example 3

Binding Affinity and Kinetics of Anti-PD-L1 Variants of Antibody PL3

Antibody lead PL3 was used in in vitro phage display-based affinity maturation experiments to generate additional clones with improved binding performance First, CDR-L1/CDR-L2/CDR-L3/CDR-H1/CDR-H2/CDR-H3 (focusing on 6 CDRs) nucleic acid libraries were generated via PCR, cloned into a phage display vector, and transformed into E. coli TG1 or SS320 cells to produce a library of phages. After three rounds of panning with biotinylated hPD-L1-His coupled to streptavidin-coated magnetic Dynabeads® M-280 (Thermo Fisher Scientific #11205D), twenty (20) Fab clones were screened via ELISA, and two Fabs (i.e., #1 and #7) were found to have better binding performance than parental PL3. Further kinetic characteristics were measured by surface plasmon resonance (SPR) using full-length IgGs of PL3 #1 and PL3 #7 and found to have binding performance that was equivalent to or better than the reference anti-PD-L1 antibodies.

Table 8 below shows the amino acid sequences of PL3 variants with mutations on L2, L3 and H1, H3 regions. Table 9 shows association and dissociation kinetics, along with calculated affinity ($K_D$) of PL3 variants compared to the reference anti-PD-L1 antibodies measured by surface plasmon resonance (SPR). This result also exhibited the comparison of kinetics among difference human IgG isotypes of PL3 #1 and PL3 #7. Improvement of affinity for PL3 variants in contrast to the reference anti-PD-L1 antibody was shown in Table 9, as well. All the data are representative of two independent experiments performed in duplicate.

These data show that, among PL3 variants, PL3 #7 had slightly better binding affinity to human PD-L1-His. Different isotypes of PL3 #7 showed similar binding affinity to human PD-L1-His. The L1 sequences are disclosed as SEQ ID NOS 120, 120, and 120, respectively, in order of appearance. The L2 sequences are disclosed as SEQ ID NOS 121, 122, and 121, respectively, in order of appearance. The L3 sequences are disclosed as SEQ ID NOS 123, 124, and 125, respectively, in order of appearance. The H1 sequences are disclosed as SEQ ID NOS 53, 108, and 75, respectively, in order of appearance. The H2 sequences are disclosed as SEQ ID NOS 126, 126, and 126, respectively, in order of appearance. The H3 sequences are disclosed as SEQ ID NOS 61, 109, and 78, respectively, in order of appearance.

Clone PL3 #7, which had much better affinity than parental PL3, was further used in in vitro phage display-based affinity maturation experiments to generate additional clones with improved binding performance First, CDR-L1/CDR-L2/CDR-L3/CDR-H2/CDR-H3 (fixing CDR-H1 and focusing on 5 CDRs) nucleic acid libraries were generated via PCR, cloned into a phage display vector, and transformed into E. coli TG1 or SS320 cells to produce a library of phages. After three rounds of panning with biotinylated hPD-L1-His coupled to streptavidin-coated magnetic Dynabeads® M-280 (Thermo Fisher Scientific #11205D), fifty-seven (57) Fab clones were screened via ELISA, and three Fabs (i.e., 19, 43 and 54) were found to have better binding performance than parental PL3 #7. Further kinetic characteristics were measured by bio-layer interferometry approach (ForteBio Octet RED96) using full-length IgGs of PL3 #7-19, PL3 #7-43 and PL3 #7-54 and found to have binding performance that was equivalent to or better than the reference anti-PD-L1 antibodies.

Table 10 below shows the amino acid sequences of PL3 #7 variants with mutations on L1 (SEQ ID NOS 120, 127, 128, and 129, respectively, in order of appearance), L2 (SEQ ID NOS 121, 130, 131, and 132, respectively, in order of appearance), L3 (SEQ ID NOS 125, 133, 134, and 125, respectively, in order of appearance) and H2 (SEQ ID NOS 126, 126, 126, and 135, respectively, in order of appearance), H3 regions (SEQ ID NOS 78, 79, 80, and 80, respectively, in order of appearance). The H1 sequences are disclosed as SEQ ID NOS 75, 75, 75, and 75, respectively, in order of appearance.

TABLE 8

| CDR | L1 | | | | | | L2 | | | | | | L3 | | | | | | |
|---|---|---|---|---|---|---|---|---|---|---|---|---|---|---|---|---|---|---|---|
| PL3 | I | G | A | G | Y | D | G | N | S | N | R | P | S | Y | D | S | S | L | S | A | P | V | V |
| PL3#1 | | | | | | | | | | R | | | T | | | | | | | R | | | |
| PL3#7 | | | | | | | | | | | | | T | | | | | | | | R | | |

| CDR | H1 | | | H2 | | | | | | | H3 | | | | | | | | |
|---|---|---|---|---|---|---|---|---|---|---|---|---|---|---|---|---|---|---|---|
| PL3 | S | Y | T | I | S | I | P | I | L | G | I | A | N | S | R | D | G | Y | S | F | G | A | F | D | I |
| PL3#1 | | | R | | | | | | | | | | | | | | | | | V | | | | | S |
| PL3#7 | | | P | | | | | | | | | | A | | | | | | | | | | | | |

TABLE 9

| Average (N = 2) | ka [1/(M · s)] | kd [1/s] | $K_D$ [M] | Improvement over ref-1 |
|---|---|---|---|---|
| anti-PD-L1 ref-1 (mtIgG1) | 7.90E+05 | 5.05E−04 | 6.32E−10 | 1.00 |
| anti-PD-L1 ref-2 (IgG2) | 1.18E+06 | 2.68E−04 | 2.37E−10 | |
| PL3 IgG1 | 5.42E+05 | 2.91E−03 | 5.46E−09 | 0.12 |
| PL3 IgG2 | 4.17E+05 | 2.77E−03 | 6.64E−09 | 0.10 |
| PL3 #1 mtIgG1 (N297A) | 1.10E+06 | 3.95E−04 | 3.66E−10 | 1.73 |

TABLE 9-continued

| Average (N = 2) | ka [1/(M · s)] | kd [1/s] | $K_D$ [M] | Improvement over ref-1 |
|---|---|---|---|---|
| PL3 #1 IgG2 | 9.31E+05 | 6.70E−04 | 7.40E−10 | 0.85 |
| PL3 #7 IgG1 | 9.97E+05 | 4.44E−04 | 4.57E−10 | 1.38 |
| PL3 #7 IgG2 | 9.95E+05 | 3.27E−04 | 3.49E−10 | 1.81 |
| PL3 #7 IgG4 | 1.14E+06 | 3.62E−04 | 3.21E−10 | 1.97 |

TABLE 10

| CDR | L1 | | | | | | | | L2 | | | | | | | | L3 | | | | | | | |
|---|---|---|---|---|---|---|---|---|---|---|---|---|---|---|---|---|---|---|---|---|---|---|---|---|
| PL3#7 | I | G | A | G | Y | D | G | N | S | N | R | P | T | Y | D | S | S | L | S | A | R | V | V | |
| PL3#7-19 | | | G | | | | | | | | | | T | | | | | | | | | T | | |
| PL3#7-43 | V | | | | | | | | | | | S | | | | | | | G | | | | | |
| PL3#7-54 | | | Q | | | | | | | A | | | | | | | | | | | | | | |

| CDR | H1 | | | | | H2 | | | | | | | | H3 | | | | | | | | | | |
|---|---|---|---|---|---|---|---|---|---|---|---|---|---|---|---|---|---|---|---|---|---|---|---|---|
| PL3#7 | S | Y | P | I | S | I | P | I | L | G | I | A | N | S | R | D | G | Y | A | F | G | A | F | D | I |
| PL3#7-19 | | | | | | | | | | | | | | | | | | | | | | | | | V |
| PL3#7-43 | | | | | | | | | | | | | | | | P | | | | | | | | | |
| PL3#7-54 | | | | | | | | | | | | | D | | | P | | | | | | | | | |

Affinity and kinetics of PL3 #7 variants were measured by bio-layer interferometry approach using an Octet RED96 (ForteBio) system with streptavidin (SA) sensors at 25° C. and agitation speed of 1000 rpm. Briefly, black 96-well plate was prepared with columns containing 200 μL/well of reagents required for determination of affinity. In general, Octet SA sensors were first placed in wells containing 1×Kinetics Buffer (PBS, 0.1% BSA, 0.02% Tween-20, pH 7.4) for 180 seconds to establish a baseline. Sensors were then transferred to wells containing 10 μg/mL biotinylated PL3 #7 variants (1:1 ratio of antibody:biotin with EZ-Link® NHS-PEG4-Biotin, Thermo Fisher Scientific #21329) for 300 seconds to load the SA coated tips. Sensors were then regenerated by 3×5 second incubations in Regeneration Buffer (10 mM Glycine, pH 1.5) followed by a 5 second incubation in 1×Kinetics Buffer each time. Regeneration was repeated before measurement of each association/dissociation cycle. Sensors were then placed in fresh 1×Kinetics Buffer for 180 seconds to establish a baseline. Association was then measured by incubating the sensors for 5 minutes in wells containing hPD-L1-His followed by transferring to wells containing 1×Kinetics Buffer for 10 minutes to measure dissociation. Kinetics (ka, kd, and $K_D$) were measured by global fitting four association/dissociation cycles of data obtained from 1:3 serial dilutions of hPD-L1-His from 38.28 nM to 1.42 nM (one association/dissociation cycle for one concentration) with a 1:1 Langmuir binding model. All data were analyzed with Octet Data Analysis Software v.9.0 and representative of two independent experiments performed in duplicate.

Table 11 shows association and dissociation kinetics, along with calculated affinity ($K_D$) of PL3 #7 variants compared to the reference anti-PD-L1 antibodies measured by the ForteBio Octet RED96 machine (Menlo Park, Calif., USA) using a bio-layer interferometry approach. Improvement of affinity of PL3 #7 variants in contrast to the reference anti-PD-L1 antibody was shown in Table 11, as well. All the data are representative of two independent experiments performed in duplicate. The data shown in Table 11 indicate that PL3 #7-19, PL3 #7-43, and PL3 #7-54 had better binding affinity than parental PL3 #7.

TABLE 11

| Average (N = 2) | ka [1/(M · s)] | kd [1/s] | $K_D$ [M] | Improvement over ref-1 |
|---|---|---|---|---|
| anti-PD-L1 ref-1 (mtIgG1) | 2.07E+05 | 5.37E−04 | 2.46E−09 | 1.00 |
| anti-PD-L1 ref-2 (IgG2) | 2.91E+05 | 1.54E−04 | 5.20E−10 | |
| PL2 #3 mtIgG1 | 2.21E+05 | 5.61E−04 | 2.46E−09 | 1.00 |
| PL3 #7 mtIgG1 | 2.98E+05 | 3.05E−04 | 1.09E−09 | 2.26 |
| PL3 #7-19 mtIgG1 | 4.19E+05 | 2.01E−04 | 5.38E−10 | 4.57 |
| PL3 #7-43 mtIgG1 | 3.30E+05 | 1.03E−04 | 3.13E−10 | 7.86 |
| PL3 #7-54 mtIgG1 | 3.07E+05 | 2.28E−04 | 7.72E−10 | 3.19 |

Therefore, PL2 top variant (PL2 #3), PL3 top variant (PL3 #7), and PL3 #7 top variants (PL3 #7-19, -43, -54) with superior higher affinity and superior functional activities were generated from in vitro phage display-based affinity maturation experiments. In general, three rounds of panning were performed using biotinylated hPD-L1-His coupled to streptavidin-coated magnetic Dynabeads® M-280. Fabs of top variants were then screened via ELISA and cloned into N297A mutant of human IgG1 Fc backbone to become full-length antibodies Amino acid sequence alignments of light chains (LCs) and heavy chains (HCs) of these anti-PD-L1 top variants are shown in FIGS. 11A-11B. The complementary determining regions (CDRs) in the LCs and HCs of these anti-PD-L1 top variants were marked in bold and underlined text.

Example 4

Binding Anti-PD-L1 Antibodies to Recombinant Human PD-L1/Fc Fusion Proteins and Activated CD3$^+$ T Cells ELISA assays were performed to assess the binding of selected antibodies to recombinant human PD-L1/Fc fusion proteins. Fifteen nanograms per well of human PD-L1/Fc proteins were coated on 96-well EIA microplate overnight at 4° C. After blocking with 5% skim milk, serially diluted antibodies were added and incubated at RT for 1 hour. The unbound antibodies were removed and wells were washed with PBST twice. The HRP-conjugated secondary antibody was added to the wells, and, following an incubation, excess secondary antibody was washed away. TMB was added to the wells, and following incubation, the reaction was stopped, and HRP activity was measured by monitoring the increase in absorbance at 450 nm.

Human T cells were isolated from PBMC using MagniSort™ Human T Cell Enrichment Kit (eBioscience). Isolated T cells were activated by 5 μg/mL phytohemagglutinin (PHA) for 3 days to stimulate the PD-L1 expression. Activated T cells were collected and incubated in FACS buffer (PBS with 2% FBS) with human Fc blocker (eBioscience) for 20 minutes at 4° C. Binding of anti-PD-L1 monoclonal antibody was assessed by incubating the activated T cells with the serial-diluted antibodies in FACS buffer. The cells were washed with flow buffer and the binding was detected with a FITC-labeled rabbit anti-human IgG Fcγ Ab. Cells were also stained with mouse anti-human CD3 PE-Cy7 (eBioscience) for gating CD3-positive T cells. Flow cytometric analyses were performed using the Cytomics FC 500 (Beckman Coulter Inc.).

Figure 2B:
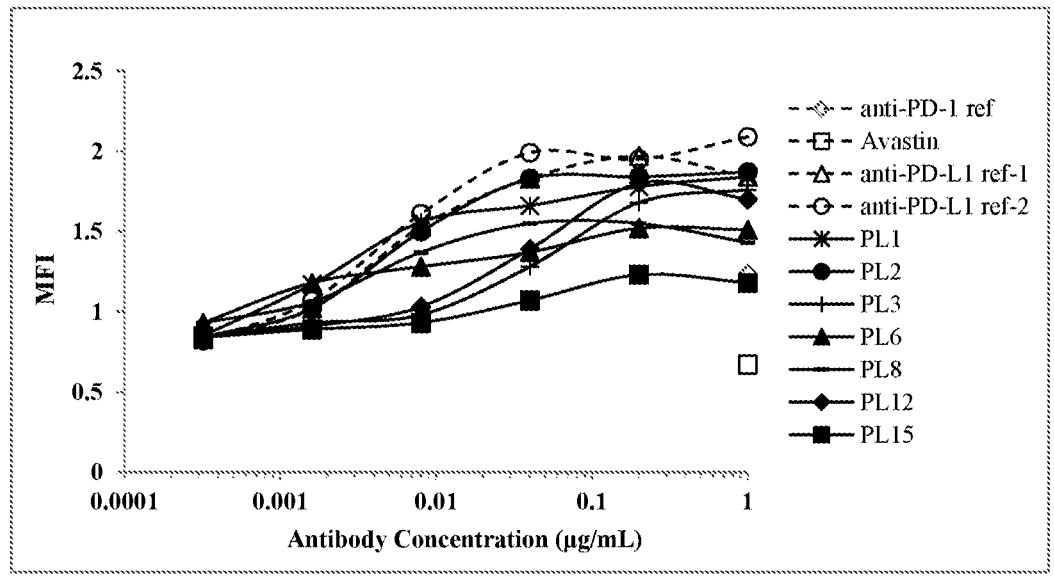

Therefore, selected anti-PD-L1 antibodies were tested for their bindings to recombinant human PD-L1 proteins by ELISA and activated CD3$^+$ T cells by flow cytometry. Anti-PD-L1 reference and anti-PD-1 reference antibodies were used as the positive and negative control, respectively. FIGS. 2A and 2B show that all selected anti-PD-L1 antibodies are able to bind both human PD-L1 recombinant proteins and PD-L1 expressing T cells.

Example 5

Blocking of PD-1 Binding to PD-L1 by Anti-PD-L1 Antibodies

PD-L1 expressing CHO-S cells were suspended in FACS buffer (PBS with 4% FBS). Various concentrations of tested antibodies were added to the cell suspension (3.5E5 cells/well) and incubated at 4° C. for 30 minutes. Unbound antibodies were washed off and biotin-labeled PD-1-Fc fusion protein was added and incubated at 4° C. for 30 minutes. The cells were washed and then stained with streptavidin-PE at 4° C. for 30 minutes. Flow cytometric analyses were performed using the Cytomics FC 500 (Beckman Coulter Inc.).

Figure 3:
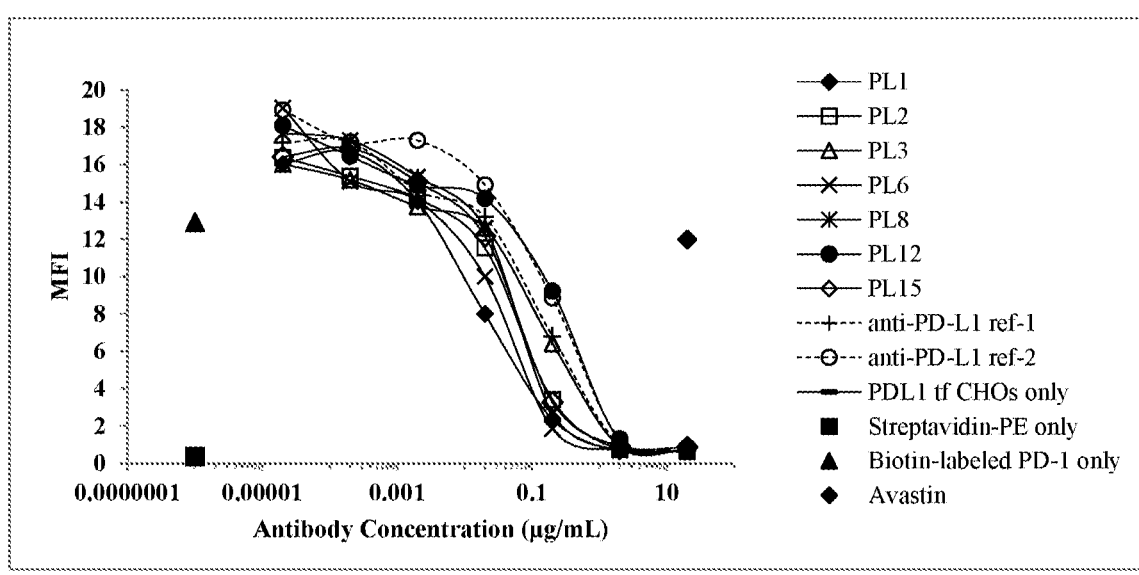
FIG. 3. Blocking of PD-1 binding to PD-L1 by selected antibodies. Anti-PD-L1 antibodies were tested for the ability to block the binding of PD-1 to PD-L1 expressing CHO-S cells using a flow cytometry assay. Anti-PD-L1 reference antibody and Avastin were used as the positive and negative control, respectively. The anti-PD-L1 monoclonal antibodies blocked binding of PD-1 to PD-L1-transfected CHO-S cells, as measured by the mean fluorescent intensity (MFI) of staining.

Selected anti-PD-L1 antibodies were tested for the ability to block the binding of PD-1 to PD-L1 expressing CHO-S cells using a flow cytometry assay. Anti-PD-L1 reference antibody and Avastin were used as the positive and negative control, respectively. The data shown in FIG. 3 indicate that all the selected anti-PD-L1 monoclonal antibodies blocked binding of PD-1 to PD-L1-transfected CHO-S cells, as measured by the mean fluorescent intensity (MFI) of staining.

Example 6

Effect of Anti-PD-L1 Antibodies on Cytokine Production and T Cell Proliferation in a Mixed Leukocyte Reaction (MLR)

A mixed leukocyte reaction was employed to demonstrate the effect of blocking the PD-L1/PD-1 pathway to lymphocyte effector cells. T cells in the assay were tested for proliferation and IFN-gamma or IL-2 secretion in the presence or absence of anti-PD-L1 antibodies.

Human T-cells were purified from PBMC using the Lympho-kwik T (One Lamda, Inc.). Isolated T cells were suspended in PBS and labeled with 1 μM of CFSE at room temperature for 10 minutes. After washing cells with the complete media (RPMI-1640 with 10% FBS), CFSE-labeled T cells were suspended in the complete media at the concentration of 1E6 cells/mL.

Allogeneic dendritic cells were generated from PBMC. The isolated PBMCs were incubated with 200 U/mL of recombinant human IL-3 (eBioscience) overnight to allow monocyte/macrophage population to attach to the plates. The non-adherent cells were removed and the plates were washed twice with the complete media. The cells on the plates were then cultured in the complete media containing 200 U/mL of human IL-4 (eBioscience) and 200 U/mL of human GM-CSF (eBioscience) for 6 days. Monocyte-derived dendritic cells were matured by adding TNF-alpha (100 U/mL) to the culture at day 6 and incubating overnight. The matured DC were trypsinized, harvested, and suspended in the complete media at the concentration of 1E5 cells/mL.

Each reaction contained 10E5 CFSE-labeled T-cells and 10E4 allogeneic dendritic cells in a total volume of 200 μl. Antibodies were added to each culture at different concentrations. Either no antibody or an anti-VEGF antibody (Avastin) was used as a negative control. Anti-PD-1 ref or anti-PD-L1 ref antibody was used as the positive control. The cells were cultured for 5 days at 37° C. On day 5, 100 μl of medium was taken from each culture for cytokine measurement. The levels of cytokines were measured using Human IFN-γ or IL-2 ELISA MAX™ Deluxe kits (BioLegend). The cells were collected and analyzed for T cell proliferation by flow cytometry.

Figure 4A:
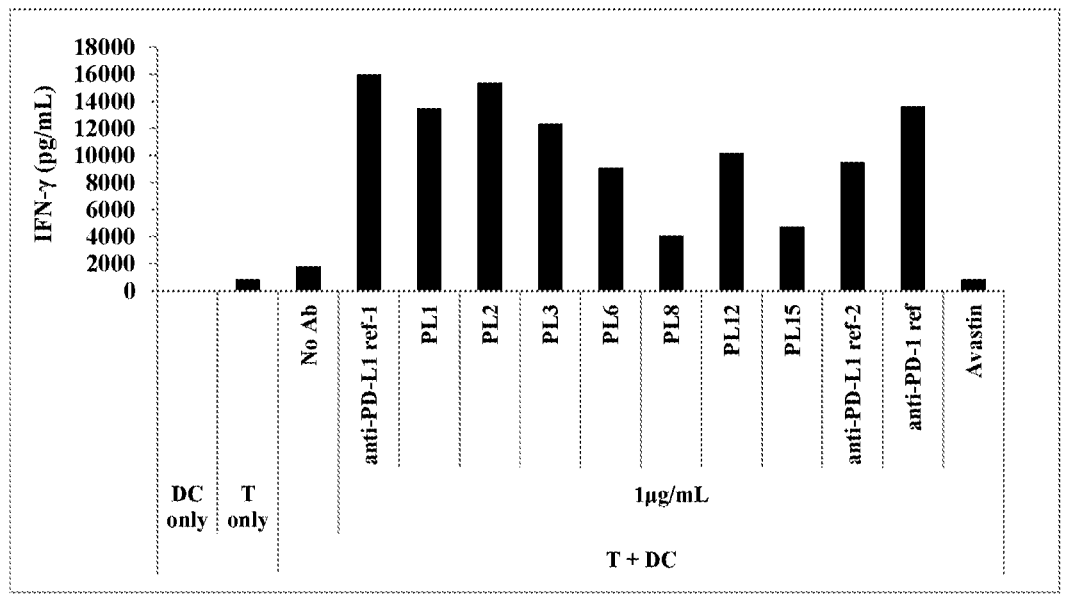
FIGS. 4A-4B. Effect of anti-PD-L1 leads on cytokine production and T cell proliferation in a mixed leukocyte reaction (MLR). The monoclonal antibodies against human PD-L1 enhance IFN-γ secretion and T cell proliferation in a mixed leukocyte reaction assay. Anti-PD-L1 reference antibody and anti-PD-1 reference antibody were used as the positive control. Avastin (anti-VEGF) was used as the negative control.
Figure 4B:
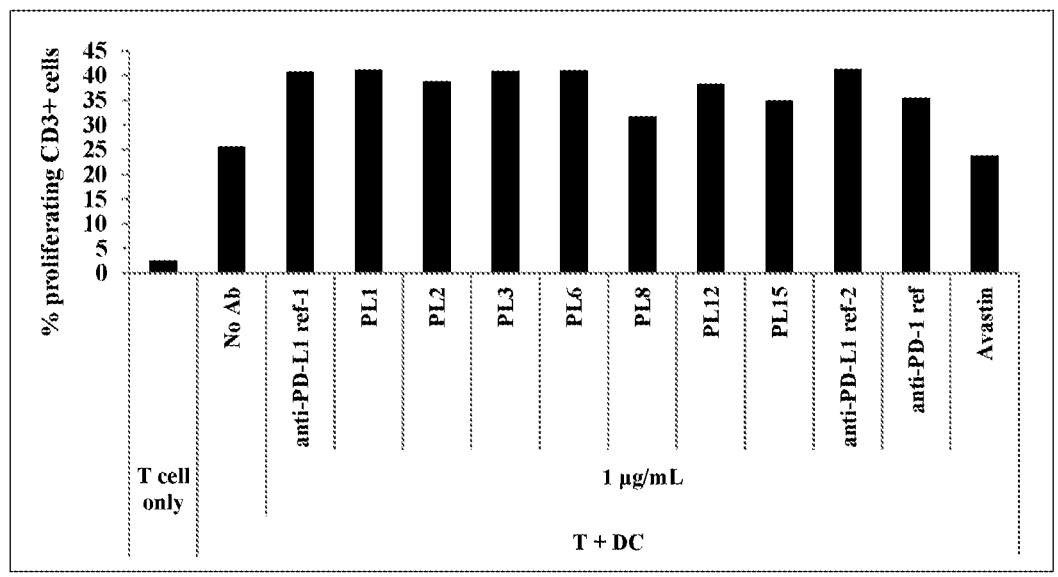

The data shown in FIGS. 4A-4B indicate that all selected anti-PD-L1 antibodies enhance IFN-γ secretion and promote T cell proliferation in a mixed leukocyte reaction assay. Anti-PD-L1 and anti-PD-1 reference antibodies were used as the positive controls. Avastin (anti-VEGF) was used as the negative control. FIG. 4A is a bar graph showing the IFN-γ secretion, and FIG. 4B is a bar graph showing the CD3$^+$ T cell proliferation at indicated concentration of antibodies.

Figure 6A:
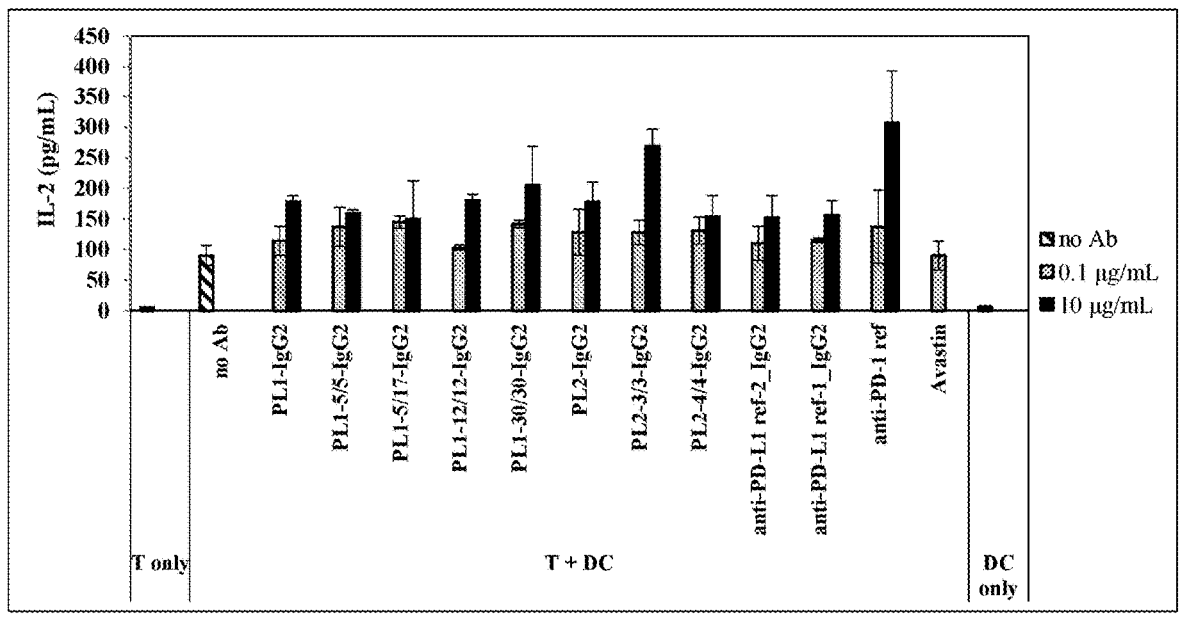
FIGS. 6A-6B. Effect of PL2 and PL3 variants on cytokine production in a mixed leukocyte reaction (MLR). The PL2 and PL3 variants enhance IL-2 secretion in a mixed leukocyte reaction assay. Anti-PD-L1 reference antibody and Avastin were used as the positive and negative control antibody, respectively.
Figure 6B:
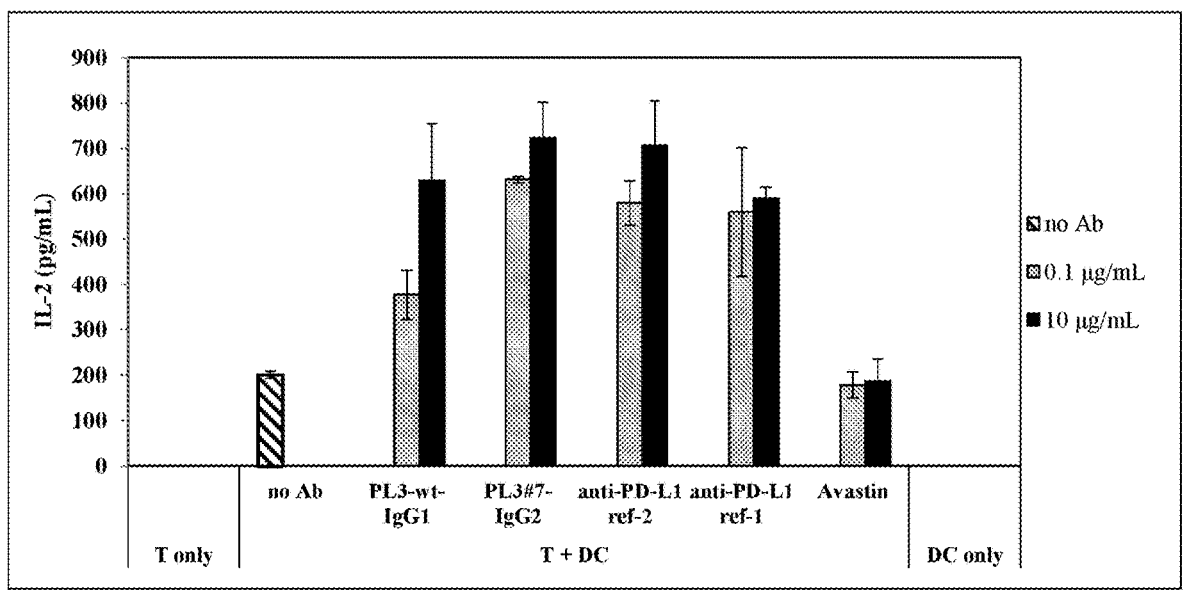

Furthermore, the IL-2 secretions in MLR induced by the anti-PD-L1 antibody PL2 parental and variants are shown in FIG. 6A, and the IL-2 secretions in MLR induced at indicated concentration of the anti-PD-L1 antibody PL3 parental antibody and variants are shown in FIG. 6B. These data indicate that the selected PL2 variant PL2-3/3 (PL2 #3) and PL3 variant (PL3 #7) showed superior efficacy than parental antibodies in stimulating T cell activation.

Figure 8A:
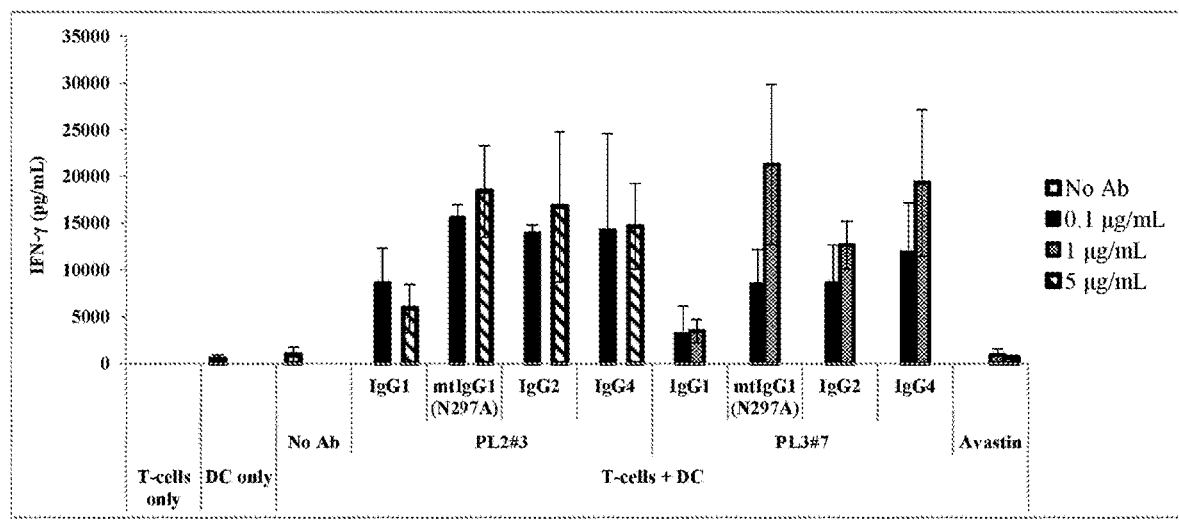
FIGS. 8A-8D. The efficacy of different IgG forms of PL2 #3 and PL3 #7 in a mixed leukocyte reaction (MLR). Different IgG forms of PL2 #3 and PL3 #7 were tested using MLR assay. Avastin was used as the negative control antibody. The bar graphs showing the secreted IFN-γ and IL-2 induced by tested antibodies were presented in FIGS. 8A and 8B, respectively.
Figure 8B:
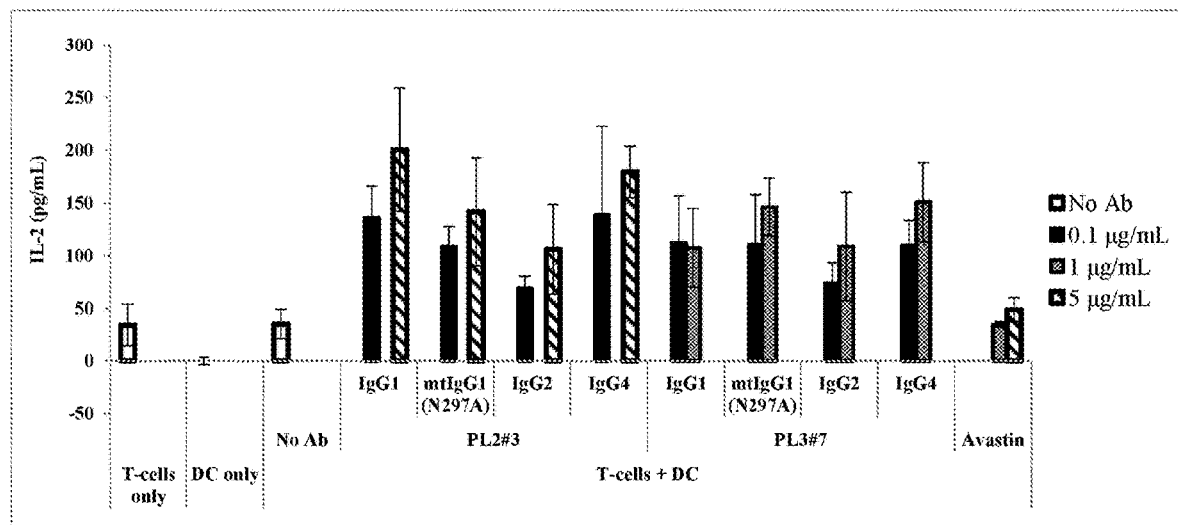
Figure 8C:
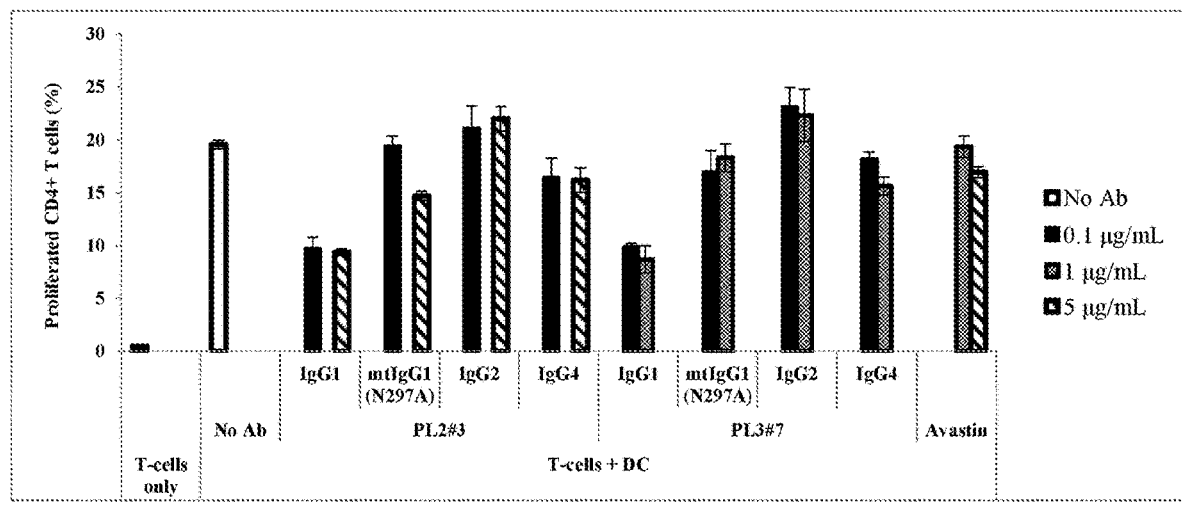
Figure 8D:
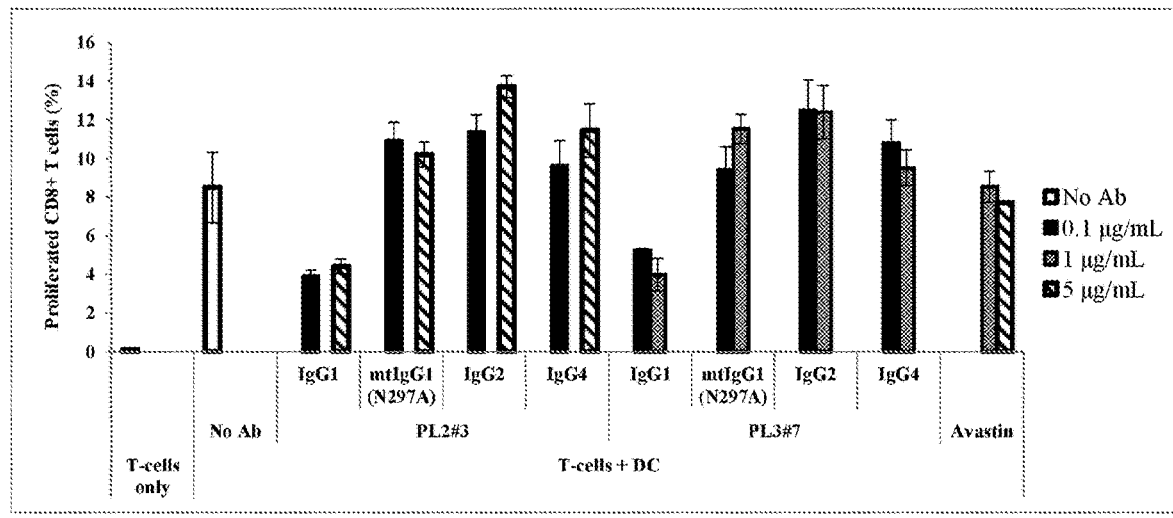
Figure 12A:
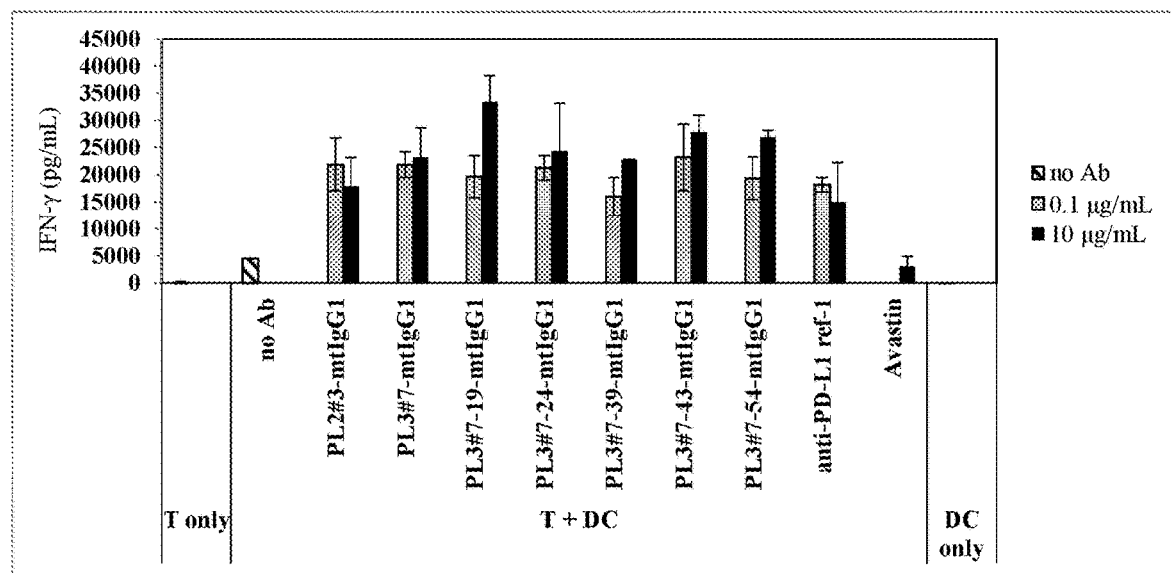
FIGS. 12A-12B. Effect of PL3 #7 variants on cytokine production and T cell proliferation in a mixed leukocyte reaction (MLR). The modified PL3 #7 variants enhance IFN-γ secretion and $CD8^+$ T cell proliferation in a mixed leukocyte reaction assay. Anti-PD-L1 reference antibody and Avastin were used as the positive and negative control, respectively.
Figure 12B:
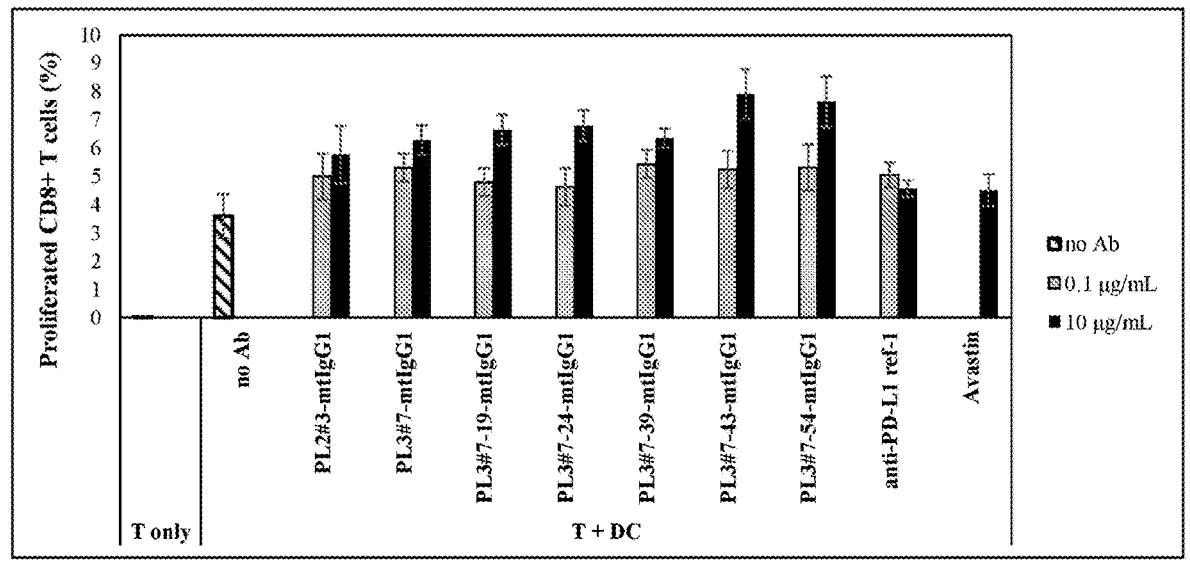

Moreover, the efficacies of different IgG forms of the anti-PD-L1 antibodies PL2 #3, PL3 #7, and PL3 #7 variants in a mixed leukocyte reaction (MLR) are shown in FIGS. 8A-8D and FIGS. 12A-12B. The bar graphs showing the secreted IFN-γ and IL-2 induced by these anti-PD-L1 antibodies were presented in FIGS. 8A, 8B, and 12A. FIG. 8C is a bar graph showing the CD4$^+$ T cell proliferation at various concentrations of the anti-PD-L1 antibodies L2 #3, PL3 #7, and FIGS. 8D and 12B are bar graphs showing the CD8$^+$ T cell proliferation at indicated concentrations of these three anti-PD-L1 antibodies. FIGS. 12A and 12B particularly indicate that the anti-PD-L1 antibodies PL3 #7 variants, e.g., PL3 #7-19, -43, and -54, showed superior activities in the enhancement of IFN-γ secretion and CD8$^+$ T cell proliferation.

Example 7

Tumor Growth Inhibition Activity of PL2 and PL3 Anti-PD-L1 Antibodies in A375/Antigen-Specific T-Cell Xenograft Model The in-vivo activity of anti-human PD-L1 antibodies was investigated in xenograft mouse models using immunocompromised NOD/SCID (non-obese diabetic/severe combined immunodeficiency) mice. The mice were engrafted subcutaneously with human cancer cell lines expressing human PD-L1 and human PBMC or antigen-specific T cells. Intraperitoneal doses of antibodies were given to mice inoculated with the human melanoma cell line A375 or human NSCLC cell line NCI-H292. Effect of the antibodies was observed on tumor growth until a 2000 mm³ tumor volume or gross tumor necrosis.

To generate antigen-specific T cells, T cells were separated from healthy donor's PBMCs using MagniSort® Human T Cell Enrichment Kit (eBioscience). Isolated T cells were co-cultured with mitomycin-C treated A375 cells and rhIL-2 (50 IU/mL) for 10 to 14 days to enrich antigen-specific T cells. Human PBMCs were isolated from healthy donor's whole blood using Histopaque-1077 (Sigma-Aldrich).

A375 and antigen-specific T cells were mixed immediately before subcutaneous administration at the indicated effector-to-target (E:T) ratios. NCI-H292 cells were mixed with fresh human PBMCs at the indicated E:T ratio and subcutaneously inoculated into mice. The first dose of test article was administered intraperitoneally 2 hours after engraftment of cancer/effector cells. Mice were treated with antibodies twice a week for 3-5 weeks. The formation of tumor was observed in each animal two times a week. Tumors were measured by caliper; tumor volumes (V) were calculated using the following formula:

$$V(mm^3)=0.5(length(mm) \times width(mm) \times width(mm)/2).$$

Figure 5A:
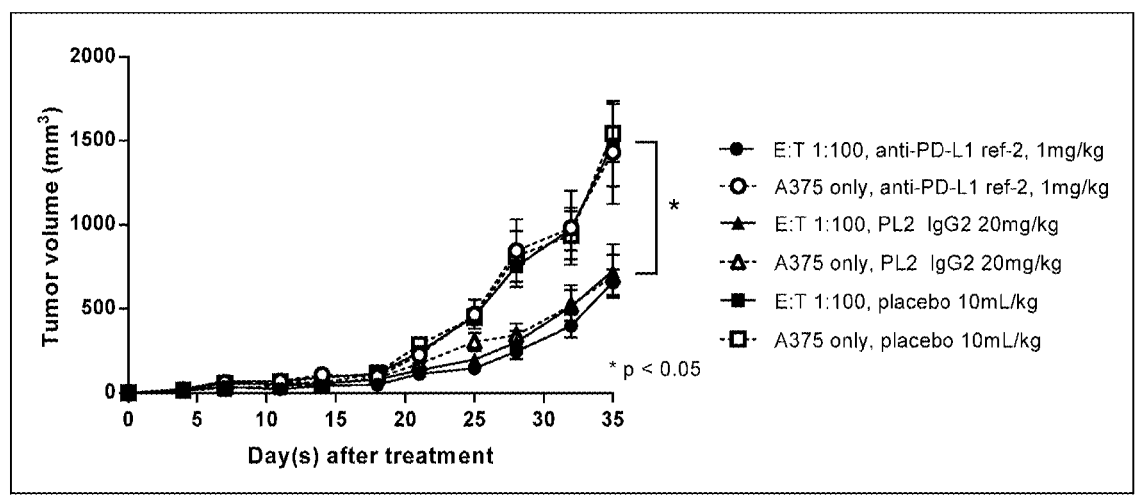
FIGS. 5A-5B. Tumor growth inhibition activity of PL2 and PL3 antibody in A375/antigen-specific T cell xenograft model. The mice (n=4/group) were engrafted subcutaneously with the mixture of human melanoma cell lines A375 and antigen-specific T cells (T cells:cancer cells=1:100). Tested antibodies were intraperitoneally injected into mice twice a week from day 0. Tumor growth curves of PL2- and PL3-treated mice were shown in FIGS. 5A and 5B, respectively. All data points are the means±SEM.
Figure 5B:
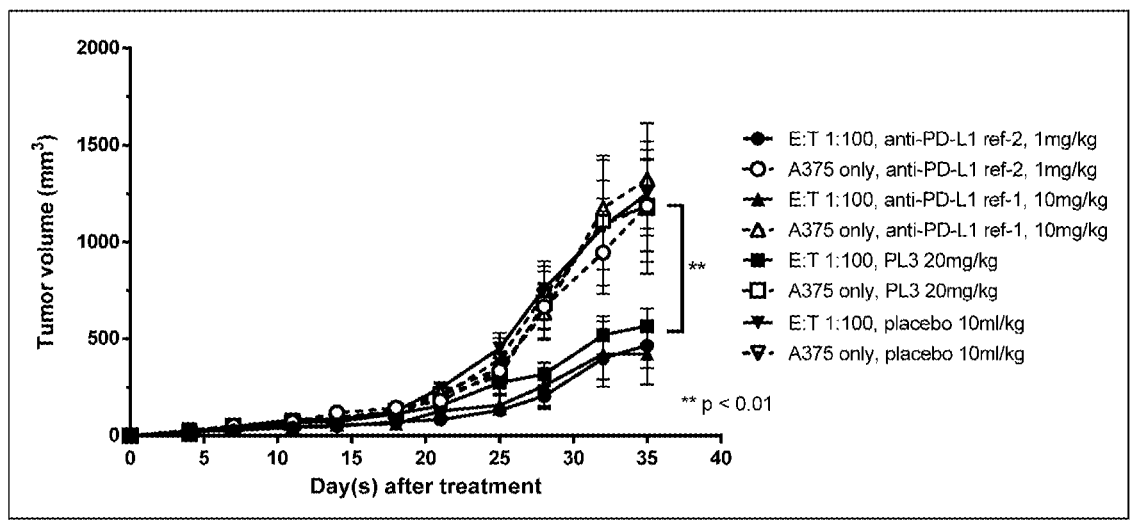

The mice (n=4/group) were engrafted subcutaneously with the mixture of human melanoma cell lines A375 and antigen-specific T cells (T cells:cancer cells=1:100). Tested antibodies were intraperitoneally injected into mice twice a week from day 0. The in vivo efficacy of all anti-PD-L1 leads were tested in the A375/antigen-specific T cells xenograft model. Tumor growth curves of PL2- and PL3-treated mice were shown in FIGS. 5A and 5B. The data show that PL2 and PL3 could significantly inhibit A375 tumor growth in vivo.

Figure 7A:
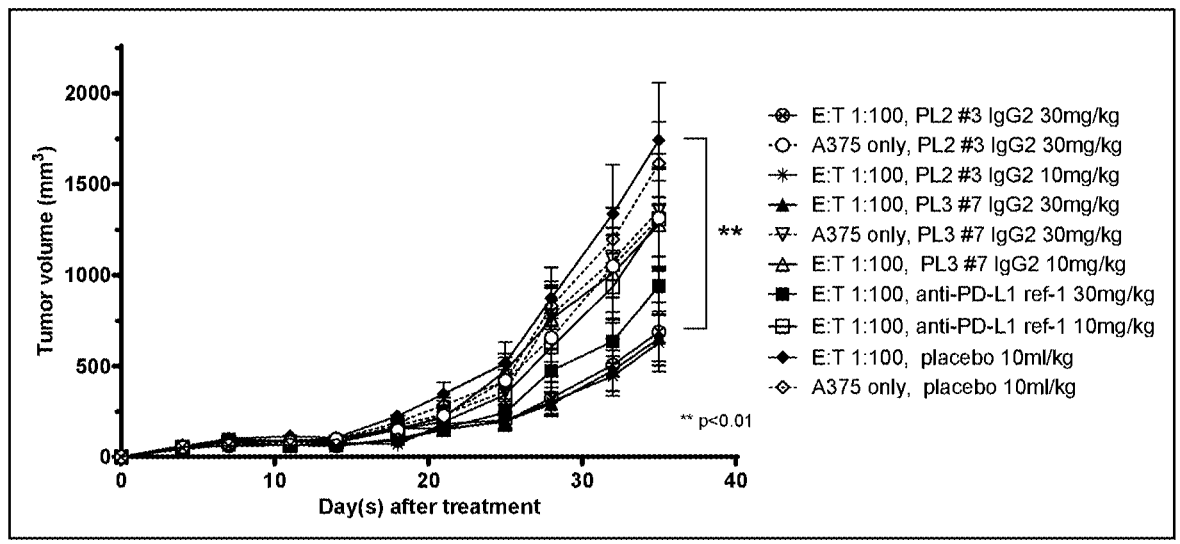
FIGS. 7A-7B. Tumor growth inhibition activity of PL2 and PL3 top variants in A375/antigen-specific T cell xenograft model. The mice (n=4/group) were engrafted subcutaneously with the mixture of human melanoma cell lines A375 and antigen-specific T cells (T cells:cancer cells=1:100). Tested antibodies were intraperitoneally injected into mice twice a week from day 0. Tumor growth curves of PL2 #3- and PL3 #7-treated mice were shown in FIG. 7A. The individual tumor volume at day 35 was presented in FIG. 7B. All data points are the means±SEM.
Figure 7B:
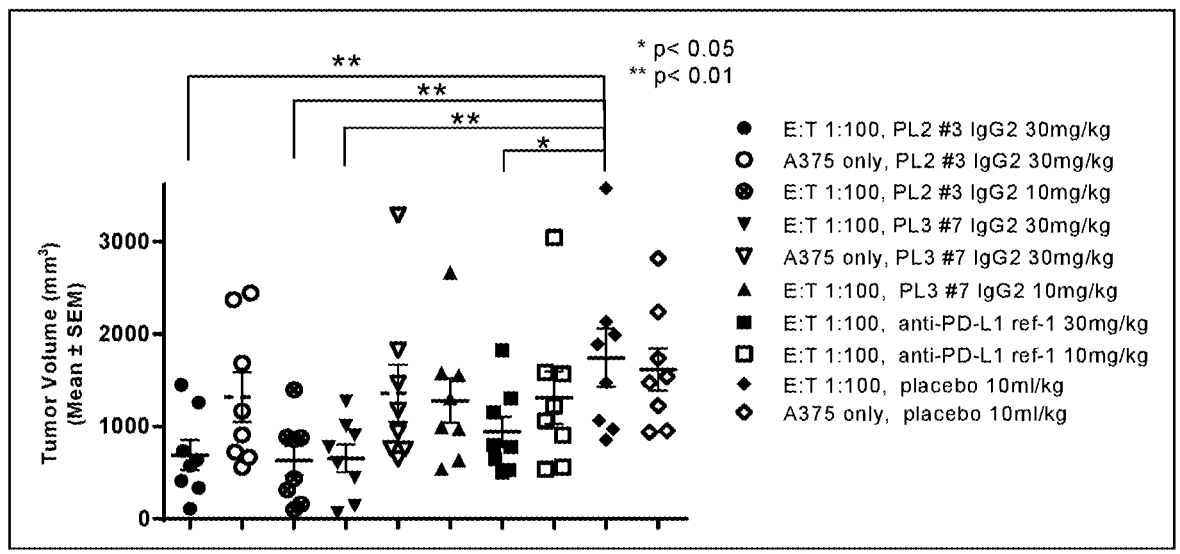

Furthermore, tumor growth inhibition activities of the anti-PD-L1 antibodies PL2 and PL3 top variants in A375/antigen-specific T cell xenograft model are shown in FIGS. 7A and 7B. The data indicate that PL2 #3 IgG2 inhibited A375 tumor growth at the dose of 30 mg/kg and 10 mg/kg. PL3 #7 IgG2 inhibited A375 growth only at the dose of 30 mg/kg.

Figure 9A:
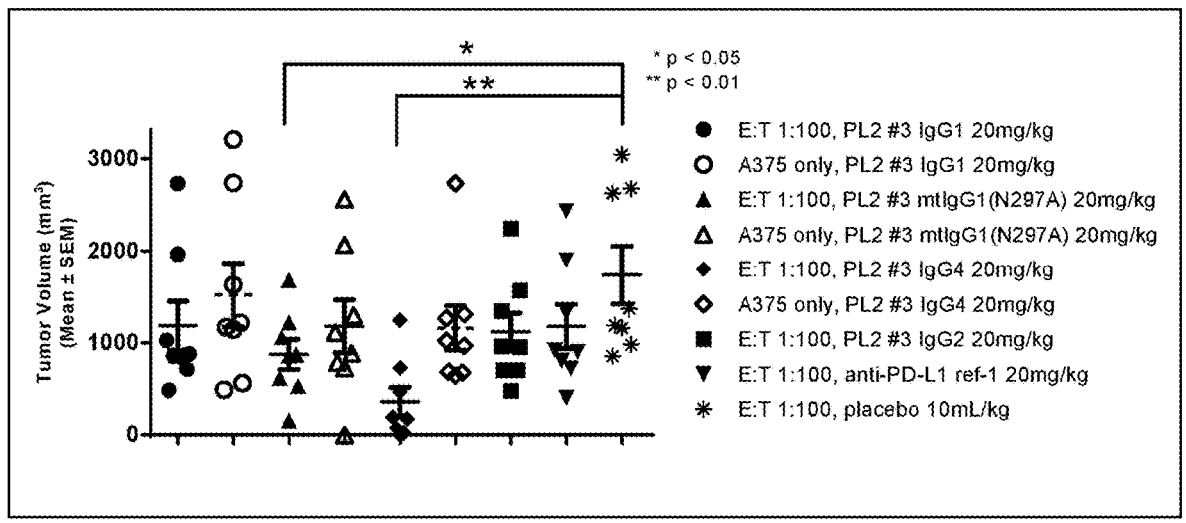
FIGS. 9A-9B. Tumor growth inhibition activity of various PL2 #3 and PL3 #7 IgG isotypes in A375/antigen-specific T cell xenograft model.
Figure 9B:
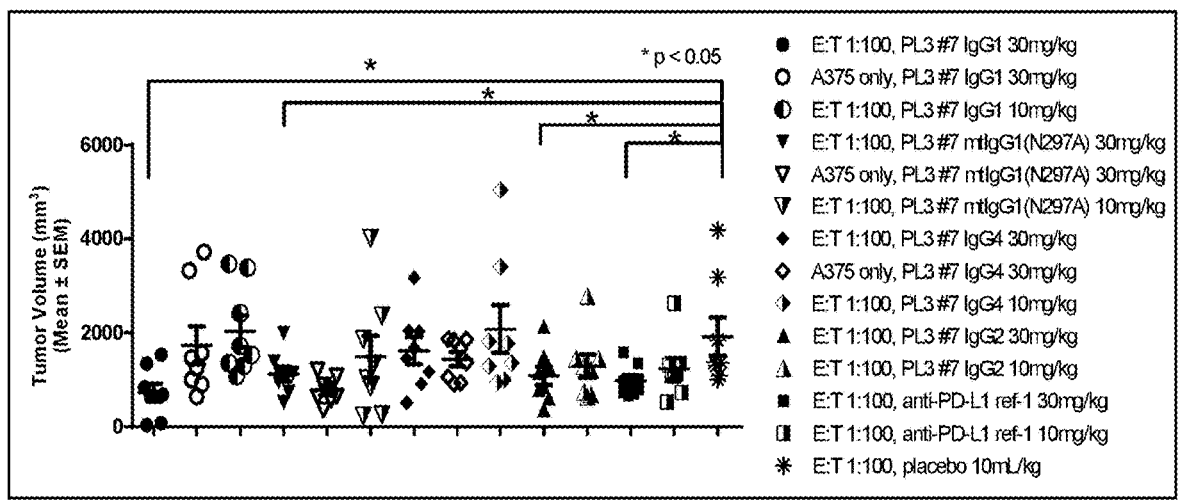

Moreover, the tumor growth inhibition activities of various PL2 #3 and PL3 #7 IgG isotypes in A375/antigen-specific T cell xenograft model are shown in FIGS. 9A (PL2 #3) and 9B (PL3 #7). The data indicate that mutated IgG1 and IgG4 form of the anti-PD-L1 antibody PL2 #3 showed better anti-tumor effect at the dose of 20 mg/kg. Wild-type IgG1, mutated IgG1, and IgG2 of the anti-PD-L1 antibody PL3 #7 inhibited A375 tumor growth at the dose of 30 mg/kg. Based on these data, mutant IgG (N297A) was chosen as the Fc backbone.

Figure 15A:
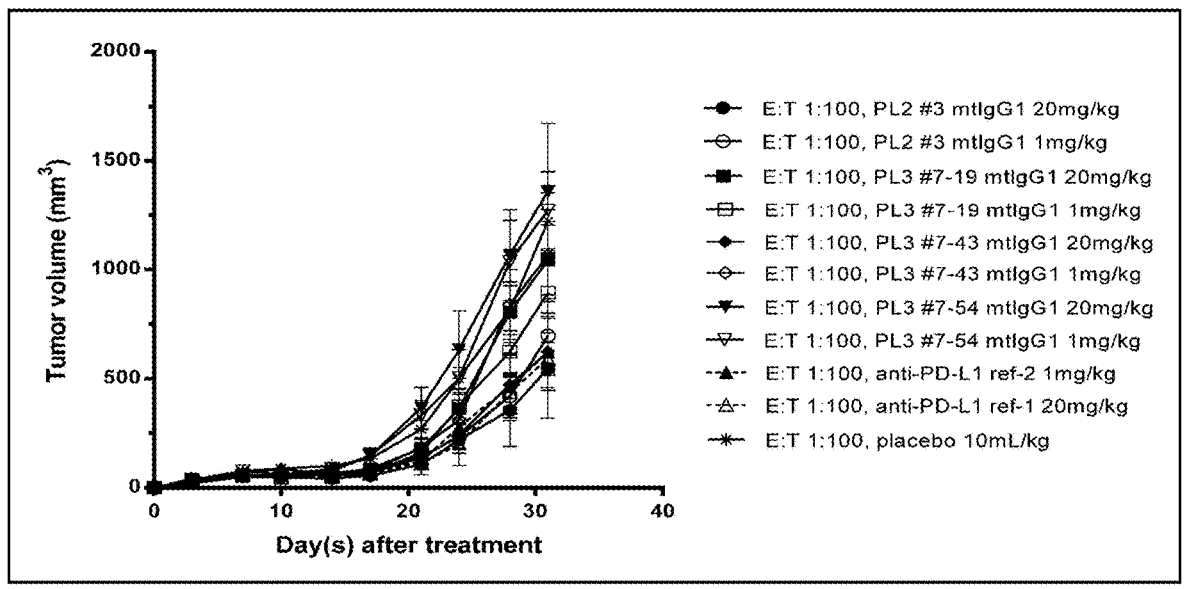
FIGS. 15A-15B. Tumor growth inhibition activity of PL2 #3 and PL3 #7 variants in A375/antigen-specific T cell xenograft model. The mice (n=4/group) were engrafted subcutaneously with the mixture of human melanoma cell lines A375 and antigen-specific T cells (T cells (E):cancer cells (T)=1:100). Tested antibodies were intraperitoneally injected into mice twice a week from day 0. Tumor growth curves of mAb-treated mice were shown in FIG. 15A. The individual tumor volumes at day 31 were presented in FIG. 15B. All data points are the means±SEM.
Figure 15B:
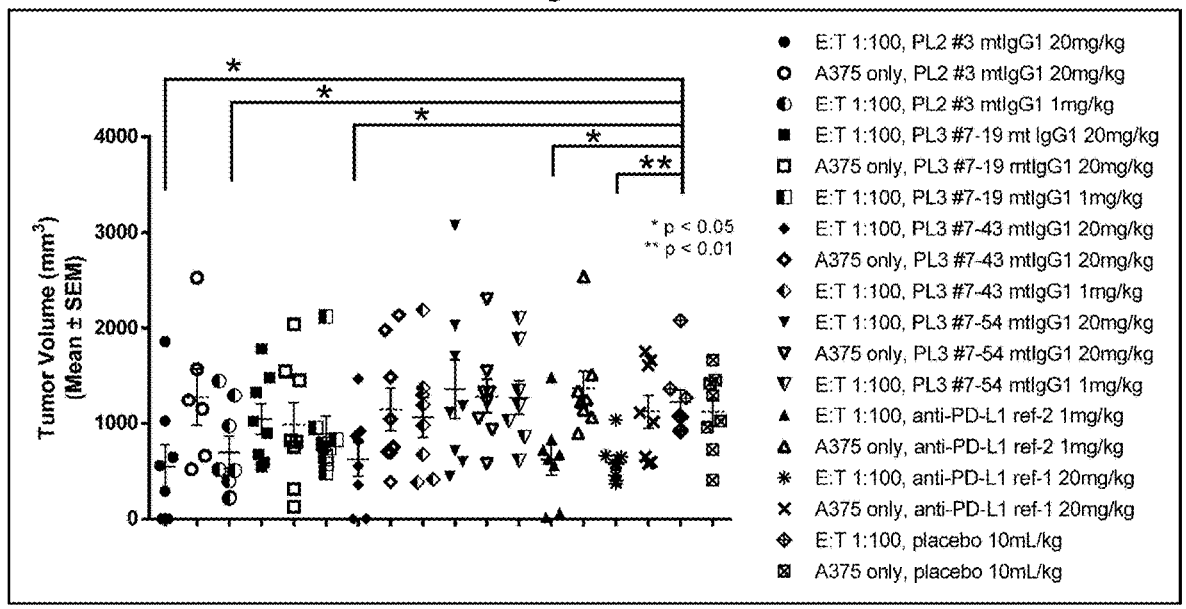

The tumor growth inhibition activities of the mutants of the anti-PD-L1 antibody PL2 #3 and PL3 #7 in A375/antigen-specific T cell xenograft model are shown in FIGS. 15A-15B. The mice (n=4/group) were engrafted subcutaneously with the mixture of human melanoma cell lines A375 and antigen-specific T cells (T cells (E):cancer cells (T)=1:100). Tested antibody mutants of PL2 #3 and PL3 #7 were intraperitoneally injected into mice twice a week from day 0. Tumor growth curves of mAb-treated mice were shown in FIG. 15A. The individual tumor volumes at day 31 were presented in FIG. 15B. The data indicate that PL2 #3 mtIgG1 showed antitumor activities at 20 mg/kg and 1 mg/kg in A375 (melanoma)/antigen specific-T cell model; and PL3 #7-43 showed superior antitumor activities at the dose of 20 mg/kg.

Example 8

Tumor Growth Inhibition Activity of Mutant Anti-PD-L1 Antibodies in hPD1 KI Mice The in-vivo activity of anti-human PD-1 antibodies was investigated in human PD-1 knock-in C57BL/6 mice (hPD1 KI mice). The mice were subcutaneously inoculated with human PD-L1 transfected mouse MC38 cancer cells (5E5 cells per mouse). Antibody treatments were started when tumor volumes reached approximately 86 mm³. Six animals were assigned to each experimental group before the treatment. The animals received doses of anti-PD-L1 antibodies twice a week for 3 weeks. The formation of tumor was observed in each animal two times a week. Tumors were measured by caliper and tumor volumes (V) were calculated using the following formula:

$$V(mm^3)=0.5 \times (length(mm) \times width(mm) \times width(mm)/2).$$

Figure 10:
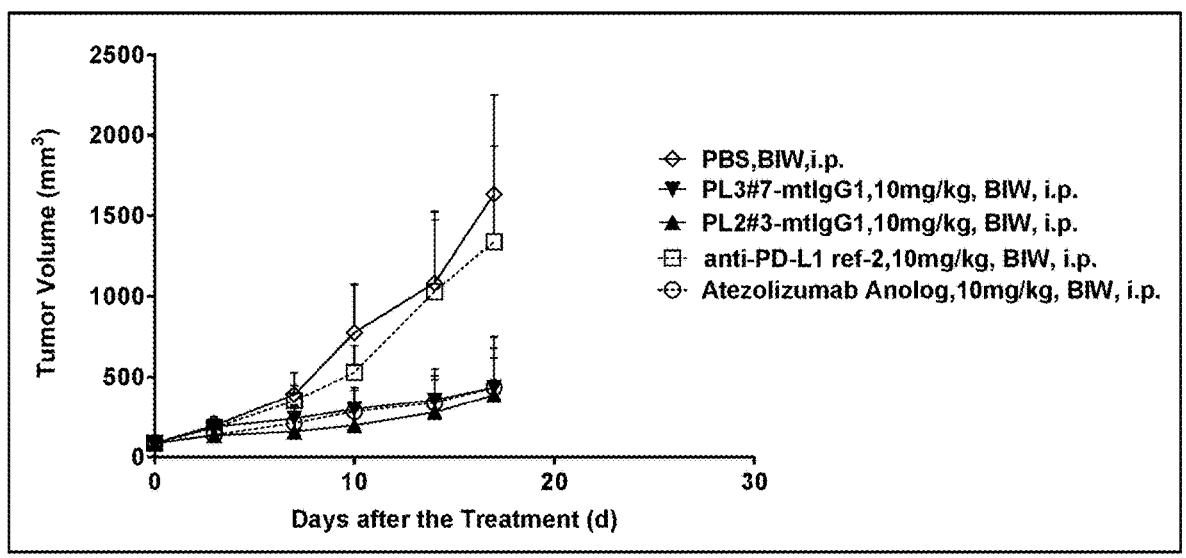
FIG. 10. Tumor growth Inhibition Activity of PL2 #3-mtIgG1 and PL3 #7-mtIgG1 antibodies in hPD1 KI mice. The human PD-1 knock-in (hPD1 KI) mice (n=6/group) were engrafted subcutaneously with MC38-huPD-L1 (MC38 transfected with human PD-L1) cells. Antibody treatments were started when tumor volumes reached approximately 86 $mm^3$. Tested antibodies were intraperitoneally injected into mice twice a week for 3 weeks. All data points are the means±SEM.

The human PD-1 knock-in (hPD1 KI) mice (n=6/group) were engrafted subcutaneously with MC38-huPD-L1 (MC38 transfected with human PD-L1) cells. Antibody treatments were started when tumor volumes reached approximately 86 mm³. Tested antibodies: PL2 #3-mtIgG1 and PL3 #7-mtIgG1, were intraperitoneally injected into mice twice a week for 3 weeks. The data shown in FIG. 10 indicate that the anti-tumor activity of PL2 #3-mtIgG1 and PL3 #7-mtIgG1 is comparable to that of Atezolizumab Analog, which is equivalent to the anti-PD-L1 reference antibody.

Example 9

Binding of Anti-PD-L1 Antibodies to the Cell Surface of PD-L1 Expressing Cells

Human T cells were isolated from PBMC using MagniSort™ Human T Cell Enrichment kit (eBioscience). Isolated T cells were activated by 5 μg/mL phytohemagglutinin (PHA) for 6 days to stimulate the PD-L1 expression. Activated T cells were collected and incubated in FACS buffer (PBS with 2% FBS) with human Fc blocker (eBioscience) for 20 minutes at 4° C. After removing the blocking reagent, T cells were suspended in FACS buffer for staining process. Tumor cells (A375 and NCI-H292) were collected by trypsinizing cells from culture plates and washed with FACS buffer twice for cell staining.

Binding of anti-PD-L1 monoclonal antibodies were assessed by incubating the cells with the serial-diluted anti-PD-L1 monoclonal antibodies in FACS buffer (PBS with 2% FBS). The cells were washed with flow buffer and the binding was detected with a biotin-labeled rabbit anti-human IgG Fcγ Ab and streptavidin-PE. Flow cytometric analyses were performed using the Cytomics FC 500 (Beckman Coulter Inc.).

Figure 13A:
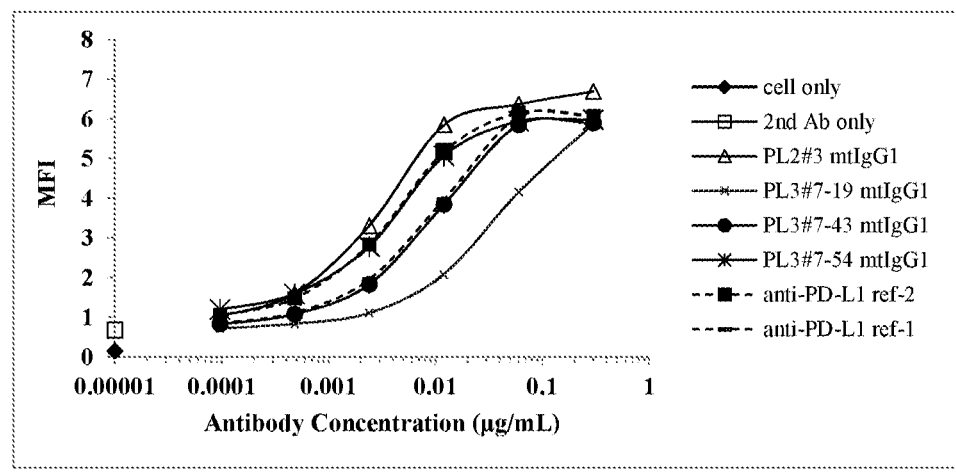
FIGS. 13A-13C. Binding of PL2 #3 and PL3 #7 variants to the cell surface of PD-L1 expressing cells. PL3 #7 variants were tested for the binding to the cell surface of activated T cells (FIG. 13A), A375 human melanoma cell line (FIG. 13B), and NCI-H292 human NSCLC cell line (FIG. 13C) by flow cytometry. Anti-PD-L1 reference antibody and HLX01 (anti-CD20 mAb) were used as the positive and negative control, respectively.
Figure 13B:
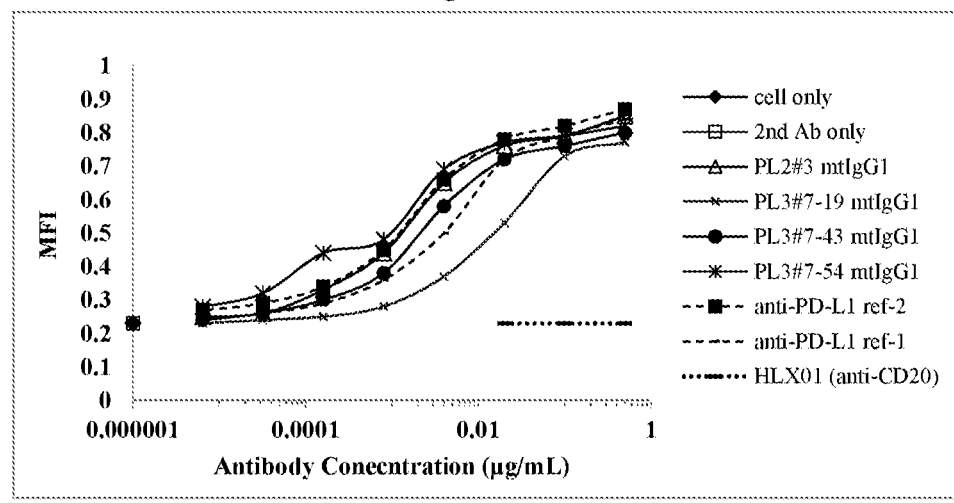
Figure 13C:
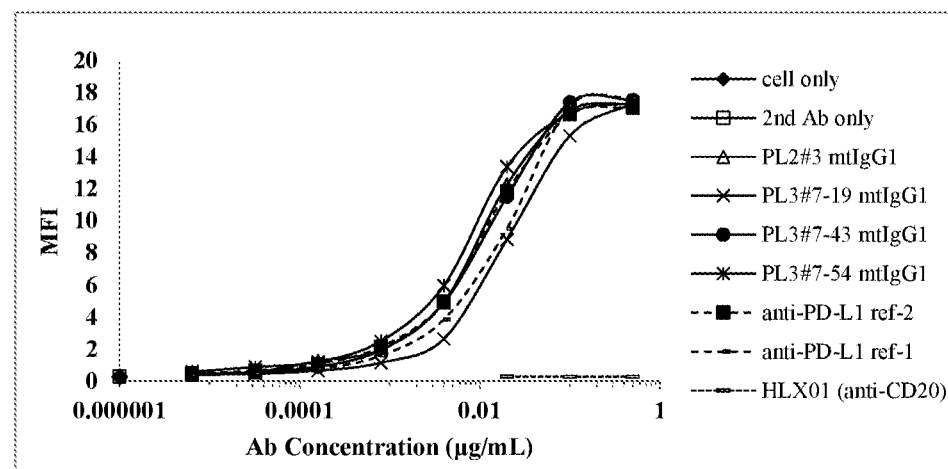

FIGS. 13A-13C show the binding of PL2 #3 and PL3 #7 variants to the cell surface of PD-L1 expressing cells: activated T cells (FIG. 13A), A375 human melanoma cell line (FIG. 13B), and NCI-H292 human NSCLC cell line (FIG. 13C). Anti-PD-L1 reference antibody and HLX01 (anti-CD20 mAb) were used as the positive and negative control, respectively. The rank of the binding activity for the activated T cells is: PL2 #3 mtIgG1 PL3 #7-54 mtIgG1>PL3 #7-43 mtIgG1>PL3 #7-19 mtIgG1. The rank of the binding activity for the A375 human melanoma cells is: PL3 #7-54 mtIgG1=PL2 #3 mtIgG1>PL3 #7-43 mtIgG1>PL3 #7-19 mtIgG1. The rank of the binding activity for the NCI-H292 human NSCLC cells is: PL3 #7-54 mtIgG1>PL2 #3 mtIgG1=PL3 #7-43 mtIgG1>PL3 #7-19 mtIgG1. These data conclude that all PL3 #7 variants and PL2 #3 bind to the surface of PD-L1 expressing cells.

Example 10

Tumor Growth Inhibition Activity of Anti-PD-L1 Antibody Variants in NCI-H292/PBMC Xenograft Model The in-vivo activity of anti-human PD-L1 antibodies was investigated in xenograft mouse models using immunocompromised NOD/SCID (non-obese diabetic/severe combined immunodeficiency) mice. Cancer cells and isolated human PBMC were mixed immediately before subcutaneous administration at the indicated effector-to-target (E:T) ratio. Each mouse was bilaterally inoculated with the mixtures of cancer cells and human PBMC. The first dose of the test article was administered intraperitoneally 2 hours after engraftment of cancer/effector cells. The animals received doses of the tested antibody twice a week for 3-4 weeks. The formation of tumor was observed in each animal two times a week. Tumors were measured by caliper and tumor volumes (V) were calculated using the following formula:

$$V(mm^3)=0.5\times(length(mm)\times width(mm)\times width(mm)/2).$$

Figure 14A:
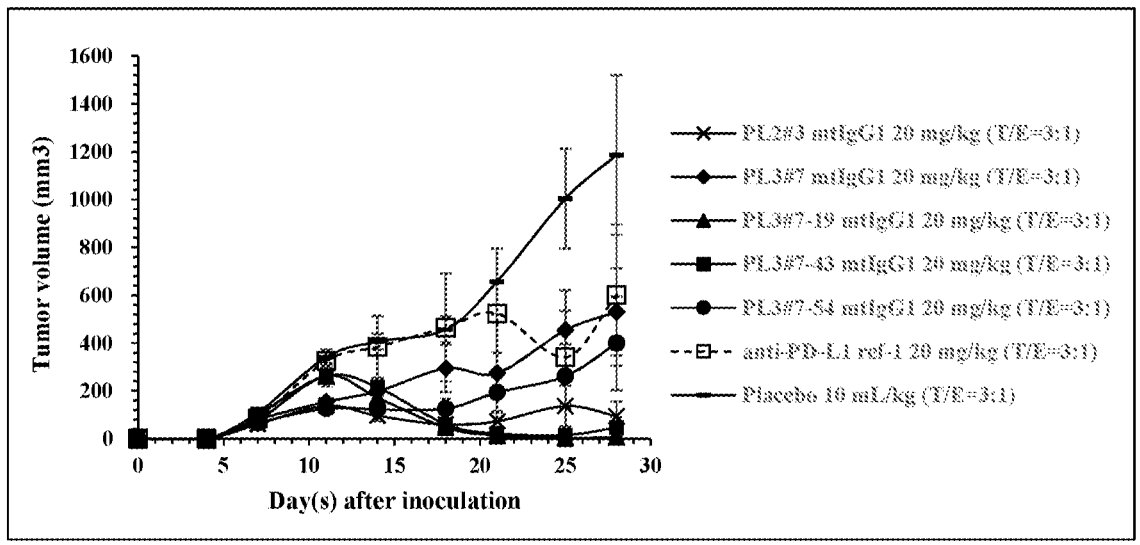
FIGS. 14A-14B. Tumor growth inhibition activity of PL2 #3 and PL3 #7 variants in NCI-H292/PBMC xenograft model. The mice (n=4/group) were engrafted subcutaneously with the mixture of human NSCLC cell lines NCI-H292 and freshly isolated human PBMC (cancer cells (T):PBMC (E)=3:1). Anti-PD-L1 antibodies were intraperitoneally injected into mice twice a week from day 0. Tumor growth curves were shown in FIG. 14A. The individual tumor volume at day 28 was presented in FIG. 14B. All data points are the means±SEM.
Figure 14B:
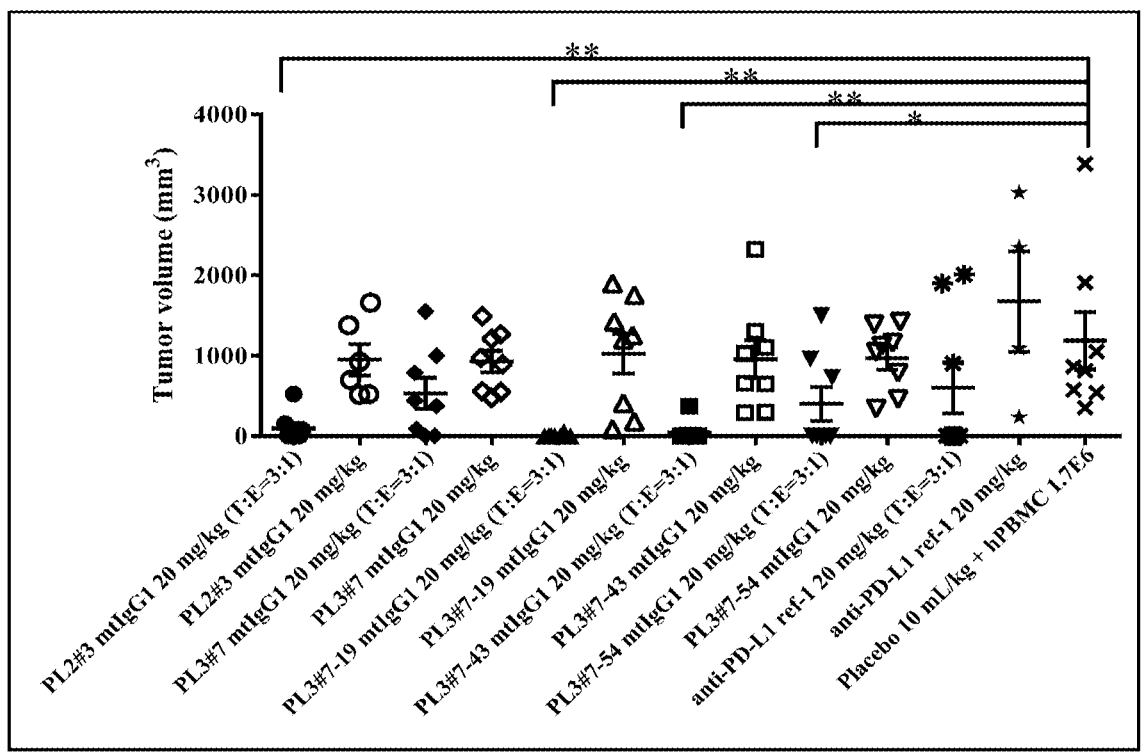

The mice (n=4/group) were engrafted subcutaneously with the mixture of human NSCLC cell lines NCI-H292 and freshly isolated human PBMC (cancer cells (T):PBMC (E)=3:1). Anti-PD-L1 antibodies were intraperitoneally injected into mice twice a week from day 0. Tumor growth curves were shown in FIG. 14A. The individual tumor volume at day 28 were presented in FIG. 14B. These data indicate that all the tested anti-PD-L1 antibody variants inhibit the tumor growth when the effector cells (hPBMC) were added. The variants PL2 #3, PL3 #7-19, and PL3 #7-43 show the similar in vivo tumor growth inhibition efficacy, which is superior to the PL3 #7-54 variant and the reference anti-PD-L1 antibody. The anti-cancer effect of anti-PD-L1 mAbs were through the immune cells.

Example 11

Cross-Binding of Anti-Human PD-L1 Monoclonal Antibodies to Mouse Melanoma Cells

Binding of anti-PD-L1 monoclonal antibody was assessed by incubating the A375 melanoma cells (1.5E5 cells/test) with the serial-diluted antibodies in FACS buffer. The cells were washed with flow buffer and the binding was detected with a FITC-labeled rabbit anti-human IgG Fcγ Ab. Flow cytometric analyses were performed using the Cytomics FC 500 (Beckman Coulter Inc.).

Figure 16:
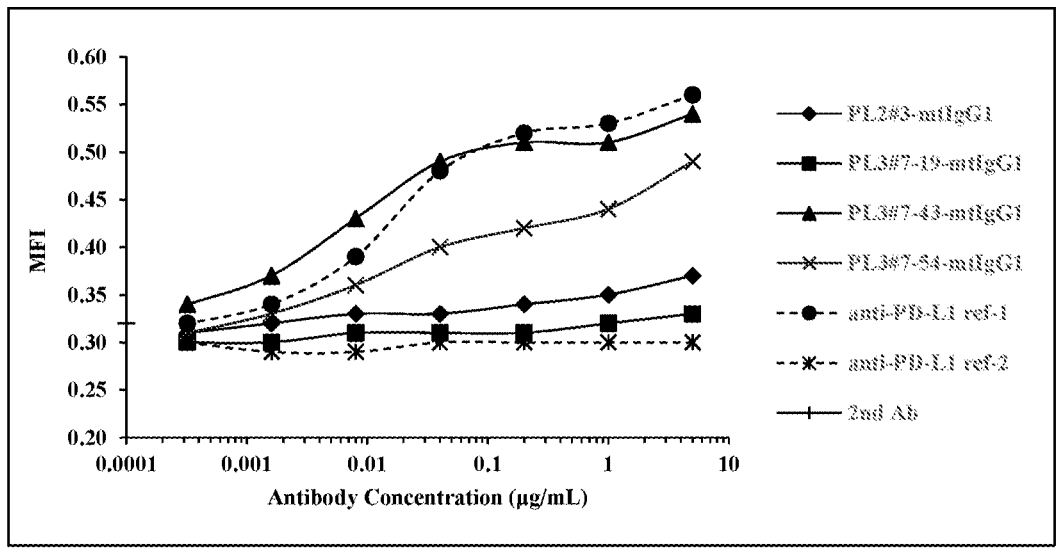
FIG. 16. Cross-binding of anti-human PD-L1 monoclonal antibodies to mouse melanoma cells. PL2 #3 and PL3 #7 variants were tested for the binding to mouse PD-L1 expressing melanoma cells (B16-F10) by flow cytometry. Anti-PD-L1 reference antibodies were used as the positive and negative control, respectively.

The PL2 #3 and PL3 #7 variants were tested for the binding to mouse PD-L1 expressing melanoma cells (B16-F10) by flow cytometry. Anti-PD-L1 reference antibodies were used as the positive and negative control, respectively. The data shown in FIG. 16 indicate that PL3 #7-43 and PL3 #7-54 variants cross-bind to mouse PD-L1, while PL2 #3 and PL3 #7-19 variants have no significant cross-reactivity with mouse melanoma cells.

Example 12

Cynomolgus Monkey PD-L1 Cross-Binding of Anti-PD-L1 Variants

The recombinant cynomolgus monkey PD-L1_ECD Fc-fusion proteins were purchased from Sino Biological Inc. PD-L1_ECD/Fc (9 ng per well) were immobilized onto 96-well assay plat by incubating overnight at 4° C. Non-specific binding sites were blocked using 5% skim milk in PBS for one hour at room temperature. After washing plates three times with PBST, indicated concentrations of anti-PD-L1 antibodies and HLX01 (negative control) were incubated with the immobilized proteins for one hour at room temperature. The plates were washed three times with PBST and then incubated for one hour at room temperature with peroxidase-labeled goat anti-human IgG F(ab)'2 (Jackson ImmunoResearch Laboratories) diluted 1/10,000 in PBS. After washing, plates were developed using TMB (eBioscience). The absorbance was read at the wavelength of 450 nm by Varioskan LUX microplate reader (Thermo Scientific).

Figure 17A:
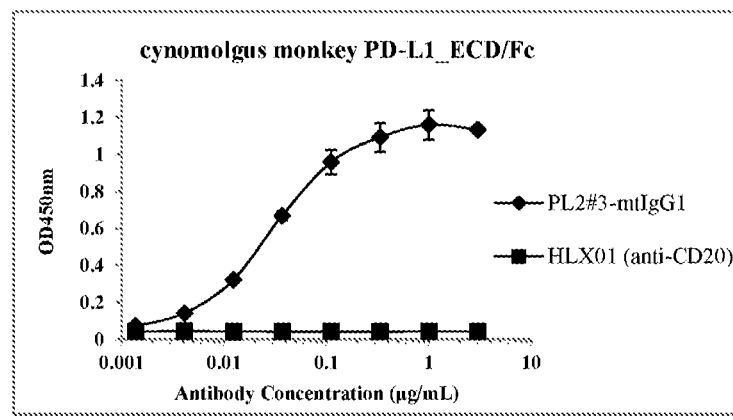
FIGS. 17A-17B. Cynomolgus monkey PD-L1 cross-binding of PL2 #3 (FIG. 17A) and PL3 #7 variants (FIG. 17B). PL2 #3 and PL3 #7 variants were tested for the binding to recombinant cynomolgus monkey PD-L1_ECD Fc-fusion proteins by ELISA. HLX01 (anti-CD20 mAb) were used as the negative control. All data points are the average of triplicate±SD.
Figure 17B:
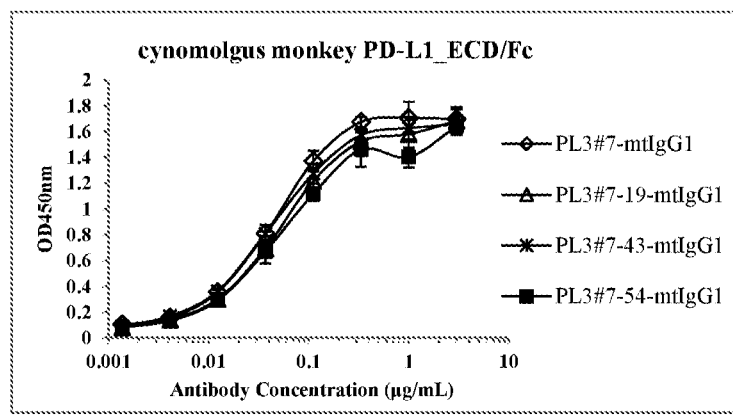

The PL2 #3 and PL3 #7 variants were tested for the binding to recombinant cynomolgus monkey PD-L1_ECD Fc-fusion proteins by ELISA. HLX01 (anti-CD20 mAb) was used as the negative control. The data shown in FIG. 17 indicate that the PL2 #3 and PL3 #7 variants cross-react with cynomolgus monkey PD-L1.

Example 13

Constructing De-Glycosylated PL3 #7-19 Variants and PL3 #7-43 Variants

PL3 #7-19 and PL3 #7-43 were two leading variants derived from PL3 #7 but needed to be subjected to further mutagenesis in an attempt to eliminate undesirable N-glycosylation sites within L-CDR2 region. N-glycosylation occurs at the sequon N—X—S/T. Since the N-glycosylation sites in parental PL3 #7-19 and PL3 #7-43 were encoded as N—S-T and N—R—S, the engineering was conducted either by mutating the second S/T from the N to the identical or similar amino acid in PL3 #7, that is, mutating the N—S-T and N—R—S to N—S—N/Q and N—R—P for PL3 #7-19 and PL3 #7-43, respectively (i.e., PL3 #7-19 deglyco1, deglyco3 and PL3 #7-43 deglyco1), or by directly mutating N to Q for the N—X—S/T sequon, that is, mutating the N—S-T and N—R—S to Q-S-T and Q-R—S for PL3 #7-19 and PL3 #7-43, respectively (i.e., PL3 #7-19 deglyco2 and PL3 #7-43 deglyco2). After that, removal of N-glycosylation sites on L-CDR2 were verified with liquid chromatography-mass spectrometry (LC-MS) and SDS-PAGE (data not shown).

Amino acid sequence alignment of light chain variable regions of de-glycosylated version of PL3 #7-19 variants and PL3 #7-43 variants is shown in FIG. 18. Sequence alignment of light chains of these de-glycosylated variants was listed and CDRs (Complementary Determining Regions) were marked in bold and underlined text. Heavy chains of them were unchanged and identical as their parental variants (sequence alignment not shown here). Binding activity to human PD-L1 of these de-glycosylated variants was determined with flow cytometry and Octet in the subsequent experiments.

Example 14

Whole Cell Binding of De-Glycosylated PL3 #7-19 Variants and PL3 #7-43 Variants

Binding of tested de-glycosylated variants was assessed by incubating the PD-L1 expressing CHO-S cells (2E5 cells/well) with the serial-diluted antibodies in FACS buffer (PBS with 1% FBS) at 4° C. for 30 minutes. These cells were washed with flow buffer and then stained with anti-human IgG Fc-FITC (1:500×) at 4° C. for 30 minutes to detect antibody binding on the cell surface. Flow cytometric analyses were performed using CytoFlex (Beckman Coulter Inc.).

Whole cell binding of de-glycosylated version of PL3 #7-19 variants and PL3 #7-43 variants are shown in FIGS. 19(A) and (B). PL3 #7-19 and PL3 #7-43 were two leading variants but require engineering in order to remove undesirable N-glycosylation sites within L-CDR2 region (See above Example 13). Whole cell binding activity to PD-L1 transfected CHO-S cells of the resultant three de-glycosylated variants for PL3 #7-19 (i.e., PL3 #7-19 deglyco1, deglyco2, deglyco3) and two de-glycosylated variants for PL3 #7-43 (i.e., PL3 #7-43 deglyco1, deglyco2) were determined with flow cytometry. All the de-glycosylated antibody variants tested here were in N297A mutant of human IgG1 Fc backbone. In-house anti-PD-1 antibody (i.e., HLX10) was used as the negative control.

The data shown in FIGS. 19(A) and (B) illustrate that the whole cell binding activity of de-glycosylated PL3 #7-19 and PL3 #7-43 variants was not affected by removal of N-glycosylation sites within the L-CDR2 region.

Example 15

Figure 20A:
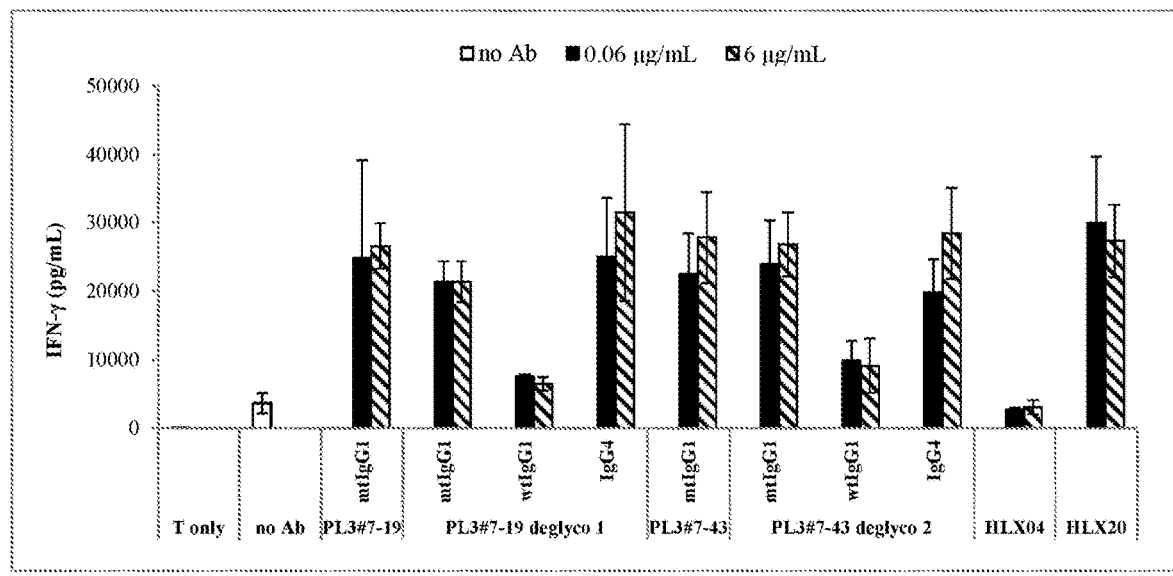
FIGS. 20A-20B. The efficacy of different IgG isotypes of PL3 #7-19 deglyco 1 and PL3 #7-43 deglyco2 in a mixed leukocyte reaction (MLR). Different IgG isotypes of PL3 #7-19 deglyco1 and PL3 #7-43 deglyco2 were tested using MLR assay. HLX04 and HLX20 (PL2 #3) were used as the negative and positive control antibody respectively. The bar graphs show the secreted IFN-γ (FIG. 20A) and IL-2 (FIG. 20B) induced by tested antibodies.
Figure 20B:
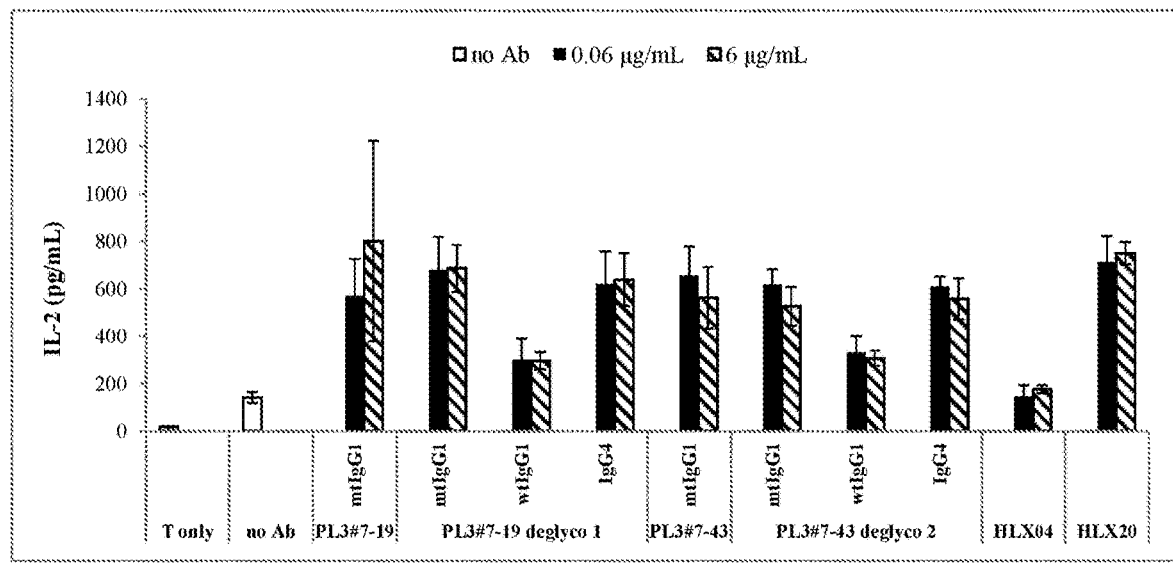

IgG Isotypes of PL3 #7-19 Deglyco 1 and PL3 #7-43 Deglyco 2 in Mixed Leukocyte Reaction The efficacy of different IgG isotypes of PL3 #7-19 deglyco1 and PL3 #7-43 deglyco2 was tested using mixed leukocyte reaction (MLR) assay, and the results were shown in FIGS. 20(A) and (B). HLX04 and HLX20 (PL2 #3) were used as the negative and positive control antibody respectively. The bar graphs show the secreted IFN-γ (FIG. 20A) and IL-2 (FIG. 20B) induced by tested antibodies.

Like glycosylated PL3 #7-19 mtIgG1 and PL3 #7-43 mtIgG1, the mtIgG1 and IgG4 isotypes of de-glycosylated PL3 #7-19 and PL3 #7-43 significantly enhance the cytokine secretion in MLR. The wild-type IgG1 of PL3 #7-19 deglyco 1 and PL3 #7-43 deglyco 1 showed lower enhancement of cytokine release, which may be due to the potential ADCC effect of wild-type IgG1 on T cells.

Example 16

Figure 21A:
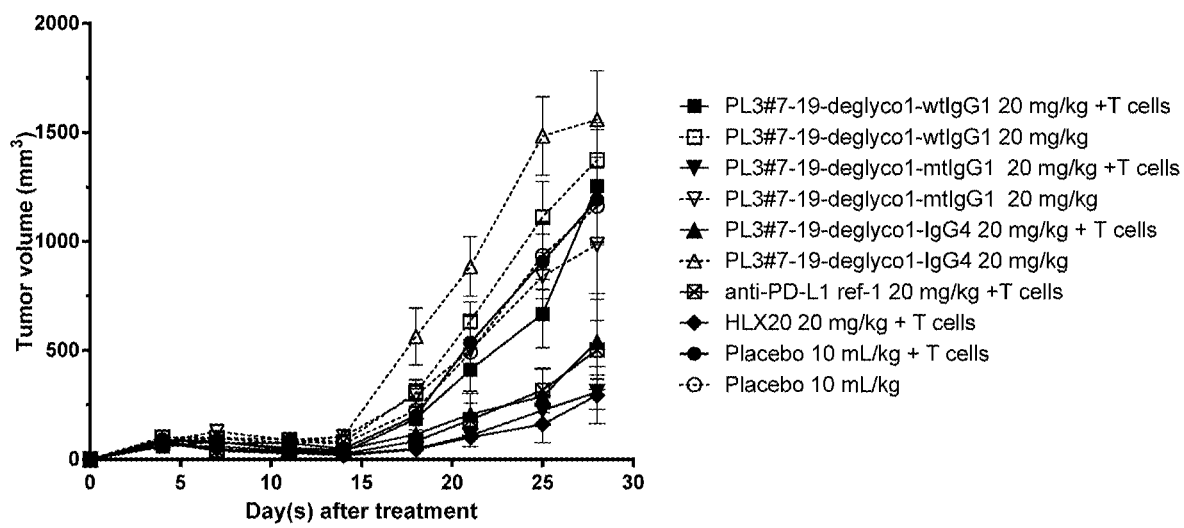
FIGS. 21A-21D. Tumor Growth Inhibition Activity of de-glycosylated PL3 #7-19 and PL3 #7-43 variants in A375/antigen-specific T cell xenograft model. The mice (n=5/group) were engrafted subcutaneously with the mixture of human melanoma cell lines A375 and antigen-specific T cells (T cells:cancer cells=1:100). Tested antibodies were intraperitoneally injected into mice twice a week from day 0. The tumor growth of mice treated with de-glycosylated PL3 #7-19 and PL3 #7-43 variants were shown in FIG. 21A and FIG. 21C, respectively. The individual tumor volume at day 28 was presented in FIG. 21B and FIG. 21D, respectively. All data points are the means±SEM.
Figure 21B:
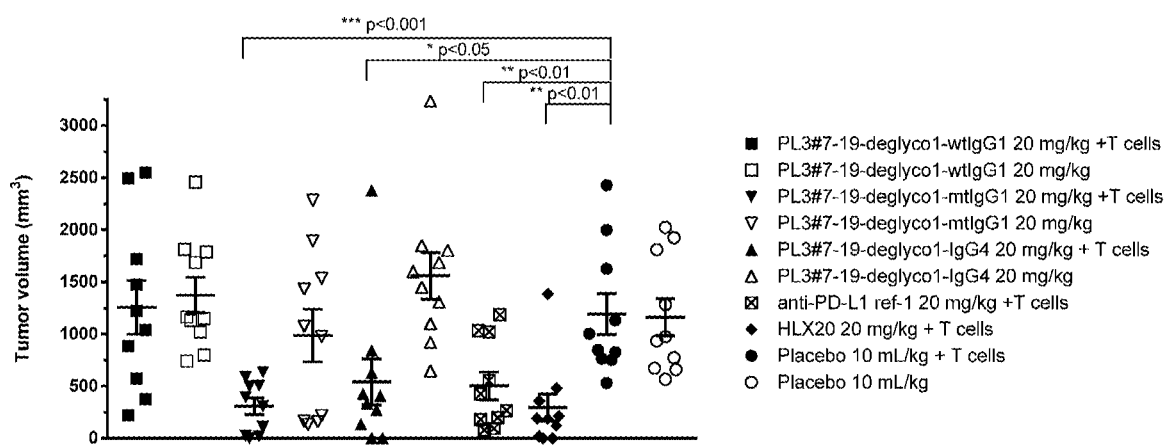
Figure 21C:
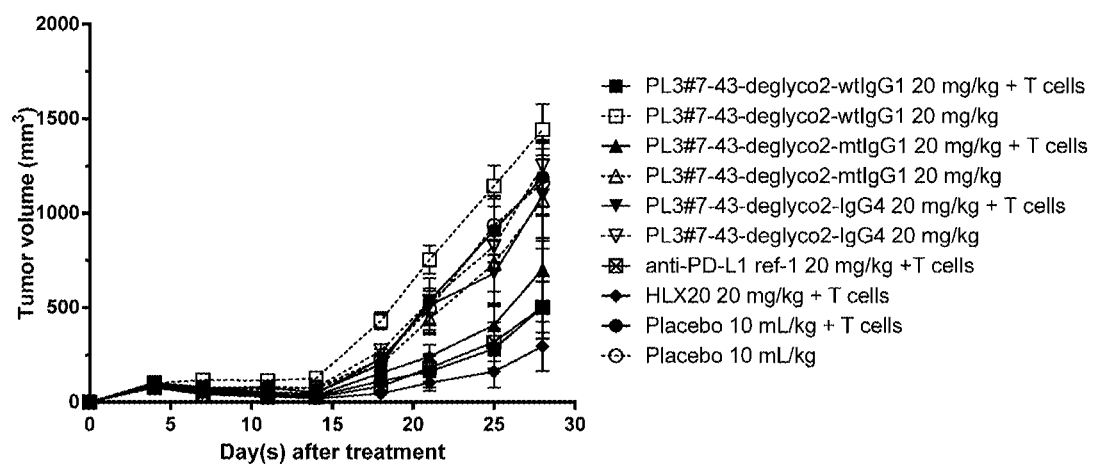
Figure 21D:
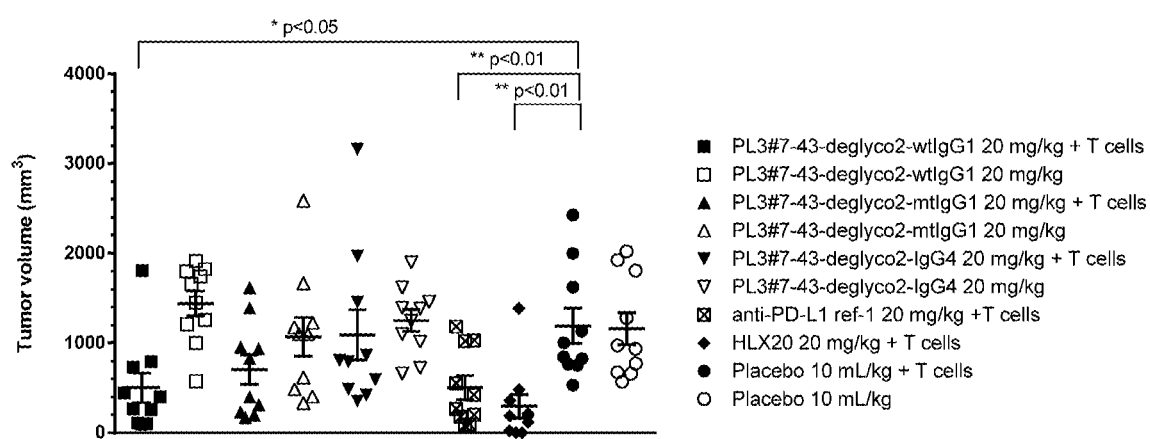

Tumor Growth Inhibition Activity of De-Glycosylated PL3 #7-19 and PL3 #7-43 Variants in A375/Antigen-Specific T-Cell Xenograft Model The mice (n=5/group) were engrafted subcutaneously with the mixture of human melanoma cell lines A375 and antigen-specific T cells (T cells:cancer cells=1:100). Tested antibodies were intraperitoneally injected into mice twice a week from day 0. The tumor growth of mice treated with de-glycosylated PL3 #7-19 and PL3 #7-43 variants were shown in FIGS. 21A and 21C, respectively. The individual tumor volume at day 28 was presented in FIGS. 21B and 21D, respectively. All data points are the means±SEM.

The data shown in these figures indicate that the anti-tumor efficacy of PL3 #7-19 deglyco 1 mtIgG1 and IgG4 variants, as well as PL3 #7-43 deglyco 2 wtIgG1, were comparable to that of HLX20 (PL2 #3) in A375/antigen-specific T cell xenograft model.

Example 17

Tumor Growth Inhibition Activity of Anti-PD-L1 mAb with Anti-VEGF mAb in NSCLC Xenograft Mice Model The in vivo activity of anti-human PD-L1 antibodies was investigated in xenograft mouse models using immunocompromised NOD/SCID (non-obese diabetic/severe combined immunodeficiency) mice. Cancer cells and isolated human PBMC were mixed immediately before subcutaneous administration at the indicated effector-to-target (E:T) ratio. Each mouse was bilaterally inoculated with the mixtures of cancer cells and human PBMC. Four animals were assigned to each experimental group. The first dose of the test article was administered intraperitoneally 1 day after engraftment of cancer/effector cells. The animals received doses of the test article twice a week for 3-4 weeks. The formation of tumor was observed in each animal two times a week. Tumors were measured by caliper and tumor volumes (V) were calculated using the following formula:

$$V(mm^3)=0.5\times(length(mm)\times width(mm)\times width(mm)/2)$$

Figure 22A:
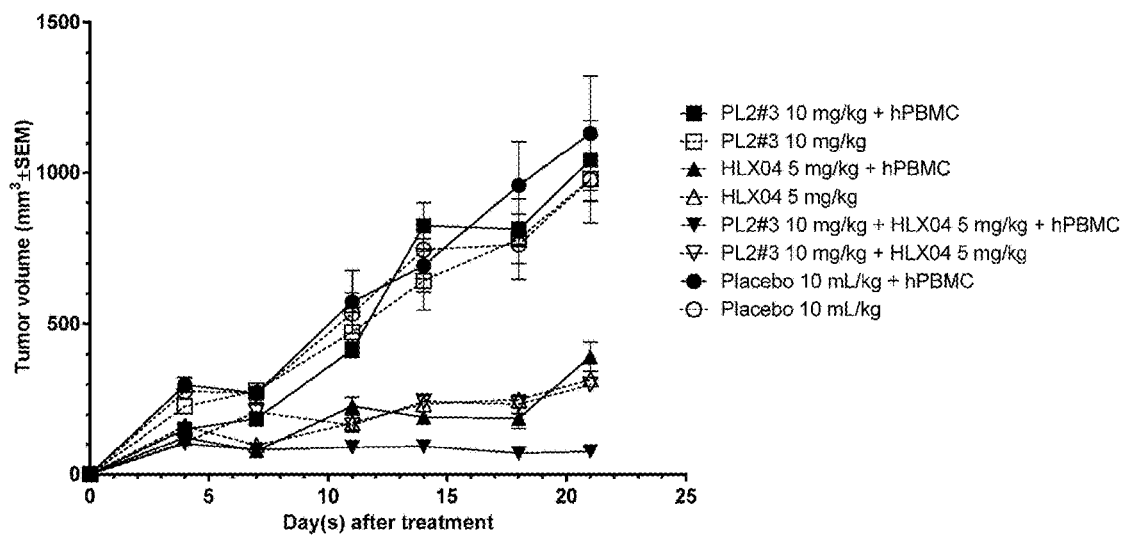
FIGS. 22A-22B. Tumor Growth Inhibition Activity of anti-PD-L1 mAb plus anti-VEGF mAb in NSCLC xenograft mice model. The mice (n=5/group) were engrafted subcutaneously with the mixture of human NSCLC cells NCI-H292 and freshly isolated human PBMC (cancer cells: PBMC=3:1). Anti-PD-L1 (PL2 #3), and anti-VEGF (HLX04) antibodies were intraperitoneally injected into mice twice a week from day 1. Tumor growth curves were shown in FIG. 22A. The individual tumor volume at day 21 was presented in FIG. 22B. All data points are the means±SEM.
Figure 22B:
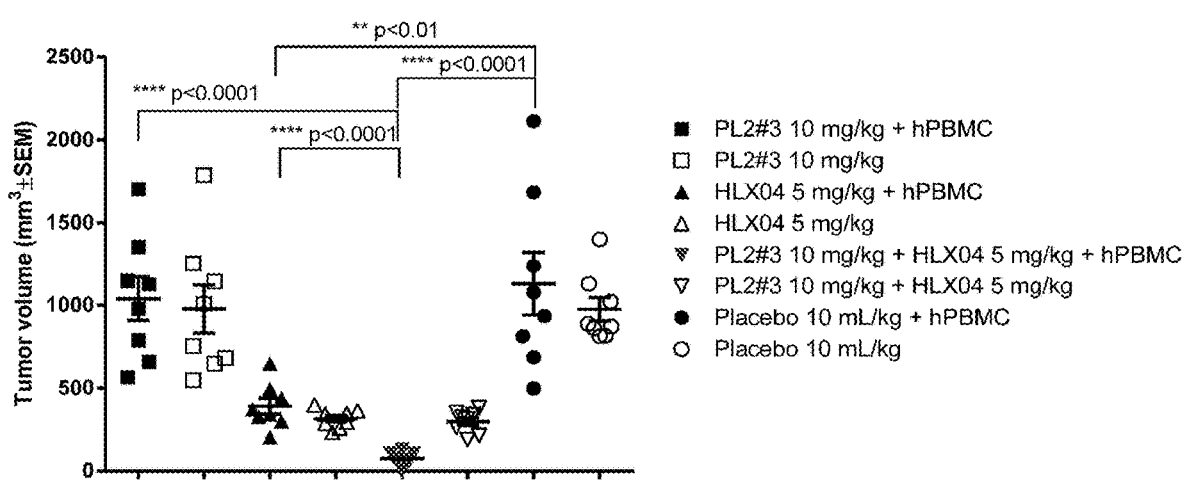

The mice (n=5/group) were engrafted subcutaneously with the mixture of human NSCLC cells NCI-H292 and freshly isolated human PBMC (cancer cells:PBMC=3:1). Anti-PD-L1 (PL2 #3) and anti-VEGF (HLX04) antibodies were intraperitoneally injected into mice twice a week from day 1. Tumor growth curves were shown in FIG. 22A. The individual tumor volume at day 21 was presented in FIG. 22B. All data points are the means±SEM.

These data illustrate that anti-PD-L1 mAb, PL2 #3, in combination with anti-VEGF mAb, HLX04, suppresses tumor growth of NCI-H292 xenografts more effectively than either agent used alone.

Example 18

Determination of Equilibrium Dissociation Constant ($K_D$) of De-glycosylated PL3 #7-19 and PL3 #7-43 Variants N-glycosylation occurs at the sequon N—X—S/T. Therefore, the N-glycosylation sites in parental PL3 #7-19 and PL3 #7-43 were located in L-CDR2. Removal of N-glycosylation sites was conducted by mutating the S/T in the sequon back to the identical or similar amino acid as PL3 #7 (i.e., PL3 #7-19 deglyco1, deglyco3 and PL3 #7-43 deglyco1), or directly mutating glycosylated N to Q (i.e., PL3 #7-19 deglyco2 and PL3 #7-43 deglyco2). Except L-CDR2 that was engineered to eliminate N-glycosylation, L-CDR1, L-CDR3 and H-CDR1, H-CDR2, H-CDR3 regions of the de-glycosylated variants remained unchanged. All the de-glycosylated variants tested here were cloned in N297A mutant of human IgG1 Fc backbone to side-by-side compare with parental PL3 #7-19 and PL3 #7-43 variants.

Affinity and kinetics of de-glycosylated anti-PD-L1 variants (i.e., PL3 #7-19 deglyco1, deglyco2, deglyco3 and PL3 #7-43 deglyco1, deglyco2) were measured by bio-layer interferometry approach using an Octet RED96 (ForteBio) system with AHC anti-human-Fc capture sensors at 25° C. and agitation speed of 1000 rpm. Briefly, black 96-well plate was prepared with columns containing 200 μL/well of reagents required for determination of affinity. In general, Octet anti-human-Fc sensors were first placed in wells containing 1×Kinetics Buffer (PBS, 0.1% BSA, 0.02% Tween-20, pH 7.4) for 180 seconds to establish a baseline.

Sensors were then transferred to wells containing 10 μg/mL anti-PD-L1 variants for 600 seconds to load the anti-human-Fc tips. Sensors were then placed in fresh 1×Kinetics Buffer for 180 seconds to establish a baseline. Association was then measured by incubating the sensors for 3 minutes in wells containing hPD-L1-His followed by transferring to wells containing 1×Kinetics Buffer for 10 minutes to measure dissociation. Sensors were then regenerated by 3×5 second incubations in Regeneration Buffer (10 mM Glycine, pH 1.5) followed by a 5 second incubation in 1×Kinetics Buffer each time. Regeneration was repeated before measurement of each association/dissociation cycle. Kinetics (ka, kd, and $K_D$) were measured by global fitting four association/dissociation cycles of data obtained from 1:3 serial dilutions of hPD-L1-His from 21.3 nM to 0.79 nM (one association/dissociation cycle for one concentration) with a 1:1 Langmuir binding model. All data were analyzed with Octet Data Analysis Software v.9.0 and representative of two independent experiments performed in duplicate.

Table 12 shows association, dissociation kinetics and calculated affinity ($K_D$) of the de-glycosylated variants measured by the ForteBio Octet RED96 machine (Menlo Park, Calif., USA) using a bio-layer interferometry approach. Fold difference in affinity of the de-glycosylated variants versus parental variants with N-glycosylation sites in L-CDR2 was shown in Table 12 as well. All the data are representative of two independent experiments performed in duplicate. These data show that de-glycosylated variants had very similar binding affinity to parental PL3 #7-19 and PL3 #7-43. Affinity was not affected by the removal of N-glycosylation within L-CDR2.

TABLE 12

| Average (N = 2) | ka [1/(M · s)] | kd [1/s] | $K_D$ [M] | Fold Difference |
|---|---|---|---|---|
| PL3 #7-19 parental mtIgG1 | 3.28E+05 | 2.07E−04 | 6.19E−10 | 1.00 |
| PL3 #7-19 deglyco1 mtIgG1 | 3.84E+05 | 1.62E−04 | 4.17E−10 | 1.48 |
| PL3 #7-19 deglyco2 mtIgG1 | 4.15E+05 | 1.51E−04 | 3.69E−10 | 1.68 |
| PL3 #7-19 deglyco3 mtIgG1 | 5.06E+05 | 1.76E−04 | 3.56E−10 | 1.74 |
| PL3 #7-43 parental mtIgG1 | 6.28E+05 | 2.12E−04 | 3.45E−10 | 1.00 |
| PL3 #7-43 deglyco1 mtIgG1 | 6.12E+05 | 2.71E−04 | 4.39E−10 | 0.79 |
| PL3 #7-43 deglyco2 mtIgG1 | 6.00E+05 | 2.38E−04 | 3.95E−10 | 0.87 |

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

```
                      Sequence Listing

SEQ ID NO: 1  (PL1_LC AA sequence, See Figure 1A)

SEQ ID NO: 2  (PL2_LC AA sequence, See Figure 1A)

SEQ ID NO: 3  (PL3_LC AA sequence, See Figure 1A)

SEQ ID NO: 4  (PL6_LC AA sequence, See Figure 1A)

SEQ ID NO: 5  (PL8_LC AA sequence, See Figure 1A)

SEQ ID NO: 6  (PL12_LC AA sequence, See Figure 1A)

SEQ ID NO: 7  (PL15_LC AA sequence, See Figure 1A)

SEQ ID NO: 8  (PL1_HC AA sequence, See Figure 1B)

SEQ ID NO: 9  (PL2_HC AA sequence, See Figure 1B)

SEQ ID NO: 10 (PL3_HC AA sequence, See Figure 1B)

SEQ ID NO: 11 (PL6_HC AA sequence, See Figure 1B)

SEQ ID NO: 12 (PL8_HC AA sequence, See Figure 1B)

SEQ ID NO: 13 (PL12_HC AA sequence, See Figure 1B)

SEQ ID NO: 14 (PL15_HC AA sequence, See Figure 1B)

SEQ ID NO: 15 (PL2#3_VL nt sequence)
CAGTCTGTCGTGACGCAGCCGCCCTCAATGTCAGCGGCCCCAGGACAGAGAGTCAC
CATCTCCTGCTCTGGAAGCAGCTCCTACATTGAAAGTTCTTACGTCGGGTGGTACCA
GCAACTCCCAGGAACAGCCCCCAGACTCCTCATTTATGACGATGATATGCGACCCTC
AGGGATCCCTGACCGATTCTCTGGCTCCAAGTCTGGCACGTCAGCCACCCTGGCCAT
CACCGGACTCCAGACTGGGGACGAGGCCGATTATTACTGCGAGATATGGCGGAGCG
GCCTGGGAGGCGTCTTCGGCGGAGGGACCAAGCTGACCGTCCTA SEQ ID NO: 16 (PL2#3_VL AA sequence (Underscore: Kabat defined CDRs))
QSVVTQPPSMSAAPGQRVTISCSGSSSYIESSYVGWYQQLPGTAPRLLIYDDDMRPSGIP
DRFSGSKSGTSATLAITGLQTGDEADYYCEIWRSGLGGVFGGGTKLTVL SEQ ID NO: 17 (PL2#3_VH nt sequence)
GAGGTTCAGCTGGTACAATCTGGGGGAGGCCTGGTCAAGCCTGGGGGGTCCCTGAG
ACTCTCCTGTGCAGCCTCTGGATTCACCTTCAGTAGTTATACTATGAACTGGGTCCGC
```

| Sequence Listing |
|---|

```
CAGGCTCCAGGGAAGGGCCTGGAGTGGGTCTCATCCATTAGTAGTGGTAGTGATTAC
TTATACTACGCAGACTCTGTGAAGGGCCGATTCACCATCTCCAGGGACAACGCCAA
GAACTCACTGTATCTGCAAATGAACAGCCTGAGAGCCGAGGACACGGCCGTGTATT
ACTGTGCGAGAAACGAACTACGGTGGTATCCACAAGCAGGTGCTTTTGATCGATGG
GGCCAAGGGACAATGGTCACCGTCTCAAGC

SEQ ID NO: 18 (PL2#3_VH AA sequence (Underscore: Kabat defined CDRs))
EVQLVQSGGGLVKPGGSLRLSCAASGFTFSSYTMNWVRQAPGKGLEWVS**SISSGSDYL
YYADSVKGRFTISRDNAKNSLYLQMNSLRAEDTAVYYCARNELRWYPQAGAFDR**WG
QGTMVTVSS SEQ ID NO: 19 (PL3#7_VL nt sequence)
CAGTCTGTCGTGACGCAGCCGCCCCCAGTGTCTGGGGCCCCAGGGCAGAGGGTCAC
CATCTCCTGCACTGGGAGCAGCTCCAACATCGGGGCAGGTTATGATGTACACTGGTA
CCAGCAGCTTCCAGGAACAGCCCCCAAACTCCTCATCTATGGTAACAGCAATCGGCC
CTCAGGGGTCCCTGACCGATTCTCTGGCTCCAAGTCTGGCACCTCAGCCTCCCTGGC
CATCACTGGGCTCCAGGCTGAGGATGAGGCTGATTATTACTGCCAGACTTATGACAG
CAGCCTGAGTGCCCGGGTGGTATTCGGCGGAGGGACCAAGCTGACCGTCCTA SEQ ID NO: 20 (PL3#7_VL AA sequence (Underscore: Kabat defined CDRs))
QSVVTQPPPVSGAPGQRVTISCTGSSSNIGAGYDVHWYQQLPGTAPKLLIYGNSNRPSG
VPDRFSGSKSGTSASLAITGLQAEDEADYYCQTYDSSLSARVVFGGGTKLTVL SEQ ID NO: 21 (PL3#7_VH nt sequence)
CAGGTCCAGCTGGTGCAATCTGGGGCTGAGGTGAAGAAGCCTGGGTCCTCGGTGAA
GGTCTCCTGCAAGGCTTCTGGAGGCACCTTCAGCAGCTATCCGATCAGCTGGGTGCG
ACAGGCCCCTGGACAAGGGCTTGAGTGGATAGGAAGGATCATCCCTATCCTTGGGA
TAGCAAACTACGCACAGAAGTTCCAGGGCAGAGTCACGATTACCGCGGACAAATCC
ACGAGCACAGCCTACATGGAGCTGAGCAGCCTGAGATCTGAGGACACGGCCGTGTA
TTACTGTGCGAGGTCTAGAGATGGCTACGCTTTTGGTGCTTTTGATATCTGGGGCCA
AGGAACCCTGGTCACCGTCTCAAGC SEQ ID NO: 22 (PL3#7_VH AA sequence (Underscore: Kabat defined CDRs))
QVQLVQSGAEVKKPGSSVKVSCKASGGTFSSYPISWVRQAPGQGLEWIG**RIIPILGIAN
YAQKFQGRVTITADKSTSTAYMELSSLRSEDTAVYYCARSRDGYAFGAFDI**WGQGTL
VTVSS SEQ ID NO: 23 (PL3#7-19_VL nt sequence)
CAGTCTGTCGTGACGCAGCCGCCCCCAGTGTCTGGGGCCCCAGGGCAGAGGGTCAC
CATCTCCTGCACTGGGAGCAGCTCCAACATCGGGGGGGGTTATGATGTACACTGGTA
CCAGCAGCTTCCAGGAACAGCCCCCAAACTCCTCATCTATGGTAACAGCACGCGGC
CCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCCAGACTTATGACA
GCAGCCTGAGTGCCACGGTGGTATTCGGCGGAGGGACCAAGCTGACCGTCCTA SEQ ID NO: 24 (PL3#7-19_VL AA sequence (Underscore: Kabat defined CDRs))
QSVVTQPPPVSGAPGQRVTISCTGSSSNIGGGYDVHWYQQLPGTAPKLLIYGNSTRPSG
VPDRFSGSKSGTSASLAITGLQAEDEADYYCQTYDSSLSATVVFGGGTKLTVL SEQ ID NO: 25 (PL3#7-19_VH nt sequence)
CAGGTCCAGCTGGTGCAATCTGGGGCTGAGGTGAAGAAGCCTGGGTCCTCGGTGAA
GGTCTCCTGCAAGGCTTCTGGAGGCACCTTCAGCAGCTATCCGATCAGCTGGGTGCG
ACAGGCCCCTGGACAAGGGCTTGAGTGGATGGGAAGGATCATCCCTATCCTTGGTAT
AGCAAACTACGCACAGAAGTTCCAGGGCAGAGTCACGATTACCGCGGACAAATCCA
CGAGCACAGCCTACATGGAGCTGAGCAGCCTGAGATCTGAGGACACGGCCGTGTAT
TACTGTGCGAGGTCTAGAGATGGCTACGCTTTTGGTGCTTTTGATGTGTGGGGCCAA
GGAACCCTGGTCACCGTCTCAAGC SEQ ID NO: 26 (PL3#7-19_VH AA sequence (Underscore: Kabat defined CDRs))
QVQLVQSGAEVKKPGSSVKVSCKASGGTFSSYPISWVRQAPGQGLEWMG**RIIPILGIAN
YAQKFQGRVTITADKSTSTAYMELSSLRSEDTAVYYCARSRDGYAFGAFDV**WGQGTL
VTVSS SEQ ID NO: 27 (PL3#7-43_VL nt sequence)
CAGTCTGTCGTGACGCAGCCGCCCCCAGTGTCTGGGGCCCCAGGGCAGAGGGTCAC
CATCTCCTGCACTGGGAGCAGCTCCAACGTGGGGCAGGTTATGATGTACACTGGTA
CCAGCAGCTTCCAGGAACAGCCCCCAAACTCCTCATCTATGGTAACAGCAATCGGTC
TTCAGGGGTCCCTGACCGATTCTCTGGCTCCAAGTCTGGCACCTCAGCCTCCCTGGC
CATCACTGGGCTCCAGGCTGAGGATGAGGCTGATTATTACTGCCAGACTTATGACAG
CAGCGGGAGTGCCCGGGTGGTATTCGGCGGAGGGACCAAGCTGACCGTCCTA SEQ ID NO: 28 (PL3#7-43_VL AA sequence (Underscore: Kabat defined CDRs))
QSVVTQPPPVSGAPGQRVTISCTGSSSNVGAGYDVHWYQQLPGTAPKLLIYGNSNRSS
GVPDRFSGSKSGTSASLAITGLQAEDEADYYCQTYDSSGSARVVFGGGTKLTVL
```

SEQ ID NO: 29 (PL3#7-43_VH nt sequence)
CAGGTCCAGCTGGTGCAATCTGGGGCTGAGGTGAAGAAGCCTGGGTCCTCGGTGAA
GGTCTCCTGCAAGGCTTCTGGAGGCACCTTCAGCAGCTATCCGATCAGCTGGGTGCG
ACAGGCCCCTGGACAAGGGCTTGAGTGGATGGGAAGGATCATCCCTATCCTTGGTAT
AGCAAACTACGCACAGAAGTTCCAGGGCAGAGTCACGATTACCGCGGACAAATCCA
CGAGCACAGCCTACATGGAGCTGAGCAGCCTGAGATCTGAGGACACGGCCGTGTAT
TACTGTGCGAGGTCTAGACCGGGCTACGCTTTTGGTGCTTTTGATATCTGGGGCCAA
GGAACCCTGGTCACCGTCTCAAGC SEQ ID NO: 30 (PL3#7-43_VH AA sequence (Underscore: Kabat defined CDRs))
QVQLVQSGAEVKKPGSSVKVSCKASGGTFSSYPISWVRQAPGQGLEWMG**RIIPILGIAN
YAQKFQGRVTITADKSTSTAYMELSSLRSEDTAVYYCARSRPGYAFGAFDI**WGQGTLV
TVSS SEQ ID NO: 31 (PL3#7-54_VL nt sequence)
CAGTCTGTCGTGACGCAGCCGCCCCCAGTGTCTGGGGCCCCAGGGCAGAGGGTCAC
CATCTCCTGCACTGGGAGCAGCTCCAACATCGGGCAGGGTTATGATGTACACTGGTA
CCAGCAGCTTCCAGGAACAGCCCCCAAACTCCTCATCTATGCTAACAGCAATCGGCC
CTCAGGGGTCCCTGACCGATTCTCTGGCTCCAAGTCTGGCACCTCAGCCTCCCTGGC
CATCACTGGGCTCCAGGCTGAGGATGAGGCTGATTATTACTGCCAGACTTATGACAG
CAGCCTGAGTGCCCGGGTGGTATTCGGCGGAGGGACCAAGCTGACCGTCCTA SEQ ID NO: 32 (PL3#7-54_VL AA sequence (Underscore: Kabat defined CDRs))
QSVVTQPPPVSGAPGQRVTISCTGSSSNIGQGYDVHWYQQLPGTAPKLLIYANSNRPSG
VPDRFSGSKSGTSASLAITGLQAEDEADYYCQTYDSSLSARVVFGGGTKLTVL SEQ ID NO: 33 (PL3#7-54_VH nt sequence)
CAGGTCCAGCTGGTGCAATCTGGGGCTGAGGTGAAGAAGCCTGGGTCCTCGGTGAA
GGTCTCCTGCAAGGCTTCTGGAGGCACCTTCAGCAGCTATCCGATCAGCTGGGTGCG
ACAGGCCCCTGGACAAGGGCTTGAGTGGATGGGAAGGATCATCCCTATCCTTGGTAT
AGCAGATTACGCACAGAAGTTCCAGGGCAGAGTCACGATTACCGCGGACAAATCCA
CGAGCACAGCCTACATGGAGCTGAGCAGCCTGAGATCTGAGGACACGGCCGTGTAT
TACTGTGCGAGGTCTAGACCGGGCTACGCTTTTGGTGCTTTTGATATCTGGGGCCAA
GGAACCCTGGTCACCGTCTCAAGC SEQ ID NO: 34 (PL3#7-54_VH AA sequence (Underscore: Kabat defined CDRs))
QVQLVQSGAEVKKPGSSVKVSCKASGGTFSSYPISWVRQAPGQGLEWMG**RIIPILGIAD
YAQKFQGRVTITADKSTSTAYMELSSLRSEDTAVYYCARSRPGYAFGAFDI**WGQGTLV
TVSS SEQ ID NO: 35 (CDR-L1 of PL1_LC): TGSSSNVGAGYDVH SEQ ID NO: 36 (CDR-L1 of PL2_LC): SGSSS.YIESSYVS SEQ ID NO: 37 (CDR-L1 of PL3_LC): TGSSSNIGAGYDVH SEQ ID NO: 37 (CDR-L1 of PL6_LC): TGSSSNIGAGYDVH SEQ ID NO: 38 (CDR-L1 of PL8_LC): QGDSLRSYYVS SEQ ID NO: 39 (CDR-L1 of PL12_LC): TRSSSNIGAGHDVH SEQ ID NO: 40 (CDR-L1 of PL15_LC): TGYSSNIGAGYDVH SEQ ID NO: 41 (CDR-L2 of PL1_LC): GNSNRPS SEQ ID NO: 42 (CDR-L2 of PL2_LC): DDDMRPS SEQ ID NO: 41 (CDR-L2 of PL3_LC): GNSNRPS SEQ ID NO: 41 (CDR-L2 of PL6_LC): GNSNRPS SEQ ID NO: 43 (CDR-L2 of PL8_LC): GKNNRPS SEQ ID NO: 41 (CDR-L2 of PL12_LC): GNSNRPS SEQ ID NO: 41 (CDR-L2 of PL15_LC): GNSNRPS SEQ ID NO: 44 (CDR-L3 of PL1_LC): QSYDSSLSGWV SEQ ID NO: 45 (CDR-L3 of PL2_LC): EIWDSGLGGV SEQ ID NO: 46 (CDR-L3 of PL3_LC): QSYDSSLSAPVV SEQ ID NO: 47 (CDR-L3 of PL6_LC): QSYDSSLSGGV

| Sequence Listing |
|---|
| SEQ ID NO: 48 (CDR-L3 of PL8_LC): NSRDSTGNLLRV |
| SEQ ID NO: 49 (CDR-L3 of PL12_LC): QSYDSSLTGVV |
| SEQ ID NO: 50 (CDR-L3 of PL15_LC): QSYDNSLSVSV |
| SEQ ID NO: 51 (CDR-H1 of PL1_HC): SYAIS |
| SEQ ID NO: 52 (CDR-H1 of PL2_HC): SYTMN |
| SEQ ID NO: 53 (CDR-H1 of PL3_HC): SYTIS |
| SEQ ID NO: 54 (CDR-H1 of PL6_HC): SYTIN |
| SEQ ID NO: 51 (CDR-H1 of PL8_HC): SYAIS |
| SEQ ID NO: 51 (CDR-H1 of PL12_HC): SYAIS |
| SEQ ID NO: 53 (CDR-H1 of PL15_HC): SYTIS |
| SEQ ID NO: 55 (CDR-H2 of PL1_HC): RIIPILGIANYAQKFQG |
| SEQ ID NO: 56 (CDR-H2 of PL2_HC): SISSGSDYLYYADSVKG |
| SEQ ID NO: 55 (CDR-H2 of PL3_HC): RIIPILGIANYAQKFQG |
| SEQ ID NO: 57 (CDR-H2 of PL6_HC): KIIPILGIADYAQMFKG |
| SEQ ID NO: 58 (CDR-H2 of PL8_HC): RIIPIFGTANYAQKFQG |
| SEQ ID NO: 55 (CDR-H2 of PL12_HC): RIIPILGIANYAQKFQG |
| SEQ ID NO: 55 (CDR-H2 of PL15_HC): RIIPILGIANYAQKFQG |
| SEQ ID NO: 59 (CDR-H3 of PL1_HC): EGSSGWLGVLDY |
| SEQ ID NO: 60 (CDR-H3 of PL2_HC): NELRWYPQAGAFDI |
| SEQ ID NO: 61 (CDR-H3 of PL3_HC): SRDGYSFGABDI |
| SEQ ID NO: 62 (CDR-H3 of PL6_HC): GGYVGYLNAFDI |
| SEQ ID NO: 63 (CDR-H3 of PL8_HC): EGVLDAFDI |
| SEQ ID NO: 64 (CDR-H3 of PL12_HC): GIGSYSFGAFDI |
| SEQ ID NO: 61 (CDR-H3 of PL15_HC): SRDGYSFGAFDI |
| SEQ ID NO: 65 (CDR-L1 of PL2#3_LC): SGSSSYIESSYVG |
| SEQ ID NO: 37 (CDR-L1 of PL3#7_LC): TGSSSNIGAGYDVH |
| SEQ ID NO: 66 (CDR-L1 of PL3#7-19_LC): TGSSSNIGGGYDVH |
| SEQ ID NO: 35 (CDR-L1 of PL3#7-43_LC): TGSSSNVGAGYDVH |
| SEQ ID NO: 67 (CDR-L1 of PL3#7-54_LC): TGSSSNIGQGYDVH |
| SEQ ID NO: 42 (CDR-L2 of PL2#3_LC): DDDMRPS |
| SEQ ID NO: 41 (CDR-L2 of PL3#7_LC): GNSNRPS |
| SEQ ID NO: 68 (CDR-L2 of PL3#7-19_LC): GNSTRPS |
| SEQ ID NO: 69 (CDR-L2 of PL3#7-43_LC): GNSNRSS |
| SEQ ID NO: 70 (CDR-L2 of PL3#7-54_LC): ANSNRPS |
| SEQ ID NO: 71 (CDR-L3 of PL2#3_LC): EIWRSGLGGV |
| SEQ ID NO: 72 (CDR-L3 of PL3#7_LC): QTYDSSLSARVV |
| SEQ ID NO: 73 (CDR-L3 of PL3#7-19_LC): QTYDSSLSATVV |
| SEQ ID NO: 74 (CDR-L3 of PL3#7-43_LC): QTYDSSGSARVV |
| SEQ ID NO: 72 (CDR-L3 of PL3#7-54_LC): QTYDSSLSARVV |

| Sequence Listing |
| --- |

SEQ ID NO: 52 (CDR-H1 of PL2#3_HC): SYTMN

SEQ ID NO: 75 (CDR-H1 of PL3#7_HC): SYPIS

SEQ ID NO: 75 (CDR-H1 of PL3#7-19_HC): SYPIS

SEQ ID NO: 75 (CDR-H1 of PL3#7-43_HC): SYPIS

SEQ ID NO: 75 (CDR-H1 of PL3#7-54_HC): SYPIS

SEQ ID NO: 56 (CDR-H2 of PL2#3_HC): SISSGSDYLYYADSVKG

SEQ ID NO: 55 (CDR-H2 of PL3#7_HC): RIIPILGIANYAQKFQG

SEQ ID NO: 55 (CDR-H2 of PL3#7-19_HC): RIIPILGIANYAQKFQG

SEQ ID NO: 55 (CDR-H2 of PL3#7-43_HC): RIIPILGIANYAQKFQG

SEQ ID NO: 76 (CDR-H2 of PL3#7-54_HC): RIIPILGIADYAQKFQG

SEQ ID NO: 77 (CDR-H3 of PL2#3_HC): NELRWYPQAGAFDR

SEQ ID NO: 78 (CDR-H3 of PL3#7_HC): SRDGYAFGAFDI

SEQ ID NO: 79 (CDR-H3 of PL3#7-19_HC): SRDGYAFGAFDV

SEQ ID NO: 80 (CDR-H3 of PL3#7-43_HC): SRPGYAFGAFDI

SEQ ID NO: 81 (CDR-H3 of PL3#7-54_HC): SRPGYAFGAFDI

SEQ ID NO: 82 (PL2#4_VL nt sequence)
CAGTCTGTCGTGACGCAGCCGCCCTCAATGTCAGCGGCCCCAGGACAGAGGGTCAC
CATCTCCTGCTCTGGAGTTAGCTCCTACATTGAAAGTTCTTATGTCTCCTGGTACCAG
CAACTCCCAGGAACAGCCCCCAGACTCCTCATTTATGACGATGATATGCGACCCTCA
GGGATCCCTGACCGATTCTCTGGCTCCAAGTCTGGCACGTCAGCCACCCTGGCCATC
ACCGGACTCCAGACTGGGGACGAGGCCGATTATTACTGCAAGATATGGGATAGCGG
CCTGGGAGGCGTCTTCGGCGGAGGGACCAAGCTGACCGTCCTA SEQ ID NO: 83 (PL2#4_VL AA sequence (Underscore: Kabat defined CDRs))
QSVVTQPPSMSAAPGQRVTISCSGVSSYIESSYVSWYQQLPGTAPRLLIYDDDMRPSGIP
DRFSGSKSGTSATLAITGLQTGDEADYYCKIWDSGLGGVFGGGTKLTVL SEQ ID NO: 84 (PL2#4_VH nt sequence)
GAGGTTCAGCTGGTACAATCTGGGGGAGGCCTGGTCAAGCCTGGGGGGTCCCTGAG
ACTCTCCTGTGCAGCCTCTGGATTCACCTTCAGTAGTTATACTATGAACTGGGTCCGC
CAGGCTCCAGGGAAGGGCCTGGAGTGGGTCTCATCCATTAGTAGTGGTAGTGATTAC
TTATACTACGCAGACTCTGTGAAGGGCCGATTCACCATCTCCAGGGACAACGCCAA
GAACTCACTGTATCTGCAAATGAACAGCCTGAGAGCCGAGGACACGGCCGTGTATT
ACTGTGCGAGAAACGAACTACGGTGGTATCCACTTGCAGGTGCTTTTGATATCTGGG
GCCAAGGGACAATGGTCACCGTCTCAAGC SEQ ID NO: 85 (PL2#4_VH AA sequence (Underscore: Kabat defined CDRs))
EVQLVQSGGGLVKPGGSLRLSCAASGFTFSSYTMNWVRQAPGKGLEWVS**SISSGSDYL
YYADSVKGRFTISRDNAKNSLYLQMNSLRAEDTAVYYCARNELRWYPLAGAFDI**WG
QGTMVTVSS SEQ ID NO: 86 (PL2#5_VL nt sequence)
CAGTCTGTCGTGACGCAGCCGCCCTCAATGTCAGCGGCCCCAGGACAGAGGGTCAC
CATCTCCTGCAGTGGAAGCAGCTCCTACATTGAAAGTTCTTATGTCTCATGGTACCA
GCAACTCCCAGGAACAGCCCCCAGACTCCTCATTTATGACGATGATATGCGACCCTC
AGGGATCCCTGACCGATTCTCTGGCTCCAAGTCTGGCACGTCAGCCACCCTGGCCAT
CACCGGACTCCAGACTGGGGACGAGGCCGATTATTACTGCGAGATATGGGATAGCC
GGCTGGGAGGCGTCTTCGGCGGAGGGACCAAGCTGACCGTCCTA SEQ ID NO: 87 (PL2#5_VL AA sequence (Underscore: Kabat defined CDRs))
QSVVTQPPSMSAAPGQRVTISCSGSSSYIESSYVSWYQQLPGTAPRLLIYDDDMRPSGIP
DRFSGSKSGTSATLAITGLQTGDEADYYCEIWDSRLGGVFGGGTKLTVL SEQ ID NO: 88 (PL2#5_VH nt sequence)
GAGGTTCAGCTGGTACAATCTGGGGGAGGCCTGGTCAAGCCTGGGGGGTCCCTGAG
ACTCTCCTGTGCAGCCTCTGGATTCACCTTCAGTAGTTATACTATGAACTGGGTCCGC
CAGGCTCCAGGGAAGGGCCTGGAGTGGGTCTCATCCATTAGTAGTGGTAGTGATTAC
TTATACTACGCAGACTCTGTGAAGGGCCGATTCACCATCTCCAGGGACAACGCCAA
GAACTCACTGTATCTGCAAATGAACAGCCTGAGAGCCGAGGACACGGCCGTGTATT
ACTGTGCGAGAAACGAACTACGGTGGTATCCATTTGCAGGTGCTTTTGATATTTGGG
GCCAAGGGACAATGGTCACCGTCTCAAGC

Sequence Listing

SEQ ID NO: 89 (PL2#5_VH AA sequence (Underscore: Kabat defined CDRs))
EVQLVQSGGGLVKPGGSLRLSCAASGFTFSSYTMNWVRQAPGKGLEWVS**SISSGSDYL
YYADSVKGRFTISRDNAKNSLYLQMNSLRAEDTAVYYCARNELRWYPFAGAFDI**WG
QGTMVTVSS SEQ ID NO: 90 (PL2#39_VL nt sequence)
CAGTCTGTCGTGACGCAGCCGCCCTCAATGTCAGCGGCCCCAGGACAGAGGGTCAC
CATCTCCTGCTCTGGAAGCAGCTCCTACATTACGAGTTCTTATGTCTCCTGGTACCAG
CAACTCCCAGGAACAGCCCCCAGACTCCTCATTTATGACGATGATATGCGACCCTCA
GGGATCCCTGACCGATTCTCTGGCTCCAAGTCTGGCACGTCAGCCACCCTGGCCATC
ACCGGACTCCAGACTGGGGACGAGGCCGATTATTACTGCAAGATATGGGATAGCGG
CCTGGGAGGCGTCTTCGGCGGAGGGACCAAGCTGACCGTCCTA SEQ ID NO: 91 (PL2#39_VL AA sequence (Underscore: Kabat defined CDRs))
QSVVTQPPSMSAAPGQRVTISCSGSSSYITSSYVSWYQQLPGTAPRLLIYDDDMRPSGIP
DRFSGSKSGTSATLAITGLQTGDEADYYCKIWDSGLGGVFGGGTKLTVL SEQ ID NO: 92 (PL2#39_VH nt sequence)
GAGGTTCAGCTGGTACAATCTGGGGGAGGCCTGGTCAAGCCTGGGGGGTCCCTGAG
ACTCTCCTGTGCAGCCTCTGGATTCACCTTCAGTAGTTATACTATGAACTGGGTCCGC
CAGGCTCCAGGGAAGGGCCTGGAGTGGGTCTCATCCATTAGTAGTGGTAGTGATTAC
TTATACTACGCAGACTCTGTGAAGGGCCGATTCACCATCTCCAGGGACAACGCCAA
GAACTCACTGTATCTGCAAATGAACAGCCTGAGAGCCGAGGACACGGCCGTGTATT
ACTGTGCGAGAAACGAACTACGGTGGTATCCAAAGGCAGGTGCTTTTGATATATGG
GGCCAAGGGACAATGGTCACCGTCTCAAGC SEQ ID NO: 93 (PL2#39_VH AA sequence (Underscore: Kabat defined CDRs))
EVQLVQSGGGLVKPGGSLRLSCAASGFTFSSYTMNWVRQAPGRGLEWVS**SISSGSDYL
YYADSVKGRFTISRDNAKNSLYLQMNSLRAEDTAVYYCARNELRWYPKAGAFDI**WG
QGTMVTVSS SEQ ID NO: 94 (CDR-L1 of PL2#4_LC): SGVSSYIESSYVS SEQ ID NO: 97 (CDR-L1 of PL2#5_LC): SGSSSYIESSYVS SEQ ID NO: 100 (CDR-L1 of PL2#39_LC): SGSSSYITSSYVS SEQ ID NO: 42 (CDR-L2 of PL2#4_LC): DDDMRPS SEQ ID NO: 42 (CDR-L2 of PL2#5_LC): DDDMRPS SEQ ID NO: 42 (CDR-L2 of PL2#39_LC): DDDMRPS SEQ ID NO: 95 (CDR-L3 of PL2#4_LC): KIWDSGLGGV SEQ ID NO: 98 (CDR-L3 of PL2#5_LC): EIWDSRLGGV SEQ ID NO: 95 (CDR-L3 of PL2#39_LC): KIWDSGLGGV SEQ ID NO: 52 (CDR-H1 of PL2#4_HC): SYTMN SEQ ID NO: 52 (CDR-H1 of PL2#5_HC): SYTMN SEQ ID NO: 52 (CDR-H1 of PL2#39_HC): SYTMN SEQ ID NO: 56 (CDR-H2 of PL2#4_HC): SISSGSDYLYYADSVKG SEQ ID NO: 56 (CDR-H2 of PL2#5_HC): SISSGSDYLYYADSVKG SEQ ID NO: 56 (CDR-H2 of PL2#39_HC): SISSGSDYLYYADSVKG SEQ ID NO: 96 (CDR-H3 of PL2#4_HC): NELRWYPLAGABDI SEQ ID NO: 99 (CDR-H3 of PL2#5_HC): NELRWYPFAGAFDI SEQ ID NO: 101 (CDR-H3 of PL2#39_HC): NELRWYPKAGAFDI SEQ ID NO: 102 (PL3#1_VL nt sequence)
CAGTCTGTCGTGACGCAGCCGCCCCCAGTGTCTGGGGCCCCAGGGCAGAGGGTCAC
CATCTCCTGCACTGGGAGCAGCTCCAACATCGGGGCAGGTTATGATGTACACTGGTA
CCAGCAGCTTCCAGGAACAGCCCCCAAACTCCTCATCTATGGTAACAGCAGGCGGC
CCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCCAGACCTATGACA
GCAGCCTGAGTCGTCCCGTGGTATTCGGCGGAGGGACCAAGCTGACCGTCCTA

Sequence Listing

SEQ ID NO: 103 (PL3#1_VL AA sequence (Underscore: Kabat defined CDRs))
QSVVTQPPPVSGAPGQRVTISC<u>TGSSSNIGAGYDVH</u>WYQQLPGTAPKLLIY<u>GNSRRPS</u>GV
PDRFSGSKSGTSASLAITGLQAEDEADYYC<u>QTYDSSLSRPVV</u>FGGGTKLTVL SEQ ID NO: 104 (PL3#1_VH nt sequence)
CAGGTCCAGCTGGTGCAATCTGGGGCTGAGGTGAAGAAGCCTGGGTCCTCGGTGAA
GGTCTCCTGCAAGGCTTCTGGAGGCACCTTCAGCAGCTATAGGATCAGCTGGGTGCG
ACAGGCCCCTGGACAAGGGCTTGAGTGGATGGGAAGGATCATCCCTATCCTTGGTAT
AGCAAACTACGCACAGAAGTTCCAGGGCAGAGTCACGATTACCGCGGACAAATCCA
CGAGCACAGCCTACATGGAGCTGAGCAGCCTGAGATCTGAGGACACGGCCGTGTAT
TACTGTGCGAGGTCTAGAGATGGCTACAGTGTGGGTGCTTTTGATTCGTGGGGCCAA
GGAACCCTGGTCACCGTCTCAAGC SEQ ID NO: 105 (PL3#1_VH AA sequence (Underscore: Kabat defined CDRs))
QVQLVQSGAEVKKPGSSVKVSCKASGGTFS<u>SYRIS</u>WVRQAPGQGLEWMG<u>RIIPILGIAN
YAQKFQG</u>RVTITADKSTSTAYMELSSLRSEDTAVYYCAR<u>SRDGYSVGAFDS</u>WGQGTLV
TVSS SEQ ID NO: 37 (CDR-L1 of PL3#1_LC): TGSSSNIGAGYDVH SEQ ID NO: 106 (CDR-L2 of PL3#1_LC): GNSRRPS SEQ ID NO: 107 (CDR-L3 of PL3#1_LC): QTYDSSLSRPVV SEQ ID NO: 108 (CDR-H1 of PL3#1_HC): SYRIS SEQ ID NO: 55 (CDR-H2 of PL3#1_HC): RIIPILGIANYAQKFQG SEQ ID NO: 109 (CDR-H3 of PL3#1_HC): SRDGYSVGAFDS SEQ ID NO: 110 (PL3#7-19 deglyco1_VL nt sequence (Underscore: L-CDR2))
CAGTCTGTCGTGACGCAGCCGCCCCCAGTGTCTGGGGCCCCAGGGCAGAGGGTCAC
CATCTCCTGCACTGGGAGCAGCTCCAACATCGGGGGGGGTTATGATGTACACTGGTA
CCAGCAGCTTCCAGGAACAGCCCCCAAACTCCTCATCTATGGTAACAGCAATCGGC
CCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCCAGACTTATGACA
GCAGCCTGAGTGCCACGGTGGTATTCGGCGGAGGGACCAAGCTGACCGTCCTA SEQ ID NO: 111 (PL3#7-19 deglyco1_VL AA sequence (Under-
score: Kabat defined CDRs))
QSVVTQPPPVSGAPGQRVTISCTGSSSNIGGGYDVHWYQQLPGTAPKLLIYGNSNRPSG

VPDRFSGSKSGTSASLAITGLQAEDEADYYCQTYDSSLSATVVFGGGTKLTVL

SEQ ID NO: 112 (PL3#7-19 deglyco2_VL nt sequence (Underscore: L-CDR2))
CAGTCTGTCGTGACGCAGCCGCCCCCAGTGTCTGGGGCCCCAGGGCAGAGGGTCAC
CATCTCCTGCACTGGGAGCAGCTCCAACATCGGGGGGGGTTATGATGTACACTGGTA
CCAGCAGCTTCCAGGAACAGCCCCCAAACTCCTCATCTATGGTCAGAGCACGCGG
CCCTCAGGGGTCCCTGACCGATTCTCTGGCTCCAAGTCTGGCACCTCAGCCTCCCTG
GCCATCACTGGGCTCCAGGCTGAGGATGAGGCTGATTATTACTGCCAGACTTATGAC
AGCAGCCTGAGTGCCACGGTGGTATTCGGCGGAGGGACCAAGCTGACCGTCCTA SEQ ID NO: 113 (PL3#7-19 deglyco2_VL AA sequence (Under-
score: Kabat defined CDRs))
QSVVTQPPPVSGAPGQRVTISCTGSSSNIGGGYDVHWYQQLPGTAPKLLIYGQSTRPSG

VPDRFSGSKSGTSASLAITGLQAEDEADYYCQTYDSSLSATVVFGGGTKLTVL

SEQ ID NO: 114 (PL3#7-19 deglyco3_VL nt sequence (Underscore: L-CDR2))
CAGTCTGTCGTGACGCAGCCGCCCCCAGTGTCTGGGGCCCCAGGGCAGAGGGTCAC
CATCTCCTGCACTGGGAGCAGCTCCAACATCGGGGGGGGTTATGATGTACACTGGTA
CCAGCAGCTTCCAGGAACAGCCCCCAAACTCCTCATCTATGGTAACAGCCAACGGC
CCTCAGGGGTCCCTGACCGATTCTCTGGCTCCAAGTCTGGCACCTCAGCCTCCCTGG
CCATCACTGGGCTCCAGGCTGAGGATGAGGCTGATTATTACTGCCAGACTTATGACA
GCAGCCTGAGTGCCACGGTGGTATTCGGCGGAGGGACCAAGCTGACCGTCCTA SEQ ID NO: 115 (PL3#7-19 deglyco3_VL AA sequence (Under-
score: Kabat defined CDRs))
QSVVTQPPPVSGAPGQRVTISCTGSSSNIGGGYDVHWYQQLPGTAPKLLIYGNSQRPSG

VPDRFSGSKSGTSASLAITGLQAEDEADYYCQTYDSSLSATVVFGGGTKLTVL

-continued

Sequence Listing

SEQ ID NO: 116 (PL3#7-43 deglyco1_VL nt sequence (Underscore: L-CDR2))
CAGTCTGTCGTGACGCAGCCGCCCCCAGTGTCTGGGGCCCCAGGGCAGAGGGTCAC
CATCTCCTGCACTGGGAGCAGCTCCAACGTGGGGGCAGGTTATGATGTACACTGGTA
CCAGCAGCTTCCAGGAACAGCCCCCAAACTCCTCATCTATGGTAACAGCAATCGGC

CGTCAGGGGTCCCTGACCGATTCTCTGGCTCCAAGTCTGGCACCTCAGCCTCCCTGG

CCATCACTGGGCTCCAGGCTGAGGATGAGGCTGATTATTACTGCCAGACTTATGACA
GCAGCGGAGTGCCCGGTGGTATTCGGCGGAGGGACCAAGCTGACCGTCCTA

SEQ ID NO: 117 (PL3#7-43 deglyco1_VL AA sequence (Underscore: Kabat defined CDRs))
QSVVTQPPPVSGAPGQRVTISCTGSSSNVGAGYDVHWYQQLPGTAPKLLIYGNSNRPSG

GVPDRFSGSKSGTSASLAITGLQAEDEADYYCQTYDSSGSARVVFGGGTKLTVL

SEQ ID NO: 118 (PL3#7-43 deglyco2_VL nt sequence (Underscore: L-CDR2))
CAGTCTGTCGTGACGCAGCCGCCCCCAGTGTCTGGGGCCCCAGGGCAGAGGGTCAC
CATCTCCTGCACTGGGAGCAGCTCCAACGTGGGGGCAGGTTATGATGTACACTGGTA
CCAGCAGCTTCCAGGAACAGCCCCCAAACTCCTCATCTATGGTAACAGCCAACGGT

CTTCAGGGGTCCCTGACCGATTCTCTGGCTCCAAGTCTGGCACCTCAGCCTCCCTGG

CCATCACTGGGCTCCAGGCTGAGGATGAGGCTGATTATTACTGCCAGACTTATGACA
GCAGCGGAGTGCCCGGTGGTATTCGGCGGAGGGACCAAGCTGACCGTCCTA

SEQ ID NO: 119 (PL3#7-43 deglyco2_VL AA sequence (Underscore: Kabat defined CDRs))
QSVVTQPPPVSGAPGQRVTISCTGSSSNVGAGYDVHWYQQLPGTAPKLLIYGNSQRSS

GVPDRFSGSKSGTSASLAITGLQAEDEADYYCQTYDSSGSARVVFGGGTKLTVL

We claim:

1. An anti-PD-L1 antibody comprising:
   i) a light chain (LC) variable domain sequence comprising the amino acid sequence set forth in SEQ ID NO: 16, and a heavy chain (HC) variable domain sequence comprising the amino acid sequence set forth in SEQ ID NO: 18;
   ii) a light chain (LC) variable domain sequence comprising the amino acid sequence set forth in SEQ ID NO: 20, and a heavy chain (HC) variable domain sequence comprising the amino acid sequence set forth in SEQ ID NO: 22;
   iii) a light chain (LC) variable domain sequence comprising the amino acid sequence set forth in SEQ ID NO: 24, and a heavy chain (HC) variable domain sequence comprising the amino acid sequence set forth in SEQ ID NO: 26;
   iv) a light chain (LC) variable domain sequence comprising the amino acid sequence set forth in SEQ ID NO: 28, and a heavy chain (HC) variable domain sequence comprising the amino acid sequence set forth in SEQ ID NO: 30;
   v) a light chain (LC) variable domain sequence comprising the amino acid sequence set forth in SEQ ID NO: 32, and a heavy chain (HC) variable domain sequence comprising the amino acid sequence set forth in SEQ ID NO: 34;
   vi) a light chain (LC) variable domain sequence comprising the amino acid sequence set forth in SEQ ID NO: 117, and a heavy chain (HC) variable domain sequence comprising the amino acid sequence set forth in SEQ ID NO: 30;
   vii) a light chain (LC) variable domain sequence comprising the amino acid sequence set forth in SEQ ID NO: 119, and a heavy chain (HC) variable domain sequence comprising the amino acid sequence set forth in SEQ ID NO: 30;
   viii) a light chain (LC) variable domain sequence comprising the amino acid sequence set forth in SEQ ID NO: 111, and a heavy chain (HC) variable domain sequence comprising the amino acid sequence set forth in SEQ ID NO: 26;
   ix) a light chain (LC) variable domain sequence comprising the amino acid sequence set forth in SEQ ID NO: 113, and a heavy chain (HC) variable domain sequence comprising the amino acid sequence set forth in SEQ ID NO: 26; or
   x) a light chain (LC) variable domain sequence comprising the amino acid sequence set forth in SEQ ID NO: 115, and a heavy chain (HC) variable domain sequence comprising the amino acid sequence set forth in SEQ ID NO: 26.

2. The anti-PD-L1 antibody of claim 1, comprising a light chain (LC) variable domain sequence comprising the amino acid sequence set forth in SEQ ID NO: 16, and a heavy chain (HC) variable domain sequence comprising the amino acid sequence set forth in SEQ ID NO: 18.

3. The anti-PD-L1 antibody of claim 1, comprising a light chain (LC) variable domain sequence comprising the amino acid sequence set forth in SEQ ID NO: 20, and a heavy chain (HC) variable domain sequence comprising the amino acid sequence set forth in SEQ ID NO: 22.

4. The anti-PD-L1 antibody of claim 1, comprising a light chain (LC) variable domain sequence comprising the amino acid sequence set forth in SEQ ID NO: 24, and a heavy chain (HC) variable domain sequence comprising the amino acid sequence set forth in SEQ ID NO: 26.

5. The anti-PD-L1 antibody of claim 1, comprising a light chain (LC) variable domain sequence comprising the amino acid sequence set forth in SEQ ID NO: 28, and a heavy chain (HC) variable domain sequence comprising the amino acid sequence set forth in SEQ ID NO: 30.

6. The anti-PD-L1 antibody of claim 1, comprising a light chain (LC) variable domain sequence comprising the amino acid sequence set forth in SEQ ID NO: 32, and a heavy chain (HC) variable domain sequence comprising the amino acid sequence set forth in SEQ ID NO: 34.

7. The anti-PD-L1 antibody of claim 1, comprising a light chain (LC) variable domain sequence comprising the amino acid sequence set forth in SEQ ID NO: 117, and a heavy chain (HC) variable domain sequence comprising the amino acid sequence set forth in SEQ ID NO: 30.

8. The anti-PD-L1 antibody of claim 1, comprising a light chain (LC) variable domain sequence comprising the amino acid sequence set forth in SEQ ID NO: 119, and a heavy chain (HC) variable domain sequence comprising the amino acid sequence set forth in SEQ ID NO: 30.

9. The anti-PD-L1 antibody of claim 1, comprising a light chain (LC) variable domain sequence comprising the amino acid sequence set forth in SEQ ID NO: 111, and a heavy chain (HC) variable domain sequence comprising the amino acid sequence set forth in SEQ ID NO: 26.

10. The anti-PD-L1 antibody of claim 1, comprising a light chain (LC) variable domain sequence comprising the amino acid sequence set forth in SEQ ID NO: 113, and a heavy chain (HC) variable domain sequence comprising the amino acid sequence set forth in SEQ ID NO: 26.

11. The anti-PD-L1 antibody of claim 1, comprising a light chain (LC) variable domain sequence comprising the amino acid sequence set forth in SEQ ID NO: 115, and a heavy chain (HC) variable domain sequence comprising the amino acid sequence set forth in SEQ ID NO: 26.

12. The anti-PD-L1 antibody of claim 1, comprising a Fab, Fab', a F(ab)'2, a single-chain Fv(scFv), a Fv fragment or an Fc sequence of a human IgG.

13. The anti-PD-L1 antibody of claim 1, which is a diabody, a linear antibody or a multispecific antibody.

14. The anti-PD-L1 antibody of claim 1, conjugated to a label selected from the group consisting of a radioisotope, a fluorescent dye and an enzyme.

15. The anti-PD-L1 antibody of claim 1, conjugated to a therapeutic agent selected from the group consisting of an anti-neoplastic agent, a chemotherapeutic agent, a growth inhibitory agent and a cytotoxic agent.

16. One or more isolated nucleic acid molecule encoding the anti-PD-L1 antibody of claim 1.

17. One or more expression vector comprising the isolated nucleic acid molecule of claim 16.

18. A cell or a cell line comprising the isolated nucleic acid molecule of claim 16.

19. A composition comprising the anti-PD-L1 antibody of claim 1, and a pharmaceutically acceptable carrier.

20. A method of treating cancer in a subject, comprising administering an effective amount of the composition of claim 19 to the subject.

21. The method of claim 20, wherein the cancer is selected from the group consisting of melanoma, NSCLC, head and neck cancer, urothelial cancer, triple-negative breast cancer (TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer, esophageal cancer, nasopharyngeal carcinoma (NPC), biliary tract cancer, colorectal cancer, breast cancer, cervical cancer, thyroid cancer and salivary cancer.

22. The method of claim 20, wherein the subject is further treated with a radiation therapy or a surgery.

23. A method of producing an anti-PD-L1 antibody comprising culturing the cell or the cell line of claim 18 and recovering the anti-PD-L1 antibody from the cell culture.

* * * * *